(12) United States Patent
Zak et al.

(10) Patent No.: US 11,795,170 B2
(45) Date of Patent: Oct. 24, 2023

(54) THERAPEUTIC COMPOUNDS, COMPOSITIONS AND METHODS OF USE THEREOF

(71) Applicant: Genentech, Inc., South San Francisco, CA (US)

(72) Inventors: Mark Zak, San Carlos, CA (US); Terry Kellar, Burlingame, CA (US); Paul Gibbons, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 221 days.

(21) Appl. No.: 17/027,352

(22) Filed: Sep. 21, 2020

(65) Prior Publication Data

US 2021/0009599 A1    Jan. 14, 2021

Related U.S. Application Data

(63) Continuation of application No. 16/104,347, filed on Aug. 17, 2018, now abandoned, which is a continuation of application No. PCT/EP2017/053576, filed on Feb. 17, 2017.

(60) Provisional application No. 62/297,061, filed on Feb. 18, 2016.

(51) Int. Cl.
*C07D 487/04* (2006.01)
*A61P 11/06* (2006.01)

(52) U.S. Cl.
CPC ............ *C07D 487/04* (2013.01); *A61P 11/06* (2018.01)

(58) Field of Classification Search
CPC ........... A61P 11/06; A61P 29/00; A61P 43/00; C07D 487/04
See application file for complete search history.

(56) References Cited

FOREIGN PATENT DOCUMENTS

| CN | 102482284 A | 5/2012 |
| WO | 2011/003065 A2 | 1/2011 |
| WO | 2014/039595 A1 | 3/2014 |
| WO | 2015/068856 A1 | 5/2015 |
| WO | 2015/177326 A1 | 11/2015 |

OTHER PUBLICATIONS

"International Preliminary Report on Patentability—PCT/EP2017/053576" (Chap. I—Date of Report Issuance: Aug. 21, 2018),:1-7 (dated Aug. 30, 2018).
"International Search Report—PCT/EP2017/053576":1-5 (dated Mar. 23, 2017).

*Primary Examiner* — Jeffrey S Lundgren
*Assistant Examiner* — William Y Lee
(74) *Attorney, Agent, or Firm* — Robert C. Hall

(57) ABSTRACT

Compounds of Formula (I):

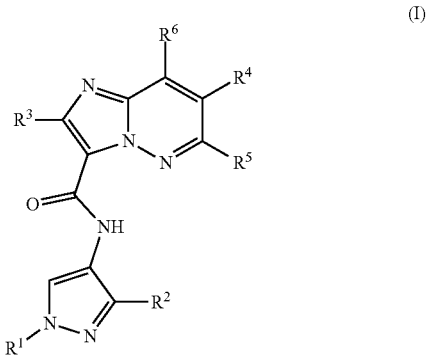

salts thereof and methods of making and use as Janus kinase inhibitors are described herein.

2 Claims, No Drawings

THERAPEUTIC COMPOUNDS, COMPOSITIONS AND METHODS OF USE THEREOF

CROSS-REFERENCE TO RELATED APPLICATIONS

This patent application is a continuation of U.S. application Ser. No. 16/104,347 filed on Aug. 17, 2018, which is continuation of International Application No. PCT/EP2017/053576, filed Feb. 17, 2017, which claims the benefit of U.S. Provisional Appl. No. 62/297,061, filed Feb. 18, 2016, each of which is incorporated herein by reference in its entirety.

FIELD OF THE INVENTION

The field of the invention pertains to compounds that are inhibitors of a Janus kinase, such as JAK1, as well as compositions containing these compounds, and methods of use including, but not limited to, diagnosis or treatment of patients suffering from a condition responsive to the inhibition of a JAK kinase.

BACKGROUND OF INVENTION

Cytokine pathways mediate a broad range of biological functions, including many aspects of inflammation and immunity. Janus kinases (JAK), including JAK1, JAK2, JAK3 and TYK2, are cytoplasmic protein kinases that associate with type I and type II cytokine receptors and regulate cytokine signal transduction. Cytokine engagement with cognate receptors triggers activation of receptor associated JAKs and this leads to JAK-mediated tyrosine phosphorylation of signal transducer and activator of transcription (STAT) proteins and ultimately transcriptional activation of specific gene sets (Schindler et al., 2007, J. Biol. Chem. 282: 20059-63). JAK1, JAK2 and TYK2 exhibit broad patterns of gene expression, while JAK3 expression is limited to leukocytes. Cytokine receptors are typically functional as heterodimers, and as a result, more than one type of JAK kinase is usually associated with cytokine receptor complexes. The specific JAKs associated with different cytokine receptor complexes have been determined in many cases through genetic studies and corroborated by other experimental evidence. Exemplary therapeutic benefits of the inhibition of JAK enzymes are discussed, for example, in International Application No. WO 2013/014567.

JAK1 was initially identified in a screen for novel kinases (Wilks A. F., 1989, Proc. Natl. Acad. Sci. U.S.A. 86:1603-1607). Genetic and biochemical studies have shown that JAK1 is functionally and physically associated with the type I interferon (e.g., IFNalpha), type II interferon (e.g., IFN-gamma), and IL-2 and IL-6 cytokine receptor complexes (Kisseleva et al., 2002, Gene 285:1-24; Levy et al., 2005, Nat. Rev. Mol. Cell Biol. 3:651-662; O'Shea et al., 2002, Cell, 109 (suppl.): S121-S131). JAK1 knockout mice die perinatally due to defects in LIF receptor signalling (Kisseleva et al., 2002, Gene 285:1-24; O'Shea et al., 2002, Cell, 109 (suppl.): S121-S131). Characterization of tissues derived from JAK1 knockout mice demonstrated critical roles for this kinase in the IFN, IL-10, IL-2/IL-4 and IL-6 pathways. A humanized monoclonal antibody targeting the IL-6 pathway (Tocilizumab) was recently approved by the European Commission for the treatment of moderate-to-severe rheumatoid arthritis (Scheinecker et al., 2009, Nat. Rev. Drug Discov. 8:273-274).

CD4 T cells play an important role in asthma pathogenesis through the production of TH2 cytokines within the lung, including IL-4, IL-9 and IL-13 (Cohn et al., 2004, Annu. Rev. Immunol. 22:789-815). IL-4 and IL-13 induce increased mucus production, recruitment of eosinophils to the lung, and increased production of IgE (Kasaian et al., 2008, Biochem. Pharmacol. 76(2): 147-155). IL-9 leads to mast cell activation, which exacerbates the asthma symptoms (Kearley et al., 2011, Am. J. Resp. Crit. Care Med., 183(7): 865-875). The IL-4Rα chain activates JAK1 and binds to either IL-4 or IL-13 when combined with the common gamma chain or the IL-13Rα1 chain respectively (Pemis et al., 2002, J. Clin. Invest. 109(10):1279-1283). The common gamma chain can also combine with IL-9Rα to bind to IL-9, and IL-9Rα activates JAK1 as well (Demoulin et al., 1996, Mol. Cell Biol. 16(9):4710-4716). While the common gamma chain activates JAK3, it has been shown that JAK1 is dominant over JAK3, and inhibition of JAK1 is sufficient to inactivate signaling through the common gamma chain despite JAK3 activity (Haan et al., 2011, Chem. Biol. 18(3):314-323). Inhibition of IL-4, IL-13 and IL-9 signaling by blocking the JAK/STAT signaling pathway can alleviate asthmatic symptoms in pre-clinical lung inflammation models (Mathew et al., 2001, J. Exp. Med. 193(9): 1087-1096; Kudlacz et. al., 2008, Eur. J. Pharmacol. 582(1-3): 154-161).

Biochemical and genetic studies have shown an association between JAK2 and single-chain (e.g., EPO), IL-3 and interferon gamma cytokine receptor families (Kisseleva et al., 2002, Gene 285:1-24; Levy et al., 2005, Nat. Rev. Mol. Cell Biol. 3:651-662; O'Shea et al., 2002, Cell, 109 (suppl.): S121-S131). Consistent with this, JAK2 knockout mice die of anemia (O'Shea et al., 2002, Cell, 109 (suppl.): S121-S131). Kinase activating mutations in JAK2 (e.g., JAK2 V617F) are associated with myeloproliferative disorders in humans.

JAK3 associates exclusively with the gamma common cytokine receptor chain, which is present in the IL-2, IL-4, IL-7, IL-9, IL-15 and IL-21 cytokine receptor complexes. JAK3 is critical for lymphoid cell development and proliferation and mutations in JAK3 result in severe combined immunodeficiency (SCID) (O'Shea et al., 2002, Cell, 109 (suppl.): S121-S131). Based on its role in regulating lymphocytes, JAK3 and JAK3-mediated pathways have been targeted for immunosuppressive indications (e.g., transplantation rejection and rheumatoid arthritis) (Baslund et al., 2005, Arthritis & Rheumatism 52:2686-2692; Changelian et al., 2003, Science 302: 875-878).

TYK2 associates with the type I interferon (e.g., IFNalpha), IL-6, IL-10, IL-12 and IL-23 cytokine receptor complexes (Kisseleva et al., 2002, Gene 285:1-24; Watford, W. T. & O'Shea, J. J., 2006, Immunity 25:695-697). Consistent with this, primary cells derived from a TYK2 deficient human are defective in type I interferon, IL-6, IL-10, IL-12 and IL-23 signalling. A fully human monoclonal antibody targeting the shared p40 subunit of the IL-12 and IL-23 cytokines (Ustekinumab) was recently approved by the European Commission for the treatment of moderate-to-severe plaque psoriasis (Krueger et al., 2007, N. Engl. J. Med. 356:580-92; Reich et al., 2009, Nat. Rev. Drug Discov. 8:355-356). In addition, an antibody targeting the IL-12 and IL-23 pathways underwent clinical trials for treating Crohn's Disease (Mannon et al., 2004, N. Engl. J. Med. 351:2069-79).

Currently there remains a need for additional compounds that are inhibitors of Janus kinases. For example, there is a need for compounds that possess useful potency as inhibitors of one or more Janus kinase (e.g. JAK1) in combination with other pharmacological properties that are necessary to achieve a useful therapeutic benefit. For example, there is a need for potent compounds that demonstrate selectivity for one Janus kinase over other kinases in general (e.g. selectivity for JAK1 over other kinases such as leucine-rich repeat kinase 2 LRRK2). There is also a need for potent compounds that demonstrate selectivity for one Janus kinase over other Janus kinases (e.g. selectivity for JAK1 over other Janus kinases). Kinases demonstrating selectivity for JAK1 could provide a therapeutic benefit, with fewer side effects, in conditions responsive to the inhibition of JAK1. Additionally there is currently a need for potent JAK1 inhibitors that possess other properties (e.g. melting point, pK, solubility, etc.) necessary for formulation and administration by inhalation. Such compounds would be particularly useful for treating conditions such as, for example, asthma.

SUMMARY OF INVENTION

One aspect of the invention includes a compound of the invention, which is a compound of Formula (I):

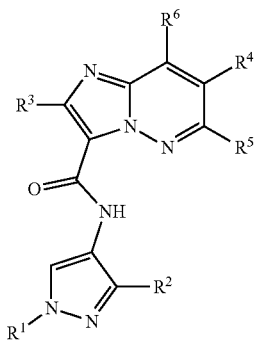

(I)

or a salt thereof, wherein:

$R^1$ is $C_2$-$C_6$alkenyl, $C_2$-$C_6$alkynyl, —($C_0$-$C_3$alkyl)CN, —($C_0$-$C_3$alkyl)OR$^a$, —($C_0$-$C_3$alkyl)R$^a$, —($C_0$-$C_3$alkyl)SR$^a$, —($C_0$-$C_3$alkyl)NR$^a$R$^b$, —($C_0$-$C_3$alkyl)OCF$_3$, —($C_0$-$C_3$alkyl)CF$_3$, —($C_0$-$C_3$alkyl)NO$_2$, —($C_0$-$C_3$alkyl)C(O)R$^a$, —($C_0$-$C_3$alkyl)C(O)OR$^a$, —($C_0$-$C_3$alkyl)C(O)NR$^a$R$^b$, —($C_0$-$C_3$alkyl)NR$^a$C(O)R$^b$, —($C_0$-$C_3$alkyl)S(O)$_{1-2}$R$^a$, —($C_0$-$C_3$alkyl)NR$^a$S(O)$_{1-2}$R$^b$, —($C_0$-$C_3$alkyl)S(O)$_{1-2}$NR$^a$R$^b$, —($C_0$-$C_6$alkyl)(5-6-membered heteroaryl) or —($C_0$-$C_6$alkyl)phenyl, wherein R$^1$ is optionally substituted by one or more groups independently selected from the group consisting of halogen, $C_1$-$C_3$alkyl, oxo, —CF$_3$, —($C_0$-$C_3$alkyl)OR$^c$ and —($C_0$-$C_3$alkyl)NR$^c$R$^d$;

R$^a$ is independently hydrogen, $C_1$-$C_6$alkyl, $C_3$-$C_6$ cycloalkyl, 3-10 membered heterocyclyl, —C(O)R$^c$, —C(O)OR$^c$, —C(O)NR$^c$R$^d$, —NR$^c$C(O)R$^d$, —S(O)$_{1-2}$R$^c$, —NR$^c$S(O)$_{1-2}$R$^d$ or —S(O)$_{1-2}$NR$^c$R$^d$, wherein any $C_3$-$C_6$ cycloalkyl, and 3-10 membered heterocyclyl of R$^a$ is optionally substituted with one or more groups R$^e$;

R$^b$ is independently hydrogen or $C_1$-$C_3$alkyl, wherein said alkyl is optionally substituted by one or more groups independently selected from the group consisting of halogen and oxo;

R$^c$ and R$^d$ are independently selected from the group consisting of hydrogen, 3-6 membered heterocyclyl, $C_3$-$C_6$ cycloalkyl, and $C_1$-$C_3$alkyl, wherein any 3-6 membered heterocyclyl, $C_3$-$C_6$ cycloalkyl, and $C_1$-$C_3$alkyl of R$^c$ and R$^d$ is optionally substituted by one or more groups independently selected from the group consisting of halogen and oxo; or R$^c$ and R$^d$ are taken together with the atom to which they are attached to form a 3-6-membered heterocyclyl, optionally substituted by one or more groups independently selected from the group consisting of halogen, oxo, —CF$_3$, and $C_1$-$C_3$alkyl;

each R$^e$ is independently selected from the group consisting of oxo, OR$^f$, NR$^f$R$^g$, halogen, 3-10 membered heterocyclyl, $C_3$-$C_6$ cycloalkyl, and $C_1$-$C_6$alkyl, wherein any $C_3$-$C_6$ cycloalkyl and $C_1$-$C_6$alkyl of R$^e$ is optionally substituted by one or more groups independently selected from the group consisting of OR$^f$, NR$^f$R$^g$, halogen, 3-10 membered heterocyclyl, oxo, and cyano, and wherein any 3-10 membered heterocyclyl of R$^e$ and any 3-10 membered heterocyclyl group substituted on a $C_3$-$C_6$ cycloalkyl or $C_1$-$C_6$alkyl of R$^e$ is optionally substituted by one or more groups independently selected from the group consisting of halogen, oxo, cyano, —CF$_3$, NR$^h$R$^k$, 3-6 membered heterocyclyl, and $C_1$-$C_3$alkyl that is optionally substituted by one or more groups independently selected from the group consisting of halogen, oxo, OR$^f$, and NR$^h$R$^k$;

R$^f$ and R$^g$ are each independently selected from the group consisting of hydrogen, $C_1$-$C_6$alkyl, 3-6 membered heterocyclyl, and $C_3$-$C_6$ cycloalkyl, wherein any $C_1$-$C_6$alkyl, 3-6 membered heterocyclyl, and $C_3$-$C_6$ cycloalkyl of R$^f$ and R$^g$ is optionally substituted by one or more R$^m$;

R$^h$ and R$^k$ are each independently selected from the group consisting of hydrogen and $C_1$-$C_6$alkyl that is optionally substituted by one or more groups independently selected from the group consisting of halogen, cyano, 3-6 membered heterocyclyl, and oxo; or R$^h$ and R$^k$ are taken together with the atom to which they are attached to form a 3-6-membered heterocyclyl that is optionally substituted by one or more groups independently selected from the group consisting of halogen, cyano, oxo, CF$_3$ and $C_1$-$C_3$alkyl that is optionally substituted by one or more groups independently selected from the group consisting of halogen and oxo;

each R$^m$ is independently selected from the group consisting of halogen, cyano, oxo, $C_3$-$C_6$cycloalkyl, hydroxy, and NR$^h$R$^k$, wherein any $C_3$-$C_6$cycloalkyl of R$^m$ is optionally substituted with one or more groups independently selected from the group consisting of halogen, oxo, cyano, and $C_1$-$C_3$alkyl;

R$^2$ is phenyl, $C_3$-$C_6$ cycloalkyl or 3-10 membered heterocyclyl, wherein R$^2$ is optionally substituted by 1-5 R$^n$;

each R$^n$ is independently $C_1$-$C_6$ alkyl, $C_2$-$C_6$ alkenyl, $C_2$-$C_6$ alkynyl, oxo, halogen, —($C_0$-$C_3$ alkyl)CN, —($C_0$-$C_3$ alkyl)OR$^o$, —($C_0$-$C_3$ alkyl)SR$^o$, —($C_0$-$C_3$ alkyl)NR$^o$R$^p$, —($C_0$-$C_3$ alkyl)OCF$_3$, —($C_0$-$C_3$ alkyl)CF$_3$, —($C_0$-$C_3$ alkyl)NO$_2$, —($C_0$-$C_3$ alkyl)C(O)R$^o$, —($C_0$-$C_3$ alkyl)C(O)OR$^o$, —($C_0$-$C_3$ alkyl)C(O)NR$^o$R$^p$, —($C_0$-$C_3$ alkyl)NR$^o$C(O)R$^p$, —($C_0$-$C_3$ alkyl)S(O)$_{1-2}$R$^o$, —($C_0$-$C_3$ alkyl)NR$^o$S(O)$_{1-2}$R$^p$, —($C_0$-$C_3$ alkyl)S(O)$_{1-2}$NR$^o$R$^p$, —($C_0$-$C_3$ alkyl)($C_3$-$C_6$ cycloalkyl), —($C_0$-$C_3$ alkyl)(3-6-membered heterocyclyl), —($C_0$-$C_3$ alkyl)C(O)(3-6-membered heterocyclyl), or —($C_0$-$C_3$ alkyl)phenyl, wherein R$^5$ is independently optionally substituted by halogen, $C_1$-$C_3$ alkyl, oxo, —CF$_3$, —($C_0$-$C_3$ alkyl)OR$^r$ or —($C_0$-$C_3$ alkyl)NR$^r$R$^s$; or two R$^n$ are taken together to form —O(CH$_2$)$_{1-3}$O—;

R$^3$ is H, halogen, cyano, $C_1$-$C_3$alkyl, $C_2$-$C_3$alkenyl, $C_2$-$C_3$alkynyl, —NH$_2$, or —OR$^t$;

R$^4$ is H, halogen, cyano, $C_1$-$C_3$alkyl, $C_2$-$C_3$alkenyl, $C_2$-$C_3$alkynyl, —NH$_2$, or —OR$^t$;

R$^5$ is H, halogen, cyano, $C_1$-$C_3$alkyl, $C_2$-$C_3$alkenyl, $C_2$-$C_3$alkynyl, —NH$_2$, or —OR$^t$;

R$^6$ is H, halogen, cyano, $C_1$-$C_3$alkyl, $C_2$-$C_3$alkenyl, $C_2$-$C_3$alkynyl, —NH$_2$, or —OR$^t$;

$R^o$ is independently hydrogen, $C_1$-$C_6$ alkyl, $C_2$-$C_6$ alkenyl, $C_2$-$C_6$ alkynyl, $C_3$-$C_6$ cycloalkyl, 3-6 membered heterocyclyl, ($C_3$-$C_6$ cycloalkyl)$C_1$-$C_6$ alkyl, (3-6-membered heterocyclyl)$C_1$-$C_6$ alkyl, —C(O)($C_3$-$C_6$ cycloalkyl), or —C(O)(3-6-membered heterocyclyl), —C(O)R$^r$, —C(O)OR$^r$, —C(O)NR$^r$R$^s$, —NR$^r$C(O)R$^s$, —S(O)$_{1-2}$R$^r$, —NR$^r$S(O)$_{1-2}$R$^s$ or —S(O)$_{1-2}$NR$^r$R$^s$, wherein said alkyl, cycloalkyl and heterocyclyl are independently optionally substituted by oxo, $C_1$-$C_3$ alkyl, OR$^r$, NR$^r$R$^s$ or halogen;

$R^p$ is independently hydrogen or $C_1$-$C_3$ alkyl, wherein said alkyl is independently optionally substituted by halogen or oxo;

or $R^o$ and $R^p$ are taken together with the atom to which they are attached to form a 3-6-membered heterocyclyl, optionally substituted by halogen, oxo, or $C_1$-$C_3$ alkyl optionally substituted by halogen;

$R^r$ and $R^s$ are independently hydrogen or $C_1$-$C_3$ alkyl optionally substituted by halogen or oxo; or $R^r$ and $R^s$ are taken together with the atom to which they are attached to form a 3-6-membered heterocyclyl, optionally substituted by halogen, oxo, or $C_1$-$C_3$ alkyl optionally substituted by halogen; and each $R^t$ is independently H, $C_1$-$C_6$ alkyl, $C_2$-$C_6$ alkenyl, $C_2$-$C_6$ alkynyl, or —($C_0$-$C_3$ alkyl)phenyl.

Also provided is a pharmaceutical composition that comprises a compound of the invention and a pharmaceutically acceptable carrier, diluent or excipient.

Another aspect includes a compound of the invention for use in therapy, such as the treatment of an inflammatory disease or cancer.

Another aspect includes a method of preventing, treating or lessening the severity of a disease or condition responsive to the inhibition of a Janus kinase, such as JAK1 kinase, in a patient. The method can comprise administering to the patient a therapeutically effective amount of a compound of the invention.

Another aspect includes the use of a compound of the invention in the manufacture of a medicament for the treatment of a disease responsive to the inhibition of a Janus kinase, such as JAK1 kinase.

Another aspect includes a kit for treating a disease or disorder responsive to the inhibition of a Janus kinase, such as JAK1 kinase. The kit can comprise a first pharmaceutical composition comprising a compound of the invention, and instructions for use.

Certain compounds of the invention possess beneficial potency as inhibitors of one or more Janus kinase (e.g. JAK1). Certain compounds are also, a) selective for one Janus kinase over other kinases, b) selective for JAK1 over other Janus kinases, and/or c) possess other properties (e.g. melting point, pK, solubility, etc.) necessary for formulation and administration by inhalation. Certain compounds of formula (I) may be particularly useful for treating conditions such as asthma.

DETAILED DESCRIPTION OF THE INVENTION

Definitions

"Halogen" or "halo" refers to F, Cl, Br or I. Additionally, terms such as "haloalkyl," are meant to include monohaloalkyl and polyhaloalkyl.

The term "alkyl" refers to a saturated linear or branched-chain monovalent hydrocarbon radical, wherein the alkyl radical may be optionally substituted. In one example, the alkyl radical is one to eighteen carbon atoms ($C_1$-$C_{18}$). In other examples, the alkyl radical is $C_0$-$C_6$, $C_0$-$C_5$, $C_0$-$C_3$, $C_1$-$C_{12}$, $C_1$-$C_{10}$, $C_1$-$C_8$, $C_1$-$C_6$, $C_1$-$C_5$, $C_1$-$C_4$, or $C_1$-$C_3$. $C_0$ alkyl refers to a bond. Examples of alkyl groups include methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$), 1-heptyl and 1-octyl. In some embodiments, substituents for "optionally substituted alkyls" include one to four instances of F, Cl, Br, I, OH, SH, CN, NH$_2$, NHCH$_3$, N(CH$_3$)$_2$, NO$_2$, N$_3$, C(O)CH$_3$, COOH, CO$_2$CH$_3$, methyl, ethyl, propyl, iso-propyl, butyl, isobutyl, cyclopropyl, methoxy, ethoxy, propoxy, oxo, trifluoromethyl, difluoromethyl, sulfonylamino, methanesulfonylamino, SO, SO$_2$, phenyl, piperidinyl, piperizinyl, and pyrimidinyl, wherein the alkyl, phenyl and heterocyclic portions thereof may be optionally substituted, such as by one to four instances of substituents selected from this same list.

"Aryl" refers to a carbocyclic aromatic group, whether or not fused to one or more groups, having the number of carbon atoms designated, or if no number is designated, up to 14 carbon atoms. One example includes aryl groups having 6-14 carbon atoms. Another example includes aryl groups having 6-10 carbon atoms. Examples of aryl groups include phenyl, naphthyl, biphenyl, phenanthrenyl, naphthacenyl, 1,2,3,4-tetrahydronaphthalenyl, 1H-indenyl, 2,3-dihydro-1H-indenyl, and the like (see, e.g., Lang's Handbook of Chemistry (Dean, J. A., ed.) 13$^{th}$ ed. Table 7-2 [1985]). A particular aryl is phenyl. Substituted phenyl or substituted aryl means a phenyl group or aryl group substituted with one, two, three, four or five substituents, for example, 1-2, 1-3 or 1-4 substituents, such as chosen from groups specified herein (see "optionally substituted" definition), such as F, Cl, Br, I, OH, SH, CN, NH$_2$, NHCH$_3$, N(CH$_3$)$_2$, NO$_2$, N$_3$, C(O)CH$_3$, COOH, CO$_2$CH$_3$, methyl, ethyl, propyl, iso-propyl, butyl, isobutyl, cyclopropyl, methoxy, ethoxy, propoxy, oxo, trifluoromethyl, difluoromethyl, sulfonylamino, methanesulfonylamino, SO, SO$_2$, phenyl, piperidinyl, piperizinyl, and pyrimidinyl, wherein the alkyl, phenyl and heterocyclic portions thereof may be optionally substituted, such as by one to four instances of substituents selected from this same list. Examples of the term "substituted phenyl" include a mono- or di(halo)phenyl group such as 2-chlorophenyl, 2-bromophenyl, 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl, 2,4-difluorophenyl and the like; a mono- or di(hydroxy)phenyl group such as 4-hydroxyphenyl, 3-hydroxyphenyl, 2,4-dihydroxyphenyl, the protected-hydroxy derivatives thereof and the like; a nitrophenyl group such as 3- or 4-nitrophenyl; a cyanophenyl group, for example, 4-cyanophenyl; a mono- or di(alkyl)phenyl group such as 4-methylphenyl, 2,4-dimethylphenyl, 2-methylphenyl, 4-(isopropyl)phenyl, 4-ethylphenyl, 3-(n-propyl)phenyl and the like; a mono or di(alkoxy)phenyl group, for example, 3,4-dimethoxyphenyl, 3-methoxy-4-benzyloxyphenyl, 3-ethoxyphenyl, 4-(isopropoxy)phenyl, 4-(t-butoxy)phenyl, 3-ethoxy-4-methoxyphenyl and the like; 3- or 4-trifluoromethylphenyl; a mono- or dicarboxyphenyl or (protected carboxy)phenyl group such 4-carboxyphenyl, a mono- or di(hydroxymethyl)phenyl or (protected hydroxymethyl)phenyl such as 3-(protected hydroxymethyl)phenyl or 3,4-di(hydroxymethyl)phenyl; a mono- or di(aminomethyl)phenyl or (protected aminomethyl)phenyl such as 2-(aminomethyl)phenyl or 2,4-(protected aminomethyl)phenyl; or a mono- or di(N-(methylsulfonylamino))phenyl such as 3-(N-methylsulfonylamino))phenyl. Also, the term "substituted phenyl" represents disubstituted phenyl groups where the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl, 2-chloro-5-difluoromethoxy and the like, as well as trisubstituted phenyl groups where the substituents are different, for example 3-methoxy-4-benzyloxy-6-methyl sulfonylamino, 3-methoxy-4-benzyloxy-6-phenyl sulfonylamino, and tetrasubstituted phenyl groups where the substituents are different such as 3-methoxy-4-benzyloxy-5-methyl-6-phenyl sulfonylamino.

The terms "compound(s) of the invention," and "compound(s) of the present invention" and the like, unless otherwise indicated, include compounds of Formula (I), (Ia), (Ib), (Ic), (Id), (Ie), (If), (Ig), (Ih), (Ij), (Ik), (Im), (In), and the compounds of the Examples herein, including stereoisomers (including atropisomers), geometric isomers, tautomers, solvates, metabolites, isotopes, salts (e.g., pharmaceutically acceptable salts), and prodrugs thereof. In some embodiments, solvates, metabolites, isotopes or prodrugs are excluded, or any combination thereof.

"Cycloalkyl" refers to a non-aromatic, saturated or partially unsaturated hydrocarbon ring group wherein the cycloalkyl group may be optionally substituted independently with one or more substituents described herein. In one example, the cycloalkyl group is 3 to 12 carbon atoms ($C_3$-$C_{12}$). In other examples, cycloalkyl is $C_3$-$C_8$, $C_3$-$C_{10}$ or $C_5$-$C_{10}$. In other examples, the cycloalkyl group, as a monocycle, is $C_3$-$C_8$, $C_3$-$C_6$ or $C_5$-$C_6$. In another example, the cycloalkyl group, as a bicycle, is $C_7$-$C_{12}$. In another example, the cycloalkyl group, as a spiro system, is $C_5$-$C_{12}$. Examples of monocyclic cycloalkyl include cyclopropyl, cyclobutyl, cyclopentyl, 1-cyclopent-1-enyl, 1-cyclopent-2-enyl, 1-cyclopent-3-enyl, cyclohexyl, perdeuteriocyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl and cyclododecyl. Exemplary arrangements of bicyclic cycloalkyls having 7 to 12 ring atoms include, but are not limited to, [4,4], [4,5], [5,5], [5,6] or [6,6] ring systems. Exemplary bridged bicyclic cycloalkyls include, but are not limited to, bicyclo[2.2.1]heptane, bicyclo[2.2.2]octane and bicyclo[3.2.2]nonane. Examples of spiro cycloalkyl include, spiro[2.2]pentane, spiro[2.3]hexane, spiro[2.4]heptane, spiro[2.5]octane and spiro[4.5]decane. In some embodiments, substituents for "optionally substituted cycloalkyls" include one to four instances of F, Cl, Br, I, OH, SH, CN, $NH_2$, $NHCH_3$, $N(CH_3)_2$, $NO_2$, $N_3$, $C(O)CH_3$, COOH, $CO_2CH_3$, methyl, ethyl, propyl, isopropyl, butyl, isobutyl, cyclopropyl, methoxy, ethoxy, propoxy, oxo, trifluoromethyl, difluoromethyl, sulfonylamino, methanesulfonylamino, SO, $SO_2$, phenyl, piperidinyl, piperizinyl, and pyrimidinyl, wherein the alkyl, aryl and heterocyclic portions thereof may be optionally substituted, such as by one to four instances of substituents selected from this same list.

"Heterocyclic group", "heterocyclic", "heterocycle", "heterocyclyl", or "heterocyclo" are used interchangeably and refer to any mono-, bi-, tricyclic or spiro, saturated or unsaturated, aromatic (heteroaryl) or non-aromatic (e.g., heterocycloalkyl), ring system, having 3 to 20 ring atoms, where the ring atoms are carbon, and at least one atom in the ring or ring system is a heteroatom selected from nitrogen, sulfur or oxygen. If any ring atom of a cyclic system is a heteroatom, that system is a heterocycle, regardless of the point of attachment of the cyclic system to the rest of the molecule. In one example, heterocyclyl includes 3-10 ring atoms ("members") and includes monocycles, bicycles, tricycles and spiro ring systems, wherein the ring atoms are carbon, where at least one atom in the ring or ring system is a heteroatom selected from nitrogen, sulfur or oxygen. In one example, heterocyclyl includes 1 to 4 heteroatoms. In one example, heterocyclyl includes 1 to 3 heteroatoms. In another example, heterocyclyl includes 3- to 7-membered monocycles having 1-2, 1-3 or 1-4 heteroatoms selected from nitrogen, sulfur or oxygen. In another example, heterocyclyl includes 4- to 6-membered monocycles having 1-2, 1-3 or 1-4 heteroatoms selected from nitrogen, sulfur or oxygen. In another example, heterocyclyl includes 3-membered monocycles. In another example, heterocyclyl includes 4-membered monocycles. In another example, heterocyclyl includes 5-6 membered monocycles, e.g., 5-6 membered heteroaryl. In another example, heterocyclyl includes 3-11 membered heterocycloyalkyls, such as 4-11 membered heterocycloalkyls. In some embodiments, a heterocycloalkyl includes at least one nitrogen. In one example, the heterocyclyl group includes 0 to 3 double bonds. Any nitrogen or sulfur heteroatom may optionally be oxidized (e.g., NO, SO, $SO_2$), and any nitrogen heteroatom may optionally be quaternized (e.g., $[NR_4]^+Cl^-$, $[NR_4]^+OH^-$). Example heterocycles are oxiranyl, aziridinyl, thiiranyl, azetidinyl, oxetanyl, thietanyl, 1,2-dithietanyl, 1,3-dithietanyl, pyrrolidinyl, dihydro-1H-pyrrolyl, dihydrofuranyl, tetrahydrofuranyl, dihydrothienyl, tetrahydrothienyl, imidazolidinyl, piperidinyl, piperazinyl, isoquinolinyl, tetrahydroisoquinolinyl, morpholinyl, thiomorpholinyl, 1,1-dioxo-thiomorpholinyl, dihydropyranyl, tetrahydropyranyl, hexahydrothiopyranyl, hexahydropyrimidinyl, oxazinanyl, thiazinanyl, thioxanyl, homopiperazinyl, homopiperidinyl, azepanyl, oxepanyl, thiepanyl, oxazepinyl, oxazepanyl, diazepanyl, 1,4-diazepanyl, diazepinyl, thiazepinyl, thiazepanyl, tetrahydrothiopyranyl, oxazolidinyl, thiazolidinyl, isothiazolidinyl, 1,1-dioxoisothiazolidinonyl, oxazolidinonyl, imidazolidinonyl, 4,5,6,7-tetrahydro[2H]indazolyl, tetrahydrobenzoimidazolyl, 4,5,6,7-tetrahydrobenzo[d]imidazolyl, 1,6-dihydroimidazol[4,5-d]pyrrolo[2,3-b]pyridinyl, thiazinyl, oxazinyl, thiadiazinyl, oxadiazinyl, dithiazinyl, dioxazinyl, oxathiazinyl, thiatriazinyl, oxatriazinyl, dithiadiazinyl, imidazolinyl, dihydropyrimidyl, tetrahydropyrimidyl, 1-pyrrolinyl, 2-pyrrolinyl, 3-pyrrolinyl, indolinyl, thiapyranyl, 2H-pyranyl, 4H-pyranyl, dioxanyl, 1,3-dioxolanyl, pyrazolinyl, pyrazolidinyl, dithianyl, dithiolanyl, pyrimidinonyl, pyrimidindionyl, pyrimidin-2,4-dionyl, piperazinonyl, piperazindionyl, pyrazolidinylimidazolinyl, 3-azabicyclo[3.1.0]hexanyl, 3,6-diazabicyclo[3.1.1]heptanyl, 6-azabicyclo[3.1.1]heptanyl, 3-azabicyclo[3.1.1]heptanyl, 3-azabicyclo[4.1.0]heptanyl, azabicyclo[2.2.2]hexanyl, 2-azabicyclo[3.2.1]octanyl, 8-azabicyclo[3.2.1]octanyl, 2-azabicyclo[2.2.2]octanyl, 8-azabicyclo[2.2.2]octanyl, 7-oxabicyclo[2.2.1]heptane, azaspiro[3.5]nonanyl, azaspiro[2.5]octanyl, azaspiro[4.5]decanyl, 1-azaspiro[4.5]decan-2-only, azaspiro[5.5]undecanyl, tetrahydroindolyl, octahydroindolyl, tetrahydroisoindolyl, tetrahydroindazolyl, 1,1-dioxohexahydrothiopyranyl. Examples of 5-membered heterocycles containing a sulfur or oxygen atom and one to three nitrogen atoms are thiazolyl, including thiazol-2-yl and thiazol-2-yl N-oxide, thiadiazolyl, including 1,3,4-thiadiazol-5-yl and 1,2,4-thiadiazol-5-yl, oxazolyl, for example oxazol-2-yl, and oxadiazolyl, such as 1,3,4-oxadiazol-5-yl, and 1,2,4-oxadiazol-5-yl. Example 5-membered ring heterocycles containing 2 to 4 nitrogen atoms include imidazolyl, such as imidazol-2-yl; triazolyl, such as 1,3,4-triazol-5-yl; 1,2,3-triazol-5-yl, 1,2,4-triazol-5-yl, and tetrazolyl, such as 1H-tetrazol-5-yl. Example benzo-fused 5-membered heterocycles are benzoxazol-2-yl, benzthiazol-2-yl and benzimidazol-2-yl. Example 6-membered heterocycles contain one to three nitrogen atoms and optionally a sulfur or oxygen atom, for example pyridyl, such as pyrid-2-yl, pyrid-3-yl, and pyrid-4-yl; pyrimidyl, such as pyrimid-2-yl and pyrimid-4-yl; triazinyl, such as 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl groups, are other example heterocycle groups. Heterocycles may be optionally substituted. For example, substituents for "optionally substituted heterocycles" include one to four instances of F, Cl, Br, I, OH, SH, CN, $NH_2$, $NHCH_3$, $N(CH_3)_2$, $NO_2$, $N_3$, $C(O)CH_3$, COOH, $CO_2CH_3$, methyl, ethyl, propyl, iso-propyl, butyl, isobutyl, cyclopropyl, methoxy, ethoxy, propoxy, oxo, trifluoromethyl, difluoromethyl, sulfonylamino, methanesulfonylamino, SO, $SO_2$, phenyl, piperidinyl, piperizinyl, and pyrimidinyl, wherein the alkyl, aryl and heterocyclic portions thereof may be optionally substituted, such as by one to four instances of substituents selected from this same list. In some embodiments, a substituent of a heterocyclic group, such as a heteroaryl or heterocycloalkyl, comprises an amide. For example, a heterocyclic (e.g., heteroaryl or heterocycloalkyl) substituent may be —$(CH_2)_{0-4}$CONR'R", wherein R' and R" each independently refer to groups including, for example, hydrogen; unsubstituted $C_1$-$C_6$ alkyl; $C_1$-$C_6$ alkyl substituted by halogen, OH, CN, unsubstituted $C_1$-$C_6$ alkyl, unsubstituted $C_1$-$C_6$ alkoxy, oxo or NR'R"; unsubstituted $C_1$-$C_6$ heteroalkyl; $C_1$-$C_6$ heteroalkyl substituted by halogen, OH, CN, unsubstituted $C_1$-$C_6$ alkyl, unsubstituted $C_1$-$C_6$ alkoxy, oxo or NR'R"; unsubstituted $C_6$-$C_{10}$ aryl; $C_6$-$C_{10}$ aryl substituted by halogen, OH, CN, unsubstituted $C_1$-$C_6$ alkyl, unsubstituted $C_1$-$C_6$ alkoxy, or NR'R"; unsubstituted 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S); and 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S) substituted by halogen, OH, CN, unsubstituted $C_1$-$C_6$ alkyl, unsubstituted $C_1$-$C_6$ alkoxy, oxo or NR'R"; or R' and R" can be combined with the nitrogen atom to form a 3-, 4-, 5-, 6-, or 7-membered ring wherein a ring atom is optionally substituted with N, O or S and wherein the ring is optionally substituted with halogen, OH, CN, unsubstituted $C_1$-$C_6$ alkyl, unsubstituted $C_1$-$C_6$ alkoxy, oxo or NR'R".

"Heteroaryl" refers to any mono-, bi-, or tricyclic ring system where at least one ring is a 5- or 6-membered aromatic ring containing from 1 to 4 heteroatoms selected from nitrogen, oxygen, and sulfur, and in an example embodiment, at least one heteroatom is nitrogen. See, for example, Lang's Handbook of Chemistry (Dean, J. A., ed.) $13^{th}$ ed. Table 7-2 [1985]. Included in the definition are any bicyclic groups where any of the above heteroaryl rings are fused to an aryl ring, wherein the aryl ring or the heteroaryl ring is joined to the remainder of the molecule. In one embodiment, heteroaryl includes 5-6 membered monocyclic aromatic groups where one or more ring atoms is nitrogen, sulfur or oxygen. Example heteroaryl groups include thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, triazinyl, tetrazinyl, tetrazolo[1,5-b]pyridazinyl, imidazol[1,2-a]pyrimidinyl and purinyl, as well as benzo-fused derivatives, for example benzoxazolyl, benzofuryl, benzothiazolyl, benzothiadiazolyl, benzotriazolyl, benzoimidazolyl and indolyl. Heteroaryl groups can be optionally substituted. In some embodiments, substituents for "optionally substituted heteroaryls" include one to four instances of F, Cl, Br, I, OH, SH, CN, $NH_2$, $NHCH_3$, $N(CH_3)_2$, $NO_2$, $N_3$, $C(O)CH_3$, COOH, $CO_2CH_3$, methyl, ethyl, propyl, iso-propyl, butyl, isobutyl, cyclopropyl, methoxy, ethoxy, propoxy, trifluoromethyl, difluoromethyl, sulfonylamino, methanesulfonylamino, SO, $SO_2$, phenyl, piperidinyl, piperizinyl, and pyrimidinyl, wherein the alkyl, phenyl and heterocyclic portions thereof may be optionally substituted, such as by one to four instances of substituents selected from this same list. In some embodiments, a substituent of a heteroaryl comprises an amide. For example, a heteroaryl substituent may be —$(CH_2)_{0-4}$CONR'R", wherein R' and R" each independently refer to groups including, for example, hydrogen; unsubstituted $C_1$-$C_6$ alkyl; $C_1$-$C_6$ alkyl substituted by halogen, OH, CN, unsubstituted $C_1$-$C_6$ alkyl, unsubstituted $C_1$-$C_6$ alkoxy, oxo or NR'R"; unsubstituted $C_1$-$C_6$ heteroalkyl; $C_1$-$C_6$ heteroalkyl substituted by halogen, OH, CN, unsubstituted $C_1$-$C_6$ alkyl, unsubstituted $C_1$-$C_6$ alkoxy, oxo or NR'R"; unsubstituted $C_6$-$C_{10}$ aryl; $C_6$-$C_{10}$ aryl substituted by halogen, OH, CN, unsubstituted $C_1$-$C_6$ alkyl, unsubstituted $C_1$-$C_6$ alkoxy, or NR'R"; unsubstituted 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S); and 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S) substituted by halogen, OH, CN, unsubstituted $C_1$-$C_6$ alkyl, unsubstituted $C_1$-$C_6$ alkoxy, oxo or NR'R"; or R' and R" can be combined with the nitrogen atom to form a 3-, 4-, 5-, 6-, or 7-membered ring wherein a ring atom is optionally substituted with N, O or S and wherein the ring is optionally substituted with halogen, OH, CN, unsubstituted $C_1$-$C_6$ alkyl, unsubstituted $C_1$-$C_6$ alkoxy, oxo or NR'R".

In particular embodiments, a heterocyclyl group is attached at a carbon atom of the heterocyclyl group. By way of example, carbon bonded heterocyclyl groups include bonding arrangements at position 2, 3, 4, 5, or 6 of a pyridine ring, position 3, 4, 5, or 6 of a pyridazine ring, position 2, 4, 5, or 6 of a pyrimidine ring, position 2, 3, 5, or 6 of a pyrazine ring, position 2, 3, 4, or 5 of a furan, tetrahydrofuran, thiofuran, thiophene, pyrrole or tetrahydropyrrole ring, position 2, 4, or 5 of an oxazole, imidazole or thiazole ring, position 3, 4, or 5 of an isoxazole, pyrazole, or isothiazole ring, position 2 or 3 of an aziridine ring, position 2, 3, or 4 of an azetidine ring, position 2, 3, 4, 5, 6, 7, or 8 of a quinoline ring or position 1, 3, 4, 5, 6, 7, or 8 of an isoquinoline ring.

In certain embodiments, the heterocyclyl group is N-attached. By way of example, nitrogen bonded heterocyclyl or heteroaryl groups include bonding arrangements at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

The term "alkoxy" refers to a linear or branched monovalent radical represented by the formula —OR in which R is alkyl, as defined herein. Alkoxy groups include methoxy, ethoxy, propoxy, isopropoxy, mono-, di- and tri-fluoromethoxy and cyclopropoxy.

The term "alkanoyl" refers to group (alkyl)-C(=O)—, wherein alkyl is as defined herein. For example, $C_1$-$C_6$alkanoyl refers to a group of formula ($C_1$-$C_5$alkyl)-C(=O)—. Alkanoyl groups include, formyl, acetyl, propanoyl, isopropanoyl, butanoyl, isobutanoyl, pentanoyl, 3-methylpentanoyl, and hexanoyl.

"Optionally substituted" unless otherwise specified means that a group may be unsubstituted or substituted by one or more (e.g., 0, 1, 2, 3, 4, or 5 or more, or any range derivable therein) of the substituents listed for that group in which said substituents may be the same or different. In an embodiment, an optionally substituted group has 1 substituent. In another embodiment an optionally substituted group has 2 substituents. In another embodiment an optionally substituted group has 3 substituents. In another embodiment an optionally substituted group has 4 substituents. In another embodiment an optionally substituted group has 5 substituents.

As used herein a wavy line "⁓" that intersects a bond in a chemical structure indicate the point of attachment of the atom to which the wavy bond is connected in the chemical structure to the remainder of a molecule, or to the remainder of a fragment of a molecule. In some embodiments, an arrow together with an asterisk is used in the manner of a wavy line to indicate a point of attachment.

In certain embodiments, divalent groups are described generically without specific bonding configurations. It is understood that the generic description is meant to include both bonding configurations, unless specified otherwise. For example, in the group $R^1$-$R^2$-$R^3$, if the group $R^2$ is described as —$CH_2C(O)$—, then it is understood that this group can be bonded both as $R^1$—$CH_2C(O)$—$R^3$, and as $R^1$—$C(O)CH_2$—$R^3$, unless specified otherwise.

The phrase "pharmaceutically acceptable" refers to molecular entities and compositions that do not produce an adverse, allergic or other untoward reaction when administered to an animal, such as, for example, a human, as appropriate.

Compounds of the invention may be in the form of a salt, such as a pharmaceutically acceptable salt. "Pharmaceutically acceptable salts" include both acid and base addition salts. "Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, benzenesulfonic acid, p-toluenesulfonic acid, salicyclic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particular base addition salts are the ammonium, potassium, sodium, calcium and magnesium salts. Salts derived from pharmaceutically acceptable organic nontoxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particular organic nontoxic bases include isopropylamine, diethylamine, ethanolamine, tromethamine, dicyclohexylamine, choline, and caffeine.

In some embodiments, a salt is selected from a hydrochloride, hydrobromide, trifluoroacetate, sulphate, phosphate, acetate, fumarate, maleate, tartrate, lactate, citrate, pyruvate, succinate, oxalate, methanesulphonate, p-toluenesulphonate, bisulphate, benzenesulphonate, ethanesulphonate, malonate, xinafoate, ascorbate, oleate, nicotinate, saccharinate, adipate, formate, glycolate, palmitate, L-lactate, D-lactate, aspartate, malate, L-tartrate, D-tartrate, stearate, furoate (e.g., 2-furoate or 3-furoate), napadisylate (naphthalene-1,5-disulfonate or naphthalene-1-(sulfonic acid)-5-sulfonate), edisylate (ethane-1,2-disulfonate or ethane-1-(sulfonic acid)-2-sulfonate), isethionate (2-hydroxyethylsulfonate), 2-mesitylenesulphonate, 2-naphthalenesulphonate, 2,5-dichlorobenzenesulphonate, D-mandelate, L-mandelate, cinnamate, benzoate, adipate, esylate, malonate, mesitylate (2-mesitylenesulphonate), napsylate (2-naphthalenesulfonate), camsylate (camphor-10-sulphonate, for example (1S)-(+)-10-camphorsulfonic acid salt), glutamate, glutarate, hippurate (2-(benzoylamino)acetate), orotate, xylate (p-xylene-2-sulphonate), and pamoic (2,2'-dihydroxy-1,1'-dinaphthylmethane-3,3'-dicarboxylate).

A "sterile" formulation is aseptic or free from all living microorganisms and their spores.

"Stereoisomers" refer to compounds that have identical chemical constitution, but differ with regard to the arrangement of the atoms or groups in space. Stereoisomers include diastereomers, enantiomers, conformers and the like.

"Chiral" refers to molecules which have the property of non-superimposability of the mirror image partner, while the term "achiral" refers to molecules which are superimposable on their mirror image partner.

"Diastereomer" refers to a stereoisomer with two or more centers of chirality and whose molecules are not mirror images of one another. Diastereomers have different physical properties, e.g., melting points, boiling points, spectral properties or biological activities. Mixtures of diastereomers may separate under high resolution analytical procedures such as electrophoresis and chromatography such as HPLC.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Certain compounds of the invention can exist in unsolvated forms as well as solvated forms, including hydrated forms. A "solvate" refers to an association or complex of one or more solvent molecules and a compound of the present invention. Examples of solvents that form solvates include water, isopropanol, ethanol, methanol, DMSO, ethyl acetate, acetic acid, and ethanolamine. Certain compounds of the invention can exist in multiple crystalline or amorphous forms. In general, all physical forms are intended to be within the scope of the present invention. The term "hydrate" refers to the complex where the solvent molecule is water.

A "metabolite" refers to a product produced through metabolism in the body of a specified compound or salt thereof. Such products can result, for example, from the oxidation, reduction, hydrolysis, amidation, deamidation, esterification, deesterification, enzymatic cleavage, and the like, of the administered compound.

Metabolite products typically are identified by preparing a radiolabelled (e.g., $^{14}C$ or $^{3}H$) isotope of a compound of the invention, administering it in a detectable dose (e.g., greater than about 0.5 mg/kg) to an animal such as rat, mouse, guinea pig, monkey, or to a human, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

"Amino-protecting group" as used herein refers to a derivative of the groups commonly employed to block or protect an amino group while reactions are carried out on other functional groups on the compound. Examples of such protecting groups include carbamates, amides, alkyl and aryl groups, and imines, as well as many N-heteroatom derivatives which can be removed to regenerate the desired amine group. Particular amino protecting groups are Pmb (p-Methoxybenzyl), Boc (tert-Butyloxycarbonyl), Fmoc (9-Fluorenylmethyloxycarbonyl) and Cbz (Carbobenzyloxy). Further examples of these groups are found in T. W. Greene and P. G. M. Wuts, "Protecting Groups in Organic Synthesis, $3^{rd}$ ed., John Wiley & Sons, Inc., 1999. The term "protected amino" refers to an amino group substituted with one of the above amino-protecting groups.

"Carboxy-protecting group" as used herein refers to those groups that are stable to the conditions of subsequent reaction(s) at other positions of the molecule, which may be removed at the appropriate point without disrupting the remainder of the molecule, to give the unprotected carboxy-group. Examples of carboxy protecting groups include, ester groups and heterocyclyl groups. Ester derivatives of the carboxylic acid group may be employed to block or protect the carboxylic acid group while reactions are carried out on other functional groups on the compound. Examples of such ester groups include substituted arylalkyl, including substituted benzyls, such as 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, alkyl or substituted alkyl esters such as methyl, ethyl, t-butyl allyl or t-amyl, triphenylmethyl (trityl), 4-methoxytrityl, 4,4'-dimethoxytrityl, 4,4',4"-trimethoxytrityl, 2-phenylprop-2-yl, thioesters such as t-butyl thioester, silyl esters such as trimethylsilyl, t-butyldimethylsilyl esters, phenacyl, 2,2,2-trichloroethyl, beta-(trimethylsilyl)ethyl, beta-(di(n-butyl)methylsilyl)ethyl, p-toluenesulfonylethyl, 4-nitrobenzylsulfonylethyl, allyl, cinnamyl, 1-(trimethylsilylmethyl)prop-1-en-3-yl, and like moieties. Another example of carboxy-protecting groups are heterocyclyl groups such as 1,3-oxazolinyl. Further examples of these groups are found in T. W. Greene and P. G. M. Wuts, "Protecting Groups in Organic Synthesis, $3^{rd}$ ed., John Wiley & Sons, Inc., 1999. The term "protected carboxy" refers to a carboxy group substituted with one of the above carboxy-protecting groups.

"Hydroxy-protecting group" as used herein refers to a derivative of the hydroxy group commonly employed to block or protect the hydroxy group while reactions are carried out on other functional groups on the compound. Examples of such protecting groups include tetrahydropyranyloxy, benzoyl, acetoxy, carbamoyloxy, benzyl, and silyl ethers (e.g., TBS, TBDPS) groups. Further examples of these groups are found in T. W. Greene and P. G. M. Wuts, "Protecting Groups in Organic Synthesis, $3^{rd}$ ed., John Wiley & Sons, Inc., 1999. The term "protected hydroxy" refers to a hydroxy group substituted with one of the above hydroxy-protecting groups.

Compounds of the invention may contain one or more asymmetric carbon atoms. Accordingly, the compounds may exist as diastereomers, enantiomers or mixtures thereof. The syntheses of the compounds may employ racemates, diastereomers or enantiomers as starting materials or as intermediates. Mixtures of particular diastereomeric compounds may be separated, or enriched in one or more particular diastereomers, by chromatographic or crystallization methods. Similarly, enantiomeric mixtures may be separated, or enantiomerically enriched, using the same techniques or others known in the art. Each of the asymmetric carbon or nitrogen atoms may be in the R or S configuration and both of these configurations are within the scope of the invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined. Unless otherwise specified, if solid wedges or dashed lines are used, relative stereochemistry is intended.

Another aspect includes prodrugs of the compounds of the invention including known amino-protecting and carboxy-protecting groups which are released, for example hydrolyzed, to yield the compound of the present invention under physiologic conditions.

The term "prodrug" refers to a precursor or derivative form of a pharmaceutically active substance that is less efficacious to the patient compared to the parent drug and is capable of being enzymatically or hydrolytically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," Directed Drug Delivery, Borchardt et al., (ed.), pp. 247-267, Humana Press (1985). Prodrugs include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, and 5-fluorocytosine and 5-fluorouridine prodrugs.

A particular class of prodrugs are compounds in which a nitrogen atom in an amino, amidino, aminoalkyleneamino, iminoalkyleneamino or guanidino group is substituted with a hydroxy group, an alkylcarbonyl (—CO—R) group, an alkoxycarbonyl (—CO—OR), or an acyloxyalkyl-alkoxycarbonyl (—CO—O—R—O—CO—R) group where R is a monovalent or divalent group, for example alkyl, alkylene or aryl, or a group having the Formula —C(O)—O—CP1P2-haloalkyl, where P1 and P2 are the same or different and are hydrogen, alkyl, alkoxy, cyano, halogen, alkyl or aryl. In a particular embodiment, the nitrogen atom is one of the nitrogen atoms of the amidino group of the compounds of the invention. Prodrugs may be prepared by reacting a compound of the present invention with an activated group, such as acyl groups, to bond, for example, a nitrogen atom in the compound to the exemplary carbonyl of the activated acyl group. Examples of activated carbonyl compounds are those containing a leaving group bonded to the carbonyl group, and include, for example, acyl halides, acyl amines, acyl pyridinium salts, acyl alkoxides, acyl phenoxides such as p-nitrophenoxy acyl, dinitrophenoxy acyl, fluorophenoxy acyl, and difluorophenoxy acyl. The reactions are generally carried out in inert solvents at reduced temperatures such as −78 to about 50° C. The reactions may also be carried out in the presence of an inorganic base, for example potassium carbonate or sodium bicarbonate, or an organic base such as an amine, including pyridine, trimethylamine, triethylamine, triethanolamine, or the like.

Additional types of prodrugs are also encompassed. For instance, a free carboxyl group of a compound of the invention can be derivatized as an amide or alkyl ester. As another example, compounds of the invention comprising free hydroxy groups can be derivatized as prodrugs by converting the hydroxy group into a group such as, but not limited to, a phosphate ester, hemisuccinate, dimethylaminoacetate, or phosphoryloxymethyloxycarbonyl group, as outlined in Fleisher, D. et al., (1996) Improved oral drug delivery: solubility limitations overcome by the use of prodrugs Advanced Drug Delivery Reviews, 19:115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group can be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., (1996), 39:10. More specific examples include replacement of the hydrogen atom of the alcohol group with a group such as ($C_1$-$C_6$)alkanoyl oxymethyl, 1-(($C_1$-$C_6$) alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, alpha-amino($C_1$-$C_4$)alkanoyl, arylacyl and alpha-aminoacyl, or alpha-aminoacyl-alpha-aminoacyl, where each alpha-aminoacyl group is independently selected from the naturally occurring L-amino acids, $P(O)(OH)_2$, —$P(O)(O(C_1$-$C_6)$alkyl$)_2$ or glycosyl (the radical resulting from the removal of a hydroxyl group of the hemiacetal form of a carbohydrate).

"Leaving group" refers to a portion of a first reactant in a chemical reaction that is displaced from the first reactant in the chemical reaction. Examples of leaving groups include, but are not limited to, halogen atoms, alkoxy and sulfonyloxy groups. Example sulfonyloxy groups include, but are not limited to, alkylsulfonyloxy groups (for example methyl sulfonyloxy (mesylate group) and trifluoromethylsulfonyloxy (triflate group)) and arylsulfonyloxy groups (for example p-toluenesulfonyloxy (tosylate group) and p-nitrosulfonyloxy (nosylate group)).

A "subject," "individual," or "patient" is a vertebrate. In certain embodiments, the vertebrate is a mammal. Mammals include, but are not limited to, farm animals (such as cows), sport animals, pets (such as guinea pigs, cats, dogs, rabbits and horses), primates, mice and rats. In certain embodiments, a mammal is a human. In embodiments comprising administration of a compound of to a patient, the patient is typically in need thereof.

The term "Janus kinase" refers to JAK1, JAK2, JAK3 and TYK2 protein kinases. In some embodiments, a Janus kinase may be further defined as one of JAK1, JAK2, JAK3 or TYK2. In any embodiment, any one of JAK1, JAK2, JAK3 and TYK2 may be specifically excluded as a Janus kinase. In some embodiments, a Janus kinase is JAK1. In some embodiments, a Janus kinase is a combination of JAK1 and JAK2.

The terms "inhibiting" and "reducing," or any variation of these terms, includes any measurable decrease or complete inhibition to achieve a desired result. For example, there may be a decrease of about, at most about, or at least about 5%, 10%, 15%, 20%, 25%, 30%, 35%, 40%, 45%, 50%, 55%, 60%, 65%, 70%, 75%, 80%, 85%, 90%, 95%, 99%, or more, or any range derivable therein, reduction of activity (e.g., JAK1 activity) compared to normal.

In some embodiments, a compound of Formula (I) is selective for inhibition of JAK1 over JAK3 and TYK2. In some embodiments, a compound of Formula (I) is selective for inhibition of JAK1 over JAK2, JAK3, or TYK2, or any combination of JAK2, JAK3, or TYK2. In some embodiments, a compound of Formula (I) is selective for inhibition of JAK1 and JAK2 over JAK3 and TYK2. In some embodiments, a compound of Formula (I) is selective for inhibition of JAK1 over JAK3. By "selective for inhibition" it is meant that the compound is at least a 5%, 10%, 15%, 20%, 25%, 30%, 35%, 40%, 45%, 50%, 55%, 60%, 65%, 70%, 75%, 80%, 85%, 90%, 95%, 99%, or more, or any range derivable therein, better inhibitor of a particular Janus kinase (e.g., JAK1) activity compared to another particular Janus kinase (e.g., JAK3) activity, or is at least a 2-, 3-, 4-, 5-, 10-, 25-, 50-, 100-, 250-, or 500-fold better inhibitor of a particular Janus kinase (e.g., JAK1) activity compared to another particular Janus kinase (e.g., JAK3) activity.

"Therapeutically effective amount" means an amount of a compound of the present invention, such as a compound of Formula 0, I, Ia, Ib, Ic, Id, Ie, If, Ig or Il, or a compound of any of Examples 1-1 to 1-303, 2-1 to 2-486 or 3-1, that (i) treats or prevents the particular disease, condition or disorder, or (ii) attenuates, ameliorates or eliminates one or more symptoms of the particular disease, condition, or disorder, and optionally (iii) prevents or delays the onset of one or more symptoms of the particular disease, condition or disorder described herein. In some embodiments, the therapeutically effective amount is an amount sufficient to decrease or alleviate the symptoms of an autoimmune or inflammatory disease (e.g., asthma). In some embodiments, a therapeutically effective amount is an amount of a chemical entity described herein sufficient to significantly decrease the activity or number of B-cells. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; or relieve to some extent one or more of the symptoms associated with the cancer. To the extent the drug may prevent growth or kill existing cancer cells, it may be cytostatic or cytotoxic. For cancer therapy, efficacy can, for example, be measured by assessing the time to disease progression (TTP) or determining the response rate (RR).

"Treatment" (and variations such as "treat" or "treating") refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, stabilized (i.e., not worsening) state of disease, decreasing the rate of disease progression, amelioration or palliation of the disease state, prolonging survival as compared to expected survival if not receiving treatment and remission or improved prognosis. In some embodiments, compounds of the invention, are used to delay development of a disease or disorder or to slow the progression of a disease or disorder. Those in need of treatment include those already with the condition or disorder as well as those prone to have the condition or disorder, (for example, through a genetic mutation) or those in which the condition or disorder is to be prevented.

"Inflammatory disorder" refers to any disease, disorder or syndrome in which an excessive or unregulated inflammatory response leads to excessive inflammatory symptoms, host tissue damage, or loss of tissue function. "Inflammatory disorder" also refers to a pathological state mediated by influx of leukocytes or neutrophil chemotaxis.

"Inflammation" refers to a localized, protective response elicited by injury or destruction of tissues, which serves to destroy, dilute, or wall off (sequester) both the injurious agent and the injured tissue. Inflammation is notably associated with influx of leukocytes or neutrophil chemotaxis. Inflammation can result from infection with pathogenic organisms and viruses and from noninfectious means such as trauma or reperfusion following myocardial infarction or stroke, immune responses to foreign antigens, and autoimmune responses. Accordingly, inflammatory disorders amenable to treatment with a compound of the present invention, such as a compound of Formula 0, I, Ia, Ib, Ic, Id, Ie, If, Ig or Il, or a compound of any of Examples 1-1 to 1-303, 2-1 to 2-486 or 3-1, encompass disorders associated with reactions of the specific defense system as well as with reactions of the nonspecific defense system.

"Specific defense system" refers to the component of the immune system that reacts to the presence of specific antigens. Examples of inflammation resulting from a response of the specific defense system include the classical response to foreign antigens, autoimmune diseases, and delayed type hypersensitivity responses mediated by T-cells. Chronic inflammatory diseases, the rejection of solid transplanted tissue and organs, e.g., kidney and bone marrow transplants, and graft versus host disease (GVHD), are further examples of inflammatory reactions of the specific defense system.

The term "nonspecific defense system" refers to inflammatory disorders that are mediated by leukocytes that are incapable of immunological memory (e.g., granulocytes, and macrophages). Examples of inflammation that result, at least in part, from a reaction of the nonspecific defense system include inflammation associated with conditions such as adult (acute) respiratory distress syndrome (ARDS) or multiple organ injury syndromes; reperfusion injury; acute glomerulonephritis; reactive arthritis; dermatoses with acute inflammatory components; acute purulent meningitis or other central nervous system inflammatory disorders such as stroke; thermal injury; inflammatory bowel disease; granulocyte transfusion associated syndromes; and cytokine-induced toxicity.

"Autoimmune disease" refers to any group of disorders in which tissue injury is associated with humoral or cell-mediated responses to the body's own constituents. Non-limiting examples of autoimmune diseases include rheumatoid arthritis, lupus and multiple sclerosis.

"Allergic disease" as used herein refers to any symptoms, tissue damage, or loss of tissue function resulting from allergy. "Arthritic disease" as used herein refers to any disease that is characterized by inflammatory lesions of the joints attributable to a variety of etiologies. "Dermatitis" as used herein refers to any of a large family of diseases of the skin that are characterized by inflammation of the skin attributable to a variety of etiologies. "Transplant rejection" as used herein refers to any immune reaction directed against grafted tissue, such as organs or cells (e.g., bone marrow), characterized by a loss of function of the grafted and surrounding tissues, pain, swelling, leukocytosis, and thrombocytopenia. The therapeutic methods of the present invention include methods for the treatment of disorders associated with inflammatory cell activation.

"Inflammatory cell activation" refers to the induction by a stimulus (including, but not limited to, cytokines, antigens or auto-antibodies) of a proliferative cellular response, the production of soluble mediators (including but not limited to cytokines, oxygen radicals, enzymes, prostanoids, or vasoactive amines), or cell surface expression of new or increased numbers of mediators (including, but not limited to, major histocompatability antigens or cell adhesion molecules) in inflammatory cells (including but not limited to monocytes, macrophages, T lymphocytes, B lymphocytes, granulocytes (i.e., polymorphonuclear leukocytes such as neutrophils, basophils, and eosinophils), mast cells, dendritic cells, Langerhans cells, and endothelial cells). It will be appreciated by persons skilled in the art that the activation of one or a combination of these phenotypes in these cells can contribute to the initiation, perpetuation, or exacerbation of an inflammatory disorder.

In some embodiments, inflammatory disorders which can be treated according to the methods of this invention include, but are not limited to, asthma, rhinitis (e.g., allergic rhinitis), allergic airway syndrome, atopic dermatitis, bronchitis, rheumatoid arthritis, psoriasis, contact dermatitis, chronic obstructive pulmonary disease and delayed hypersensitivity reactions.

The terms "cancer" and "cancerous", "neoplasm", and "tumor" and related terms refer to or describe the physiological condition in mammals that is typically characterized by unregulated cell growth. A "tumor" comprises one or more cancerous cells. Examples of cancer include carcinoma, blastoma, sarcoma, seminoma, glioblastoma, melanoma, leukemia, and myeloid or lymphoid malignancies. More particular examples of such cancers include squamous cell cancer (e.g., epithelial squamous cell cancer) and lung cancer including small-cell lung cancer, non-small cell lung cancer ("NSCLC"), adenocarcinoma of the lung and squamous carcinoma of the lung. Other cancers include skin, keratoacanthoma, follicular carcinoma, hairy cell leukemia, buccal cavity, pharynx (oral), lip, tongue, mouth, salivary gland, esophageal, larynx, hepatocellular, gastric, stomach, gastrointestinal, small intestine, large intestine, pancreatic, cervical, ovarian, liver, bladder, hepatoma, breast, colon, rectal, colorectal, genitourinary, biliary passage, thyroid, papillary, hepatic, endometrial, uterine, salivary gland, kidney or renal, prostate, testis, vulval, peritoneum, anal, penile, bone, multiple myeloma, B-cell lymphoma, central nervous system, brain, head and neck, Hodgkin's, and associated metastases. Examples of neoplastic disorders include myeloproliferative disorders, such as polycythemia vera, essential thrombocytosis, myelofibrosis, such as primary myelofibrosis, and chronic myelogenous leukemia (CML).

A "chemotherapeutic agent" is an agent useful in the treatment of a given disorder, for example, cancer or inflammatory disorders. Examples of chemotherapeutic agents are well-known in the art and include examples such as those disclosed in U.S. Publ. Appl. No. 2010/0048557, incorporated herein by reference. Additionally, chemotherapeutic agents include pharmaceutically acceptable salts, acids or derivatives of any of chemotherapeutic agents, as well as combinations of two or more of them.

"Package insert" is used to refer to instructions customarily included in commercial packages of therapeutic products that contain information about the indications, usage, dosage, administration, contraindications or warnings concerning the use of such therapeutic products.

Unless otherwise stated, structures depicted herein are also meant to include compounds that differ only in the presence of one or more isotopically enriched atoms. Exemplary isotopes that can be incorporated into compounds of the invention, include isotopes of hydrogen, carbon, nitrogen, oxygen, phosphorus, sulfur, fluorine, chlorine, and iodine, such as $^2$H, $^3$H, $^{11}$C, $^{13}$C, $^{14}$C, $^{13}$N, $^{15}$N, $^{15}$O, $^{17}$O, $^{18}$O, $^{32}$P, $^{33}$P, $^{35}$S, $^{18}$F, $^{36}$Cl, $^{123}$I, and $^{125}$I, respectively. Isotopically-labeled compounds (e.g., those labeled with $^3$H and $^{14}$C) can be useful in compound or substrate tissue distribution assays. Tritiated (i.e., $^3$H) and carbon-14 (i.e., $^{14}$C) isotopes can be useful for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements). In some embodiments, in compounds of the invention, one or more carbon atoms are replaced by $^{13}$C- or $^{14}$C-enriched carbon. Positron emitting isotopes such as $^{15}$O, $^{13}$N, $^{11}$C, and $^{18}$F are useful for positron emission tomography (PET) studies to examine substrate receptor occupancy. Isotopically labeled compounds can generally be prepared by following procedures analogous to those disclosed in the Schemes or in the Examples herein, by substituting an isotopically labeled reagent for a non-isotopically labeled reagent.

It is specifically contemplated that any limitation discussed with respect to one embodiment of the invention may apply to any other embodiment of the invention. Furthermore, any compound or composition of the invention may be used in any method of the invention, and any method of the invention may be used to produce or to utilize any compound or composition of the invention.

The use of the term "or" is used to mean "and/or" unless explicitly indicated to refer to alternatives only or the alternative are mutually exclusive, although the disclosure supports a definition that refers to only alternatives and "and/or."

Throughout this application, the term "about" is used to indicate that a value includes the standard deviation of error for the device or method being employed to determine the value.

As used herein, "a" or "an" means one or more, unless clearly indicated otherwise. As used herein, "another" means at least a second or more.

Headings used herein are intended only for organizational purposes.

Inhibitors of Janus Kinases

Also provided is a compound selected from Examples 1-13, and salts thereof.

In one embodiment R$^1$ is —(C$_0$-C$_3$alkyl)NR$^a$R$^b$.
In one embodiment R$^1$ is H or —(C$_0$-C$_3$alkyl)R$^a$.
In one embodiment R$^1$ is —(C$_0$-C$_3$alkyl)C(O)R$^a$.
In one embodiment R$^1$ is selected from the group consisting of H, methyl,

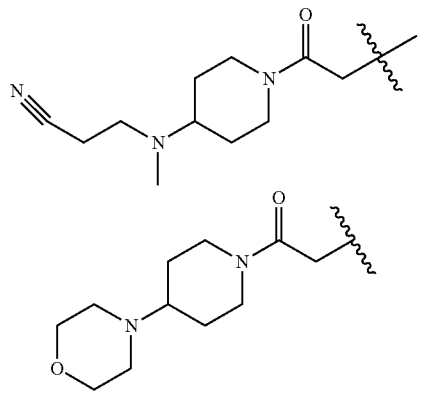

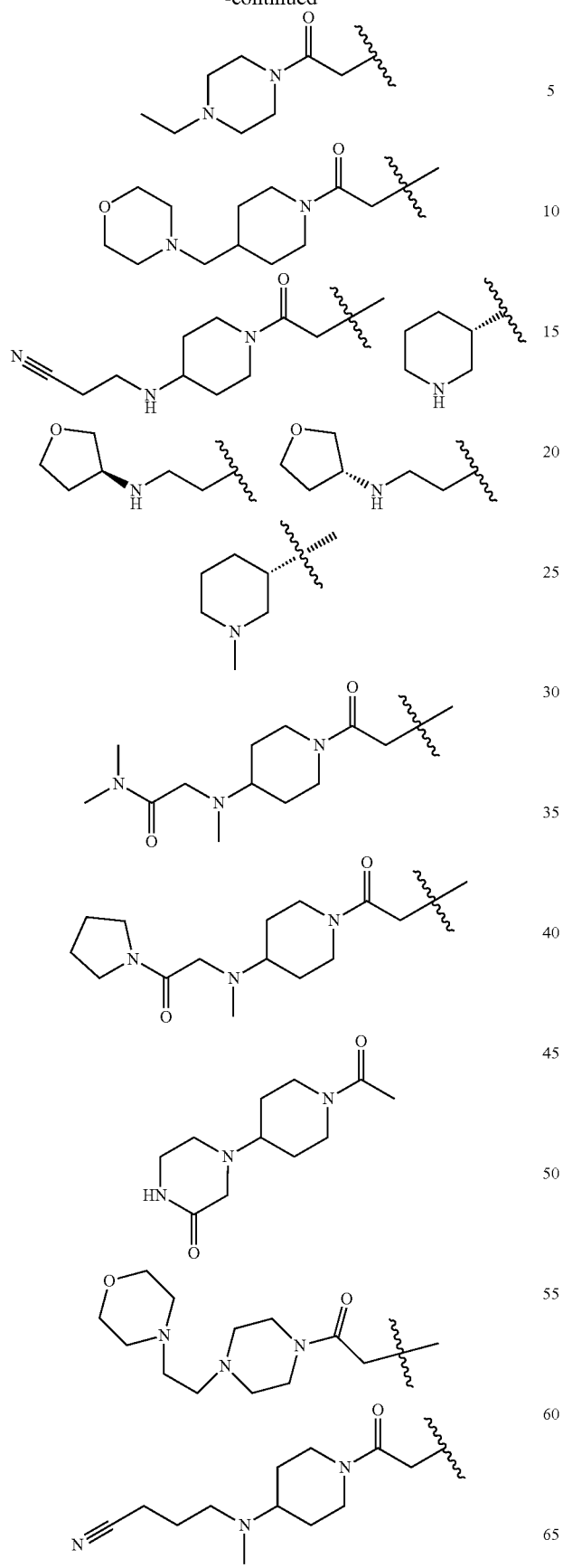
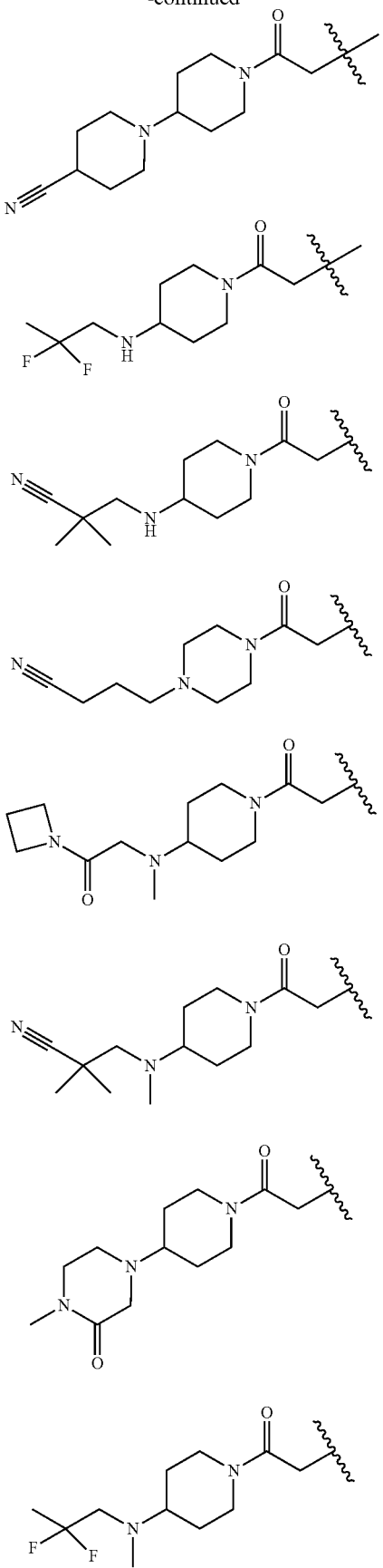

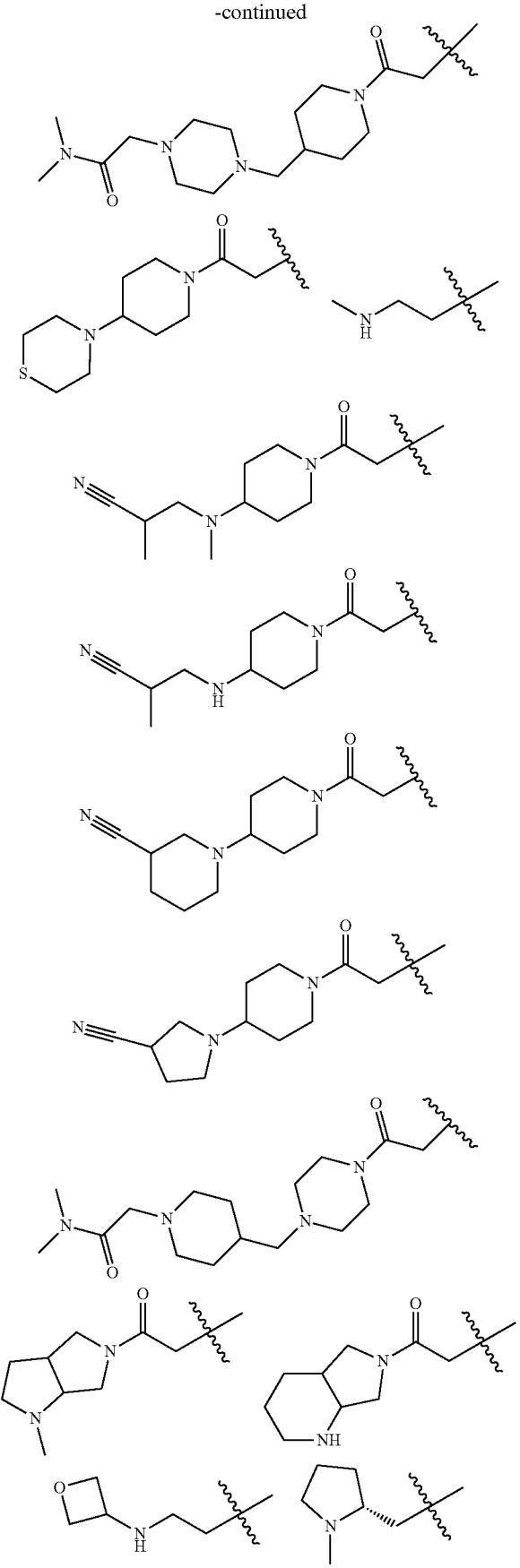
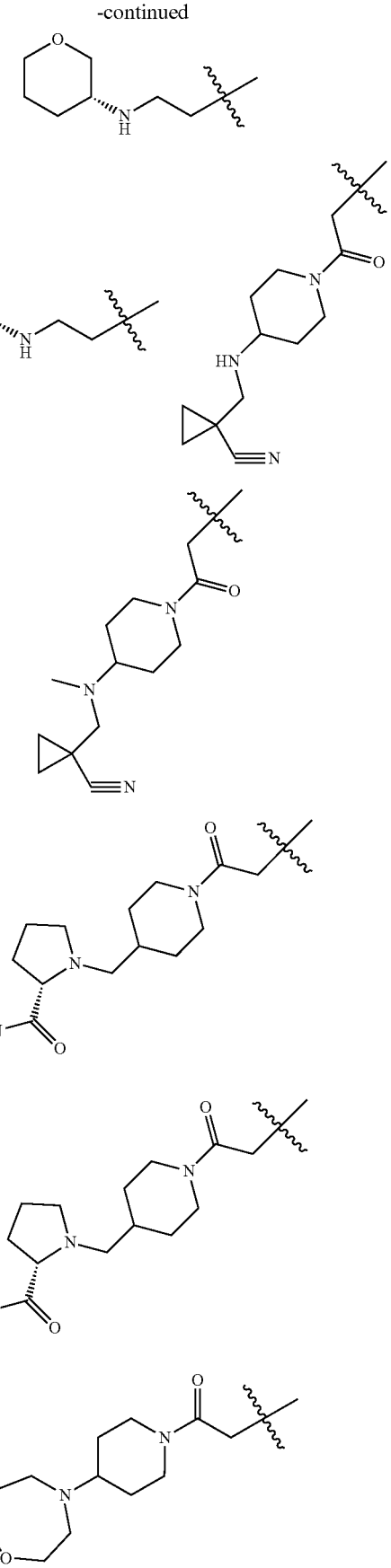

25
-continued
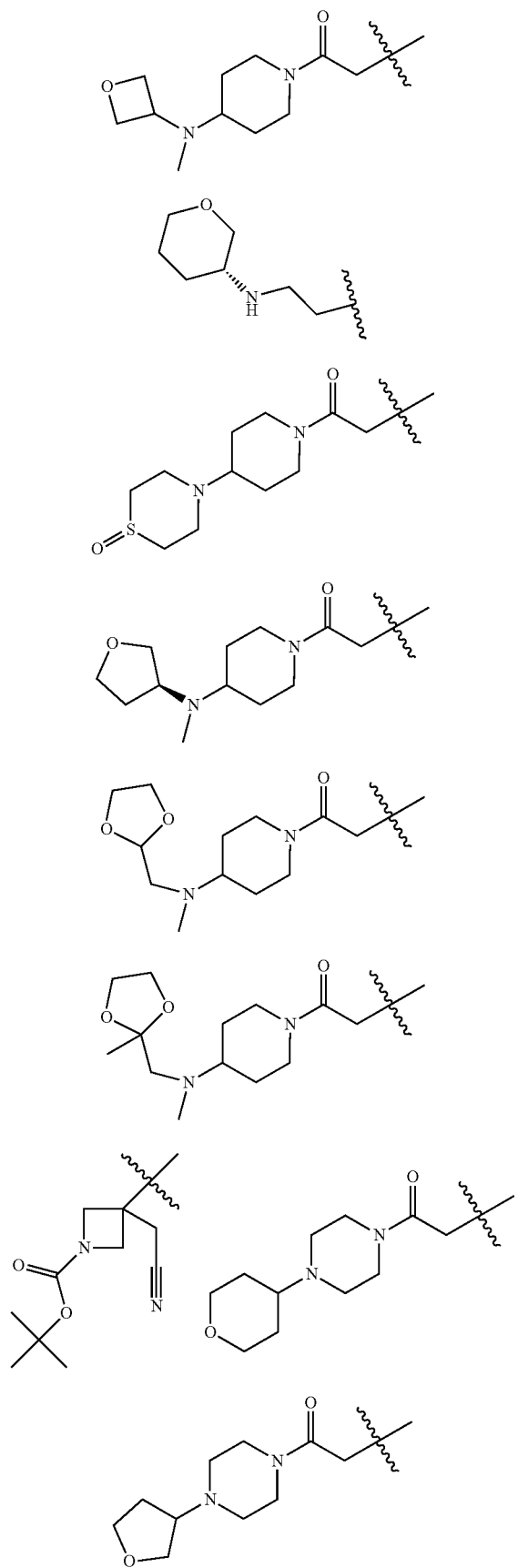
26
-continued
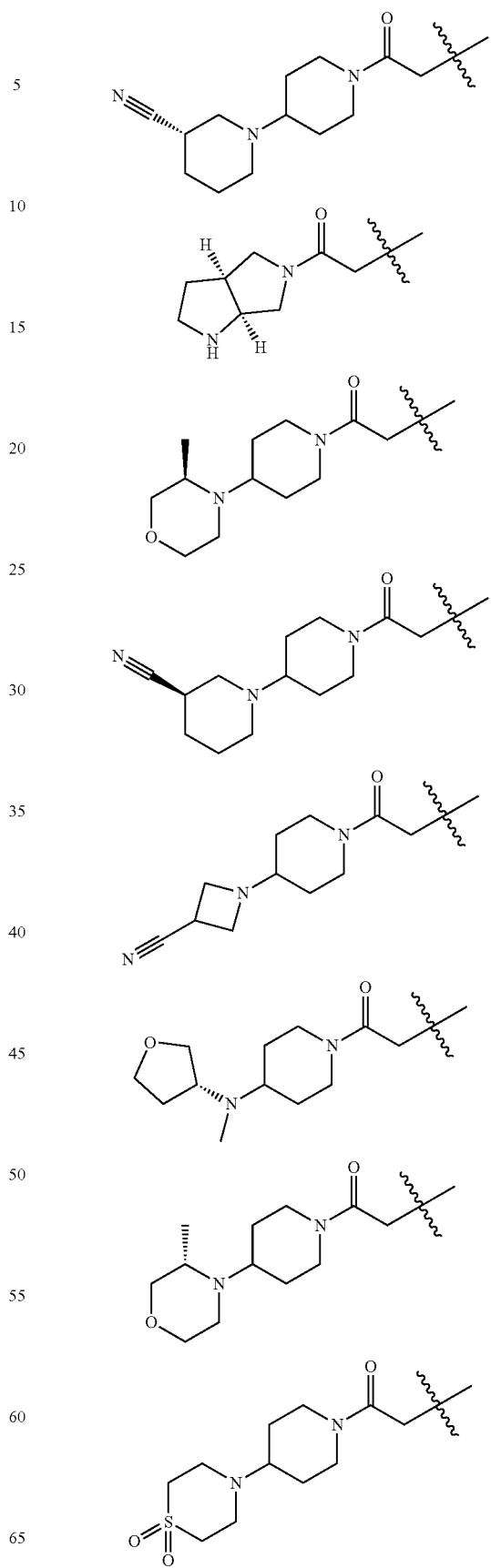

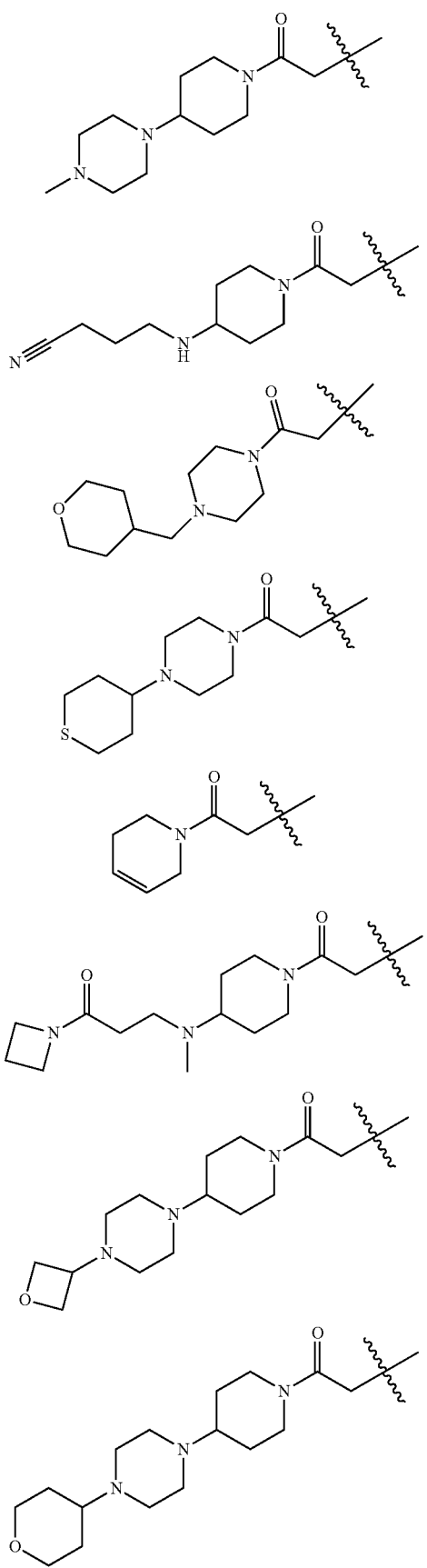
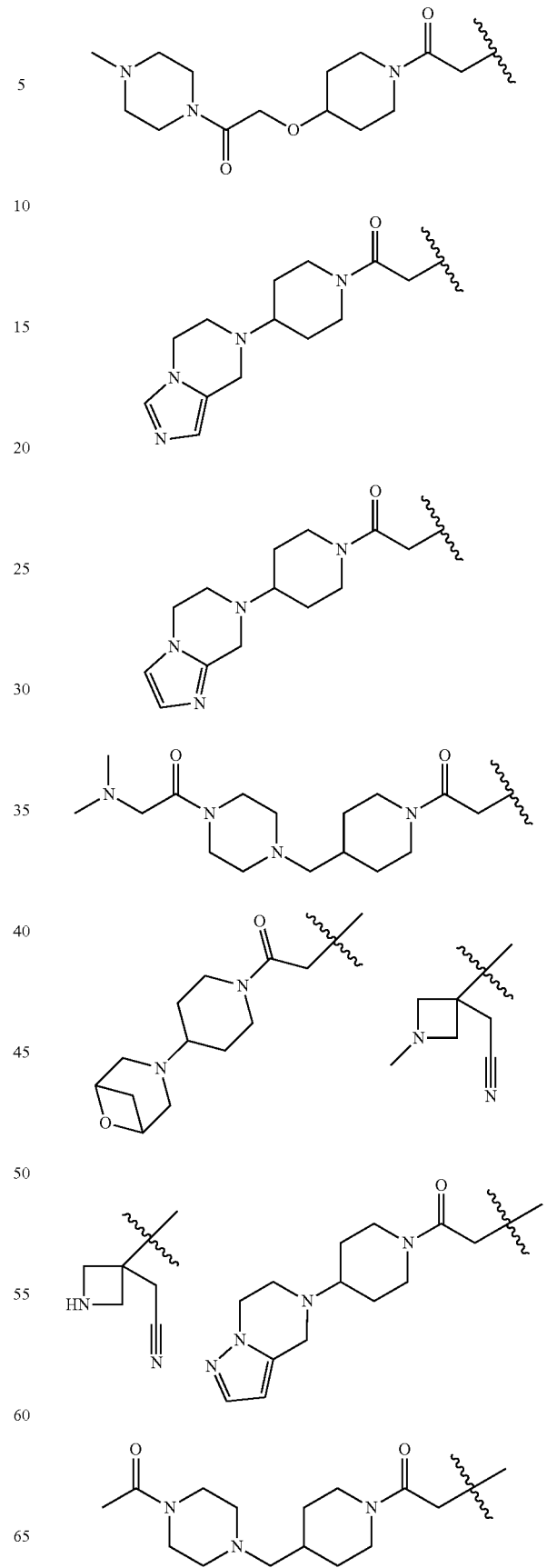

29
-continued
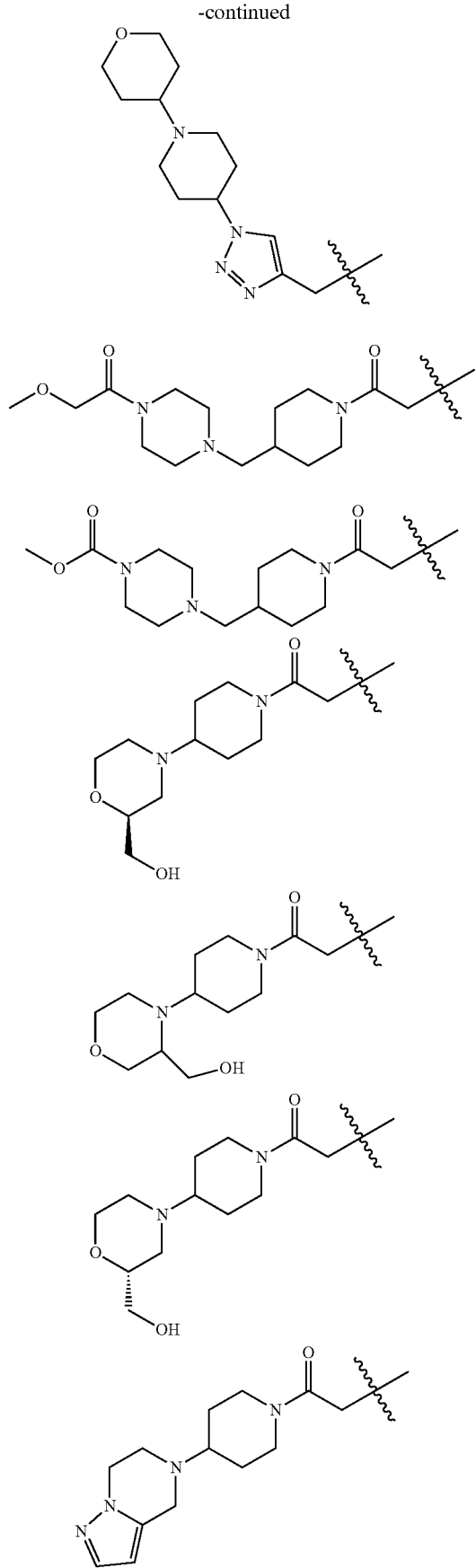
30
-continued
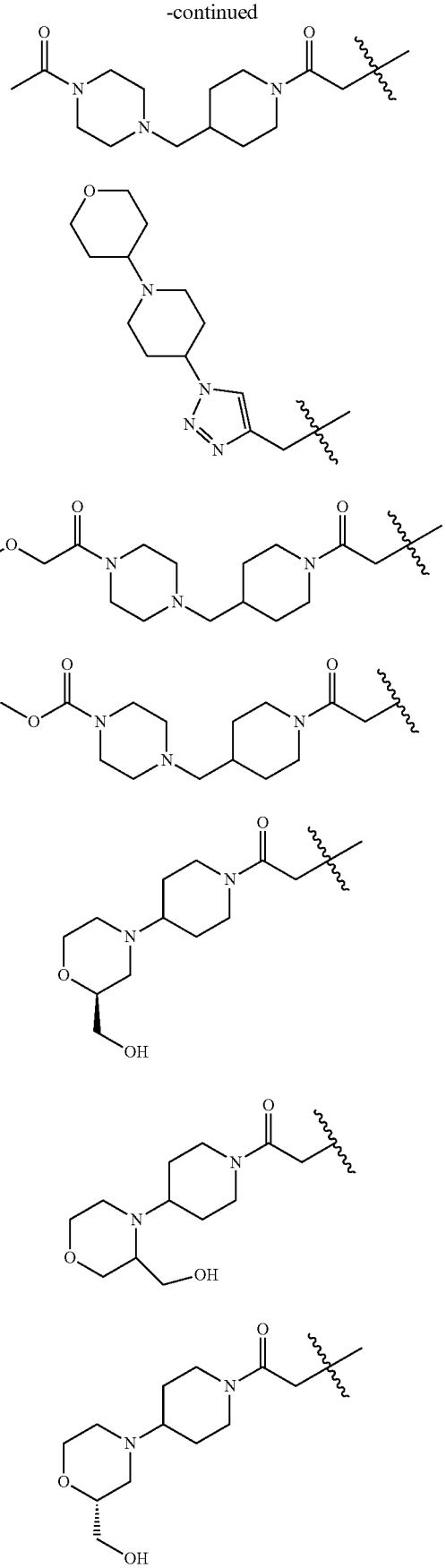

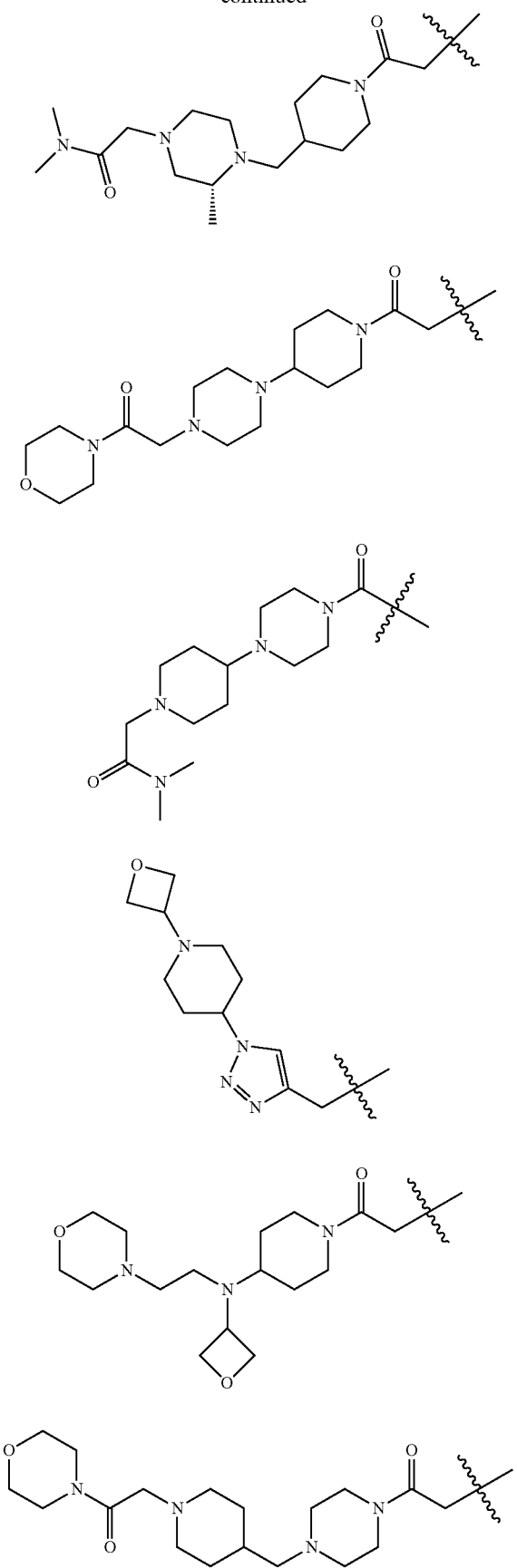
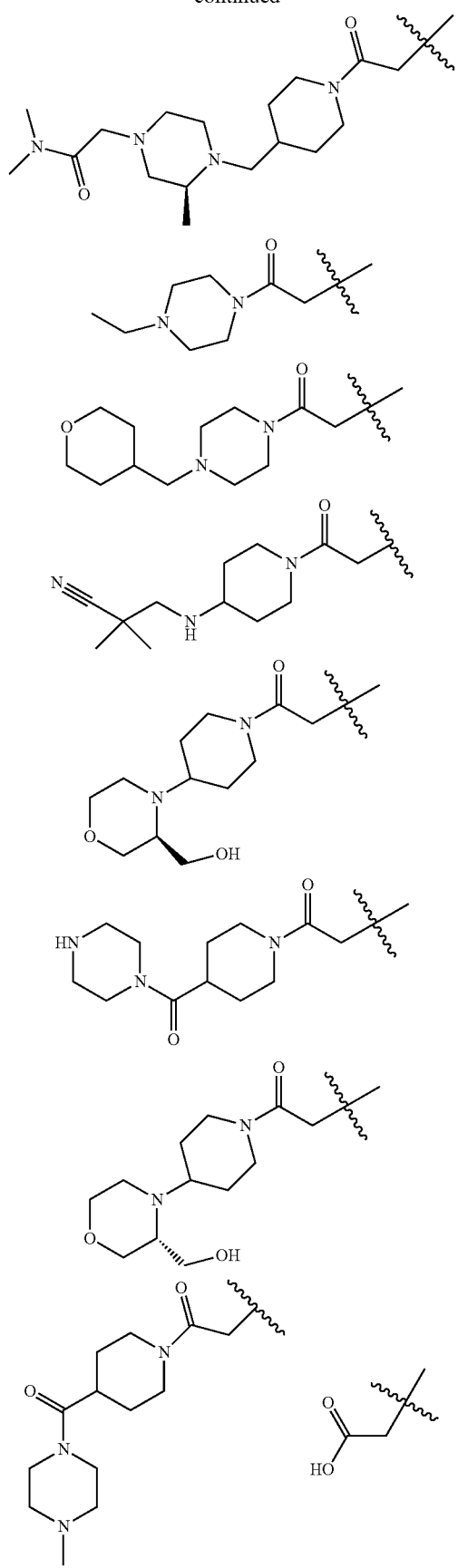

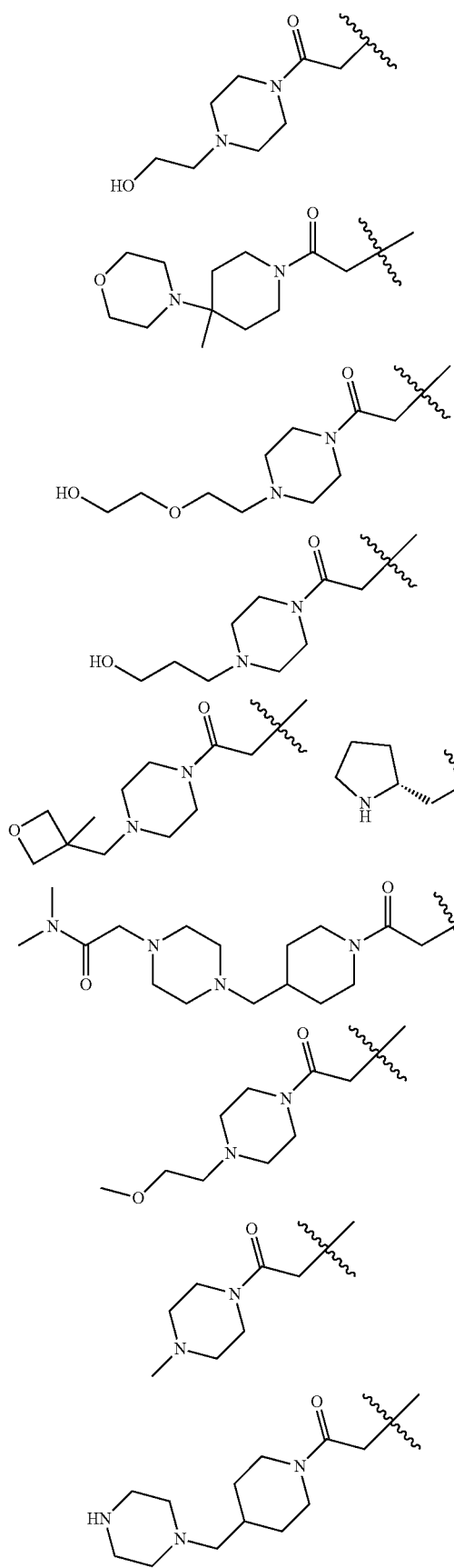
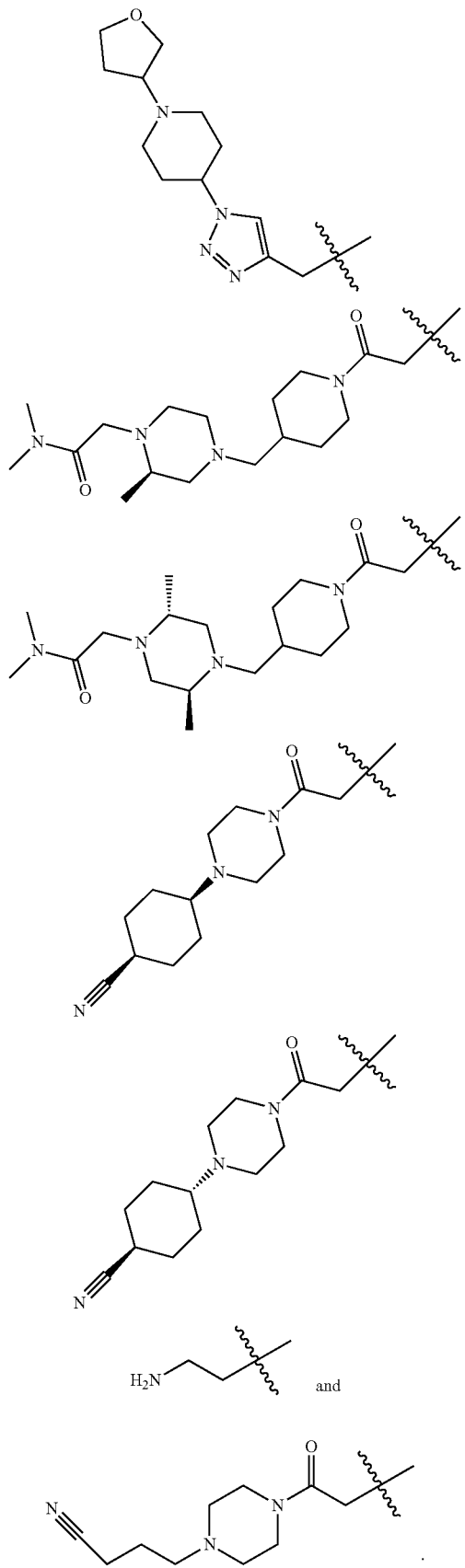

In one embodiment $R^1$ is H, methyl,
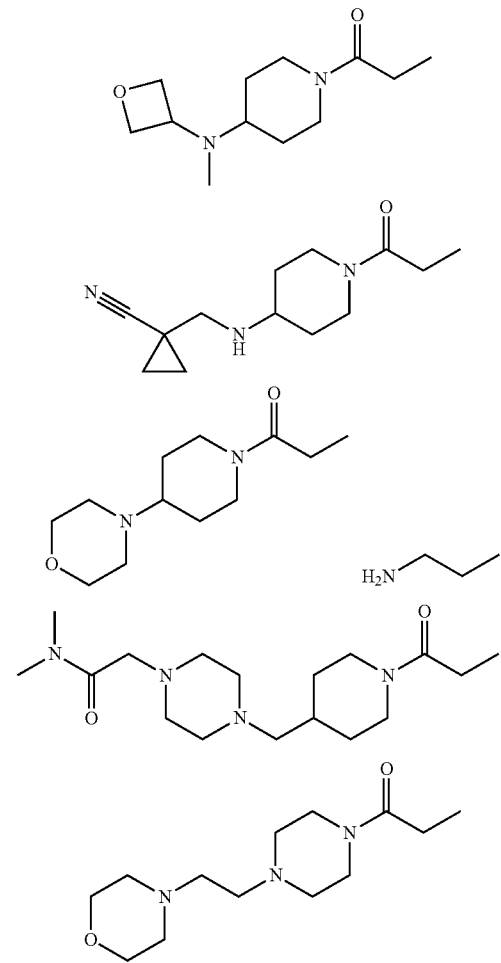
or
In one embodiment $R^e$ is selected from the group consisting of methyl, ethyl,
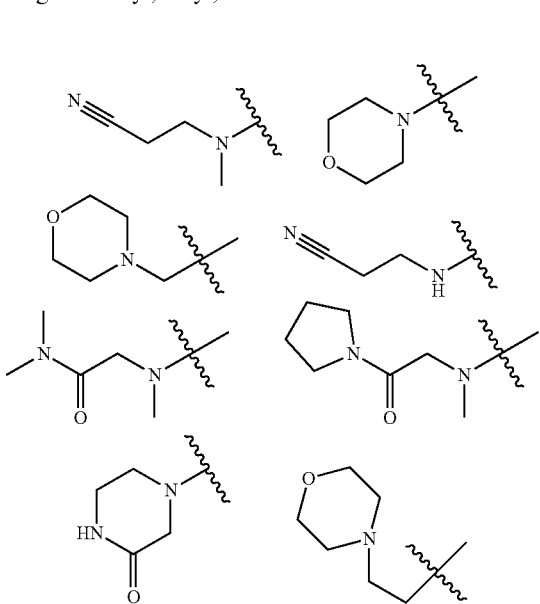
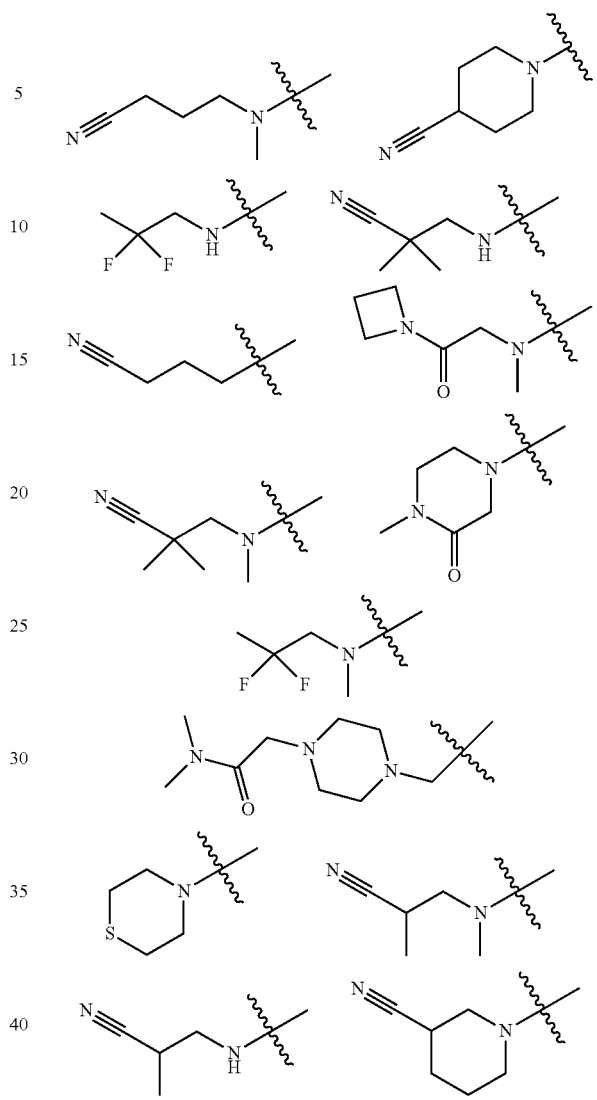

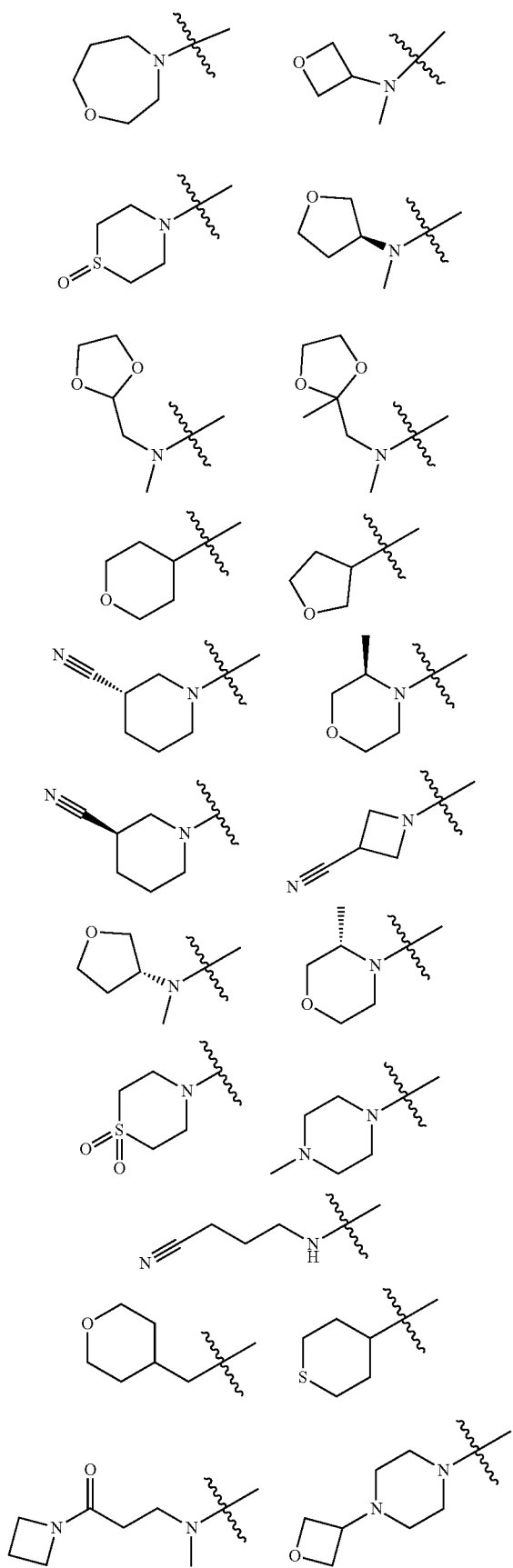
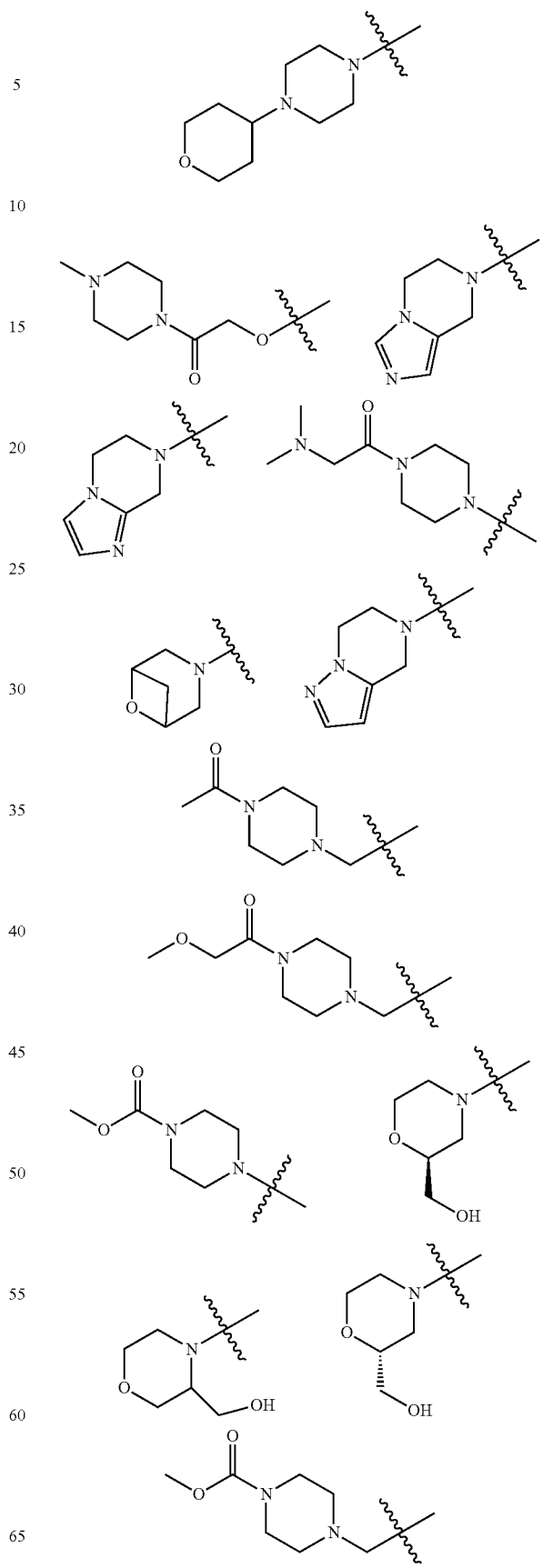

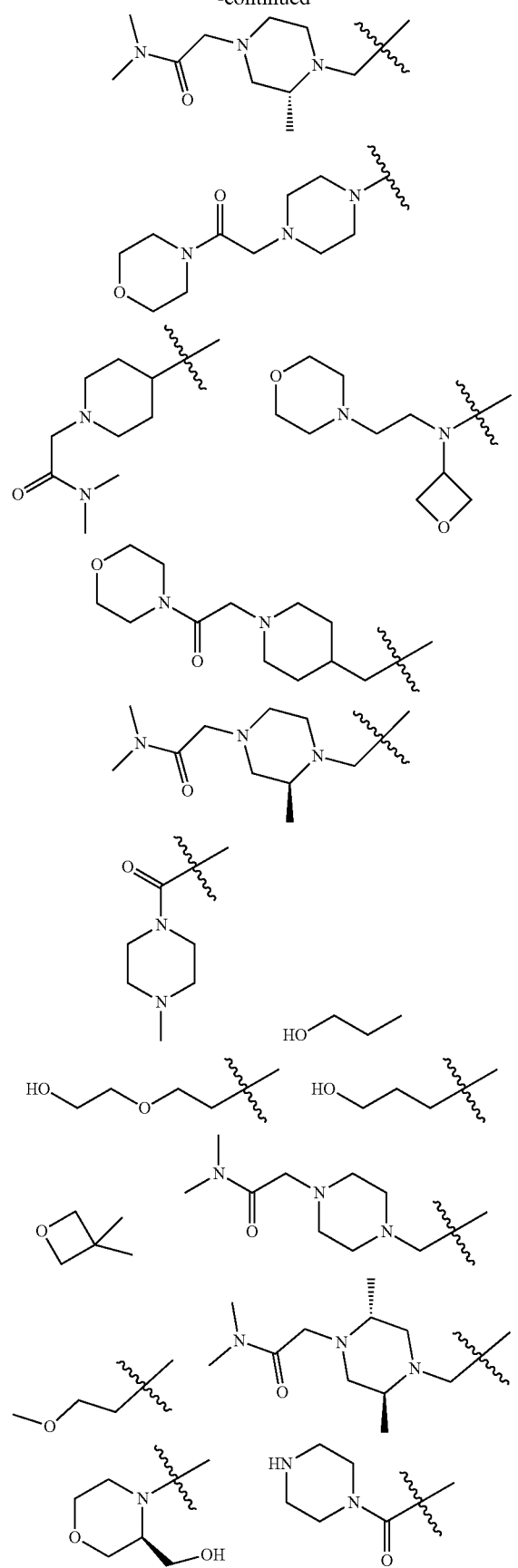
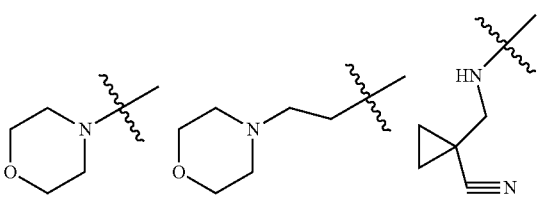
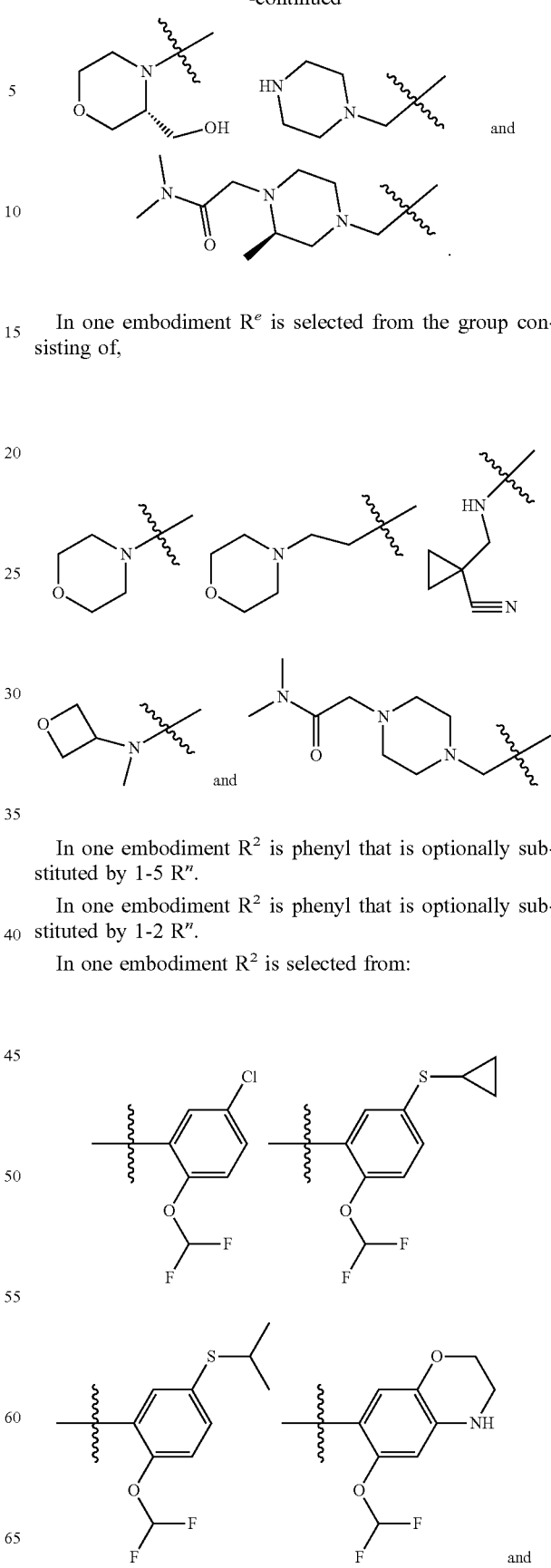
In one embodiment $R^e$ is selected from the group consisting of,
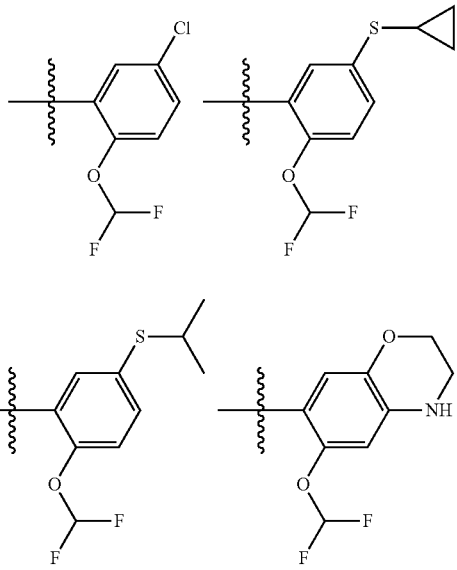
In one embodiment $R^2$ is phenyl that is optionally substituted by 1-5 $R''$.
In one embodiment $R^2$ is phenyl that is optionally substituted by 1-2 $R''$.
In one embodiment $R^2$ is selected from:

-continued

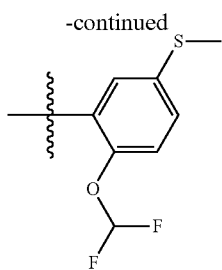

In one embodiment R³ is H.
In one embodiment R⁴ is H.
In one embodiment R⁵ is H, chloro, or ethynyl.
In one embodiment R³ is H, R⁴ is H, and R⁵ is H.
In one embodiment R³ is H, R⁴ is H, and R⁵ is chloro.
In one embodiment R³ is H, R⁴ is H, and R⁵ is ethynyl.
In one embodiment, R³ is —NH₂. In another embodiment, R³ is not —NH₂.

Exemplary Compounds of the invention include compounds selected from the group consisting of:

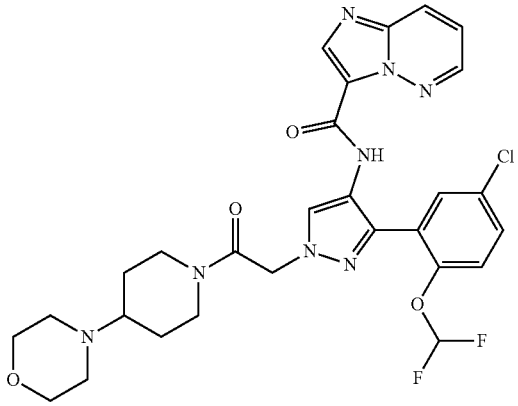

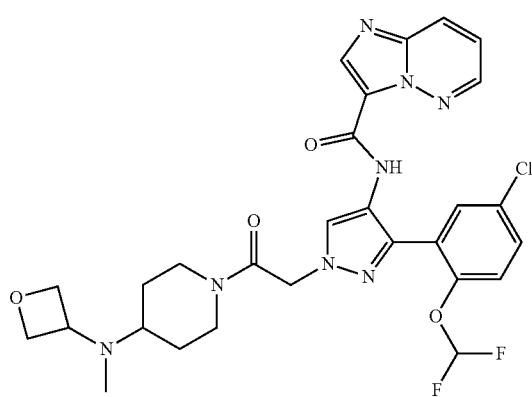

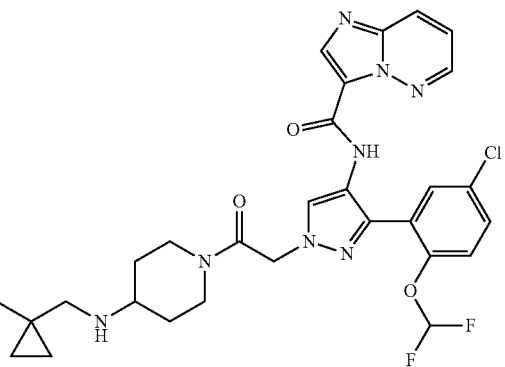

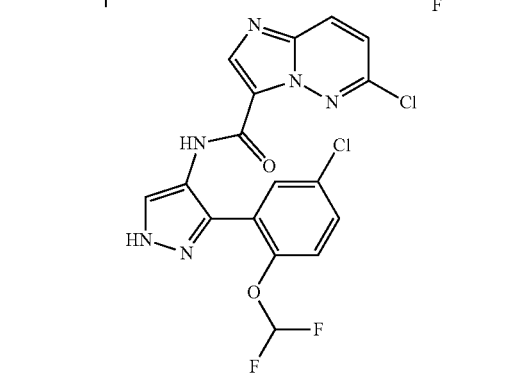

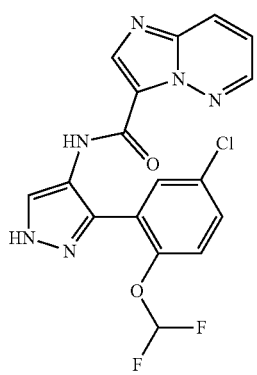

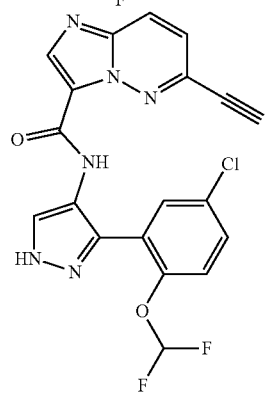

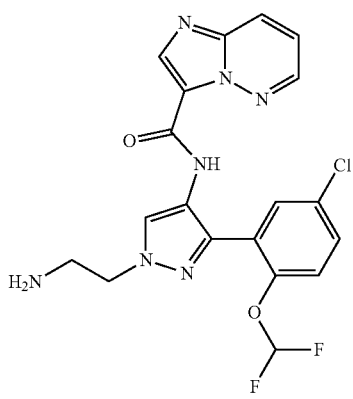

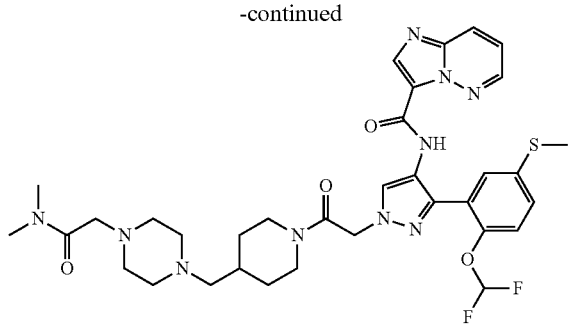

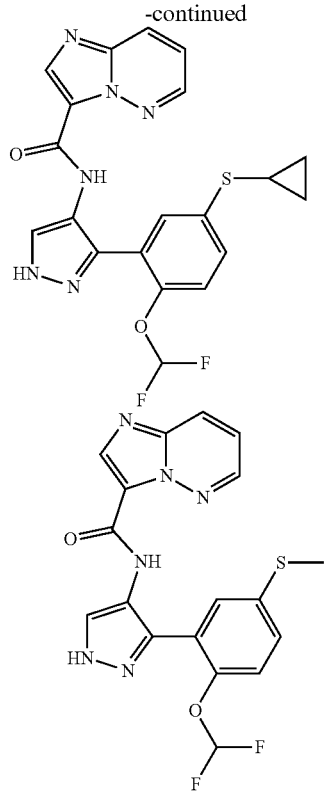

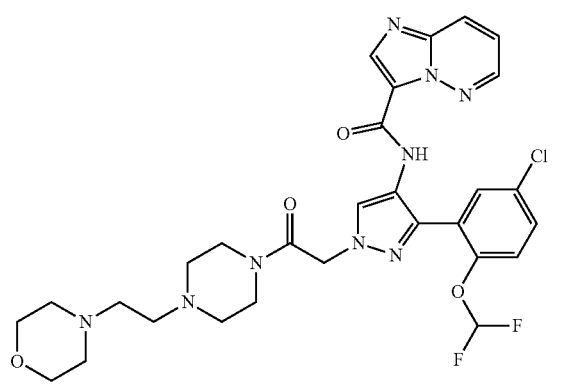

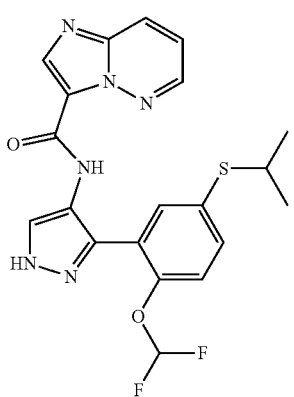

and salts thereof.

Also provided is a compound of the following formula, which can be prepared following methodologies similar to those provided herein combined with the knowledge of one skilled in the art.

In one embodiment the disease or condition is cancer, polycythemia vera, essential thrombocytosis, myelofibrosis, chronic myelogenous leukemia (CML), rheumatoid arthritis, inflammatory bowel syndrome, Crohn's disease, psoriasis, contact dermatitis or delayed hypersensitivity reactions.

In one embodiment the use of a compound of formula (I) or a pharmaceutically acceptable salt thereof, for the treatment of cancer, polycythemia vera, essential thrombocytosis, myelofibrosis, chronic myelogenous leukemia (CML), rheumatoid arthritis, inflammatory bowel syndrome, Crohn's disease, psoriasis, contact dermatitis or delayed hypersensitivity reactions is provided.

In one embodiment a composition that is formulated for administration by inhalation is provided.

In one embodiment a metered dose inhaler that comprises a compound of formula (I) or a pharmaceutically acceptable salt thereof is provided.

In one embodiment the compound of formula (I) or the pharmaceutically acceptable salt thereof is at least five-times more potent as an inhibitor of JAK1 than as an inhibitor of JAK2.

In one embodiment the compound of formula (I) or the pharmaceutically acceptable salt thereof is at least ten-times more potent as an inhibitor of JAK1 than as an inhibitor of JAK2.

In one embodiment the compound of formula (I) or the pharmaceutically acceptable salt thereof is at least five-times more potent as an inhibitor of JAK1 than as an inhibitor of JAK3.

In one embodiment the compound of formula (I) or the pharmaceutically acceptable salt thereof is at least ten-times more potent as an inhibitor of JAK1 than as an inhibitor of JAK3.

In one embodiment a method for treating hair loss in a mammal comprising administering a compound of formula (I) or a pharmaceutically acceptable salt thereof to the mammal is provided.

In one embodiment the use of a compound of formula (I) or a pharmaceutically acceptable salt thereof for the treatment of hair loss is provided.

In one embodiment the use of a compound of formula (I) or a pharmaceutically acceptable salt thereof to prepare a medicament for treating hair loss in a mammal is provided.

Synthesis of Janus Kinase Inhibitor Compounds

Compounds of the invention may be synthesized by synthetic routes described herein. In certain embodiments, processes well-known in the chemical arts can be used, in addition to, or in light of, the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, Reagents for Organic Synthesis, v. 1-19, Wiley, N.Y. (1967-1999 ed.), Beilsteins Handbuch der organischen Chemie, 4, Aufl. ed. Springer-Verlag, Berlin, including supplements (also available via the Beilstein online database)), or Comprehensive Heterocyclic Chemistry, Editors Katrizky and Rees, Pergamon Press, 1984.

Compounds may be prepared singly or as compound libraries comprising at least 2, for example 5 to 1,000 compounds, or 10 to 100 compounds. Libraries of compounds may be prepared by a combinatorial 'split and mix' approach or by multiple parallel syntheses using either solution phase or solid phase chemistry, by procedures known to those skilled in the art. Thus according to a further aspect of the invention there is provided a compound library comprising at least 2 compounds of the invention, such as a compound of Formula 0, I, Ia, Ib, Ic, Id, Ie, If, Ig or Il, or a compound of any of Examples 1-1 to 1-303, 2-1 to 2-486 or 3-1.

For illustrative purposes, reaction Schemes below provide routes for synthesizing the compounds of the invention as well as key intermediates. For a more detailed description of the individual reaction steps, see the Examples section below. Those skilled in the art will appreciate that other synthetic routes may be used. Although some specific starting materials and reagents are depicted in the Schemes and discussed below, other starting materials and reagents can be substituted to provide a variety of derivatives or reaction conditions. In addition, many of the compounds prepared by the methods described below can be further modified in light of this disclosure using conventional chemistry well known to those skilled in the art.

In the preparation of compounds of the invention, protection of remote functionality (e.g., primary or secondary amine) of intermediates may be necessary. The need for such protection will vary depending on the nature of the remote functionality and the conditions of the preparation methods. Suitable amino-protecting groups include acetyl, trifluoroacetyl, benzyl, phenylsulfonyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

Other conversions commonly used in the synthesis of compounds of the invention, and which can be carried out using a variety of reagents and conditions, include the following:

(1) Reaction of a carboxylic acid with an amine to form an amide. Such a transformation can be achieved using various reagents known to those skilled in the art but a comprehensive review can be found in *Tetrahedron*, 2005, 61, 10827-10852.

(2) Reaction of a primary or secondary amine with an aryl halide or pseudo halide, e.g., a triflate, commonly known as a "Buchwald-Hartwig cross-coupling," can be achieved using a variety of catalysts, ligands and bases. A review of these methods is provided in *Comprehensive Organic Name Reactions and Reagents*, 2010, 575-581.

(3) A palladium cross-coupling reaction between an aryl halide and a vinyl boronic acid or boronate ester. This transformation is a type of "Suzuki-Miyaura cross-coupling," a class of reaction that has been thoroughly reviewed in *Chemical Reviews*, 1995, 95(7), 2457-2483.

(4) The hydrolysis of an ester to give the corresponding carboxylic acid is well known to those skilled in the art and conditions include: for methyl and ethyl esters, the use of a strong aqueous base such as lithium, sodium or potassium hydroxide or a strong aqueous mineral acid such as HCl; for a tert-butyl ester, hydrolysis would be carried out using acid, for example, HCl in dioxane or trifluoroacetic acid (TFA) in dichloromethane (DCM).

Scheme 1
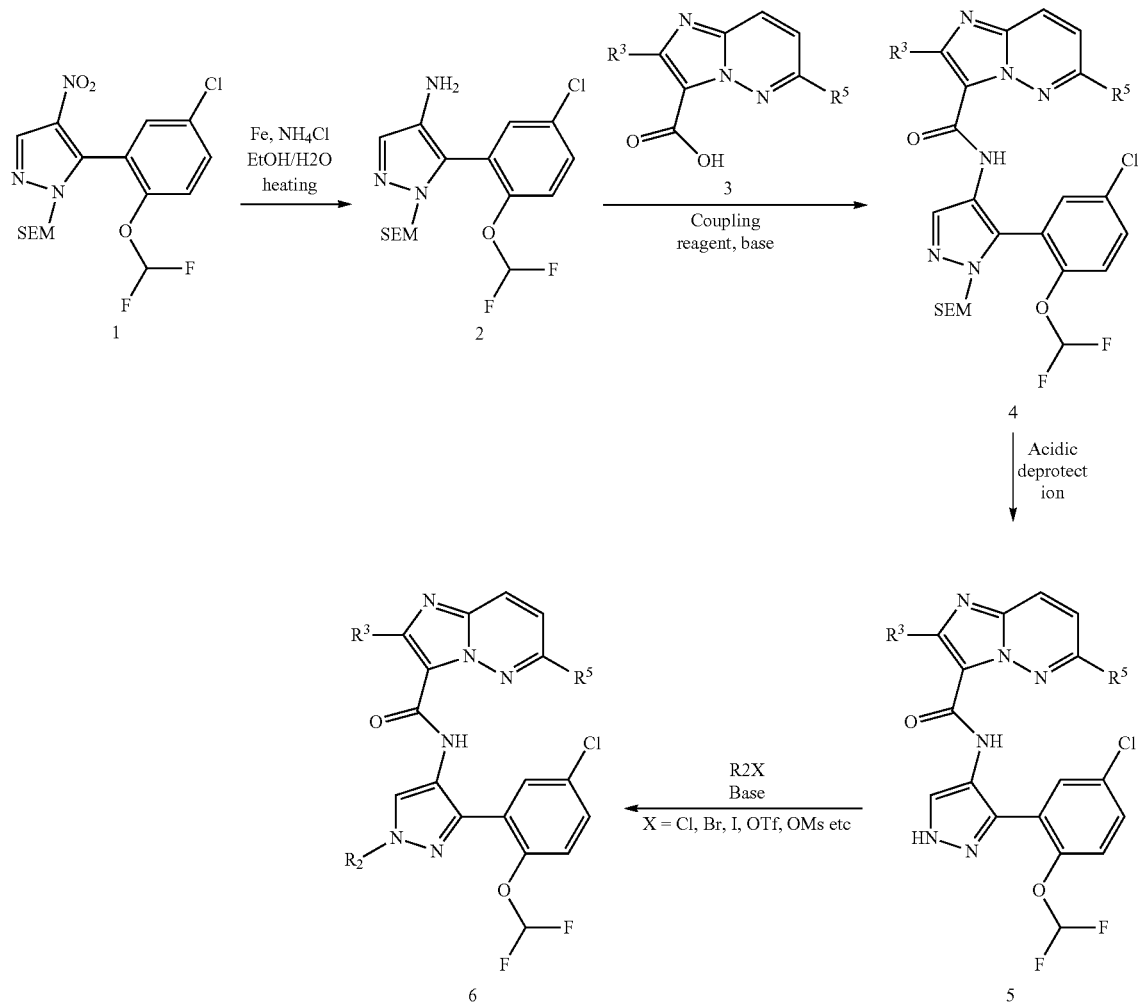
As shown in Scheme 1, compounds of type 2 may be accessed from compound of type 1 by nitro reduction. Amide bond formation between 2 and 3 provides compounds of type 4, which may then be deprotected under acidic conditions to yield compounds of type 5. Pyrazole alkylation with an appropriate electrophile and base provides compounds of type 6.
Scheme 2
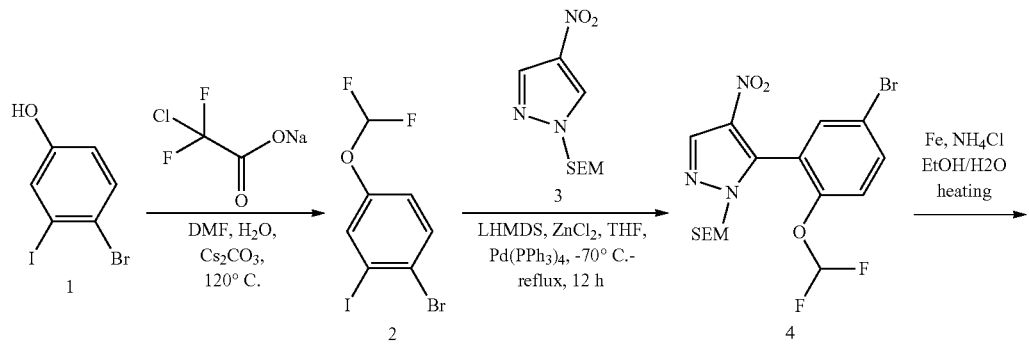

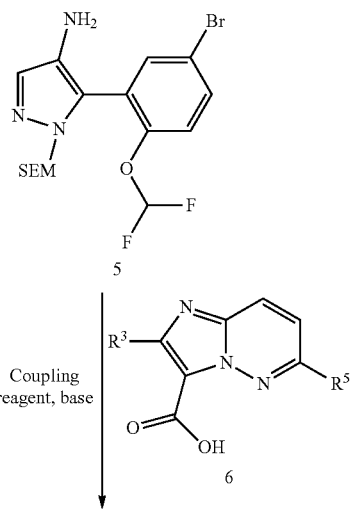

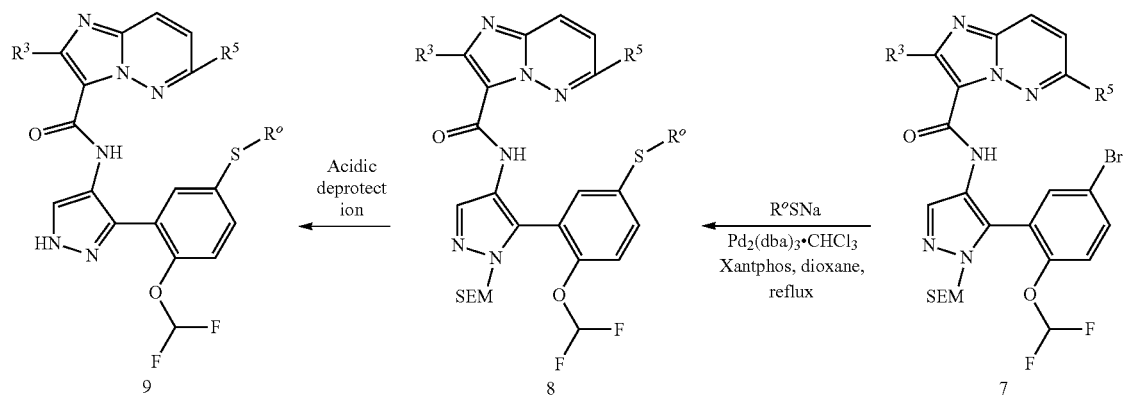

As shown in Scheme 2, compounds of type 2 may be accessed by treating a phenol such as 1, with sodium 2-chloro-2,2-difluoroacetate in the presence of base and heat in the appropriate solvents. Pd-mediated coupling between 2 and 3 provides compounds of type 4. Nitro reduction provides 5 which may be coupled to compounds of type 6 under appropriate amide bond forming conditions to provide 7. 7 may be converted to 8 by Pd mediated thiol displacement, then 8 may be converted to 9 by treatment with acidic conditions.

Scheme 3

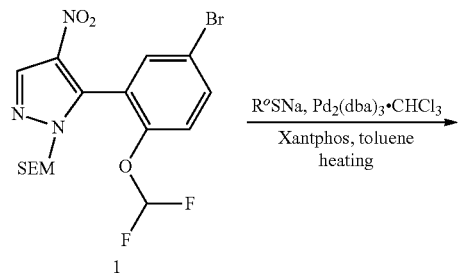

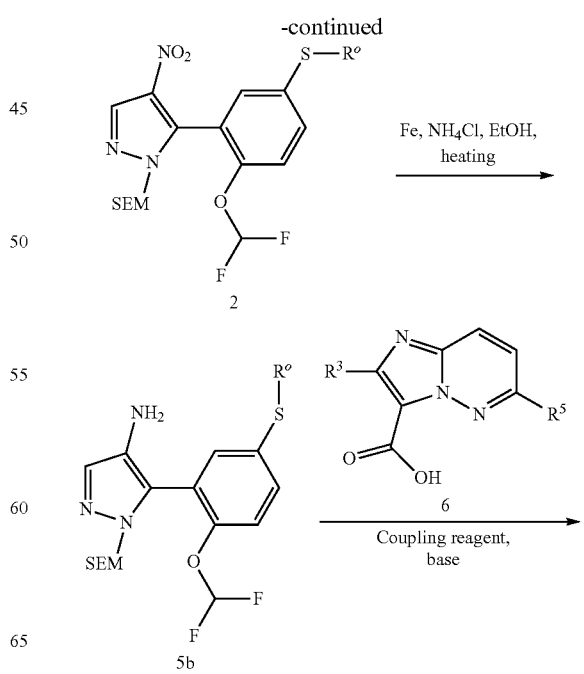

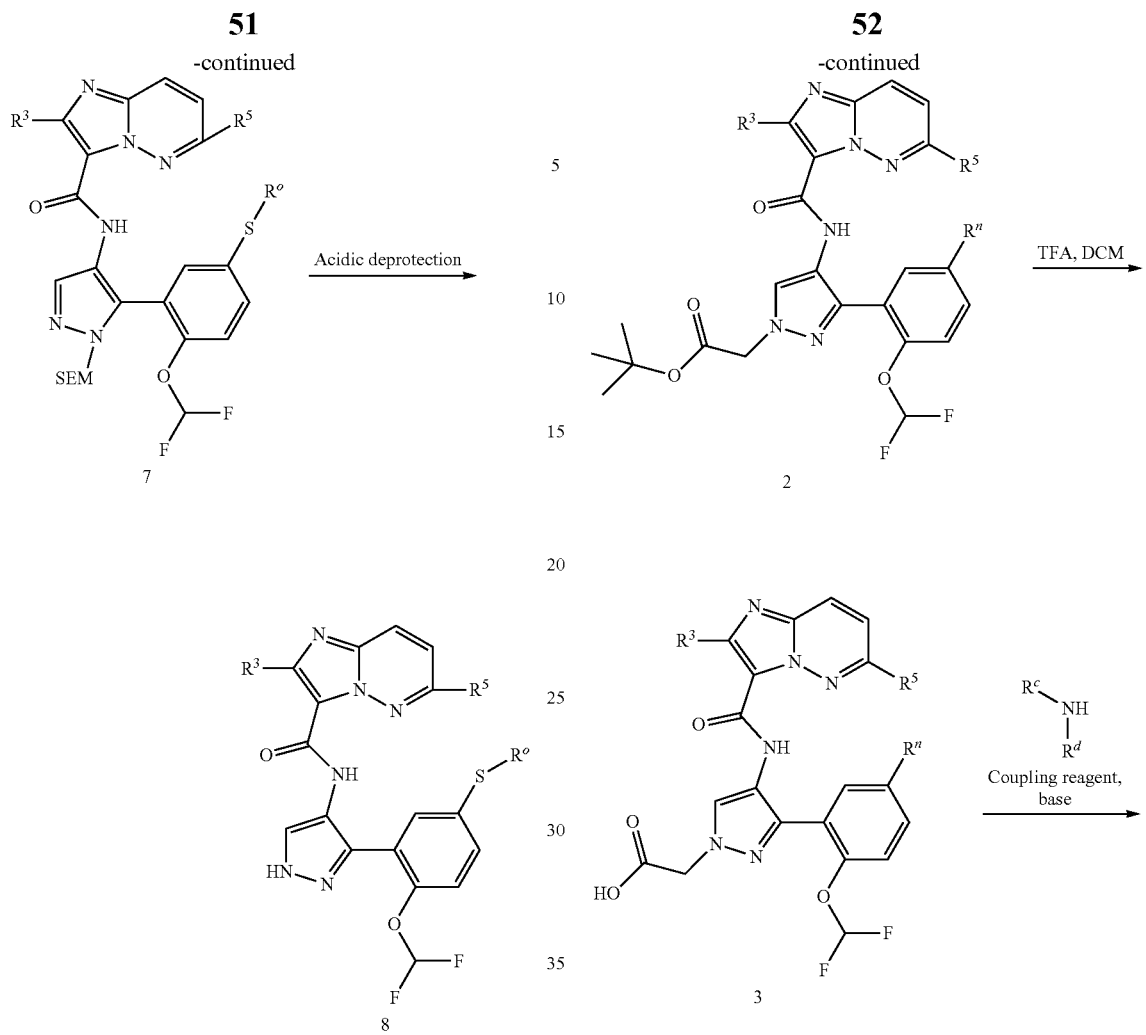

As shown in Scheme 3, compounds of type 2 may be accessed by Pd mediated thiol displacement of compounds of type 1. Nitro reduction provides compounds of type 5b, which may then be coupled to compounds of type 6 under appropriate amide bond forming conditions to provide compounds of type 7. Acidic deprotection provides compounds of type 8.

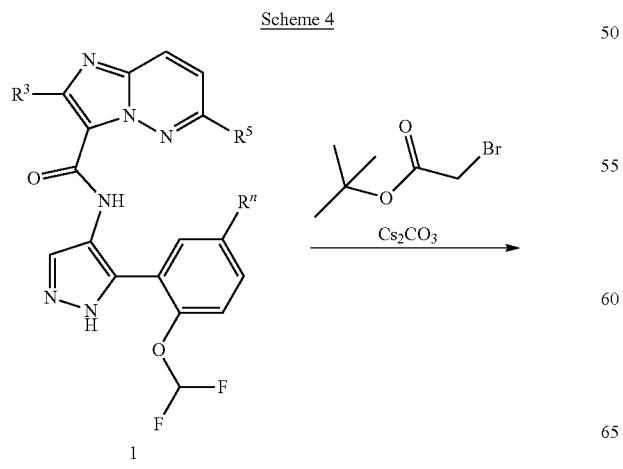

As shown in Scheme 4, compounds of type 2 may be accessed by pyrazole alkylation with an appropriate electrophile in the presence of base. Acidic deprotection, followed by amide bond formation provides compounds of type 4.

Scheme 5

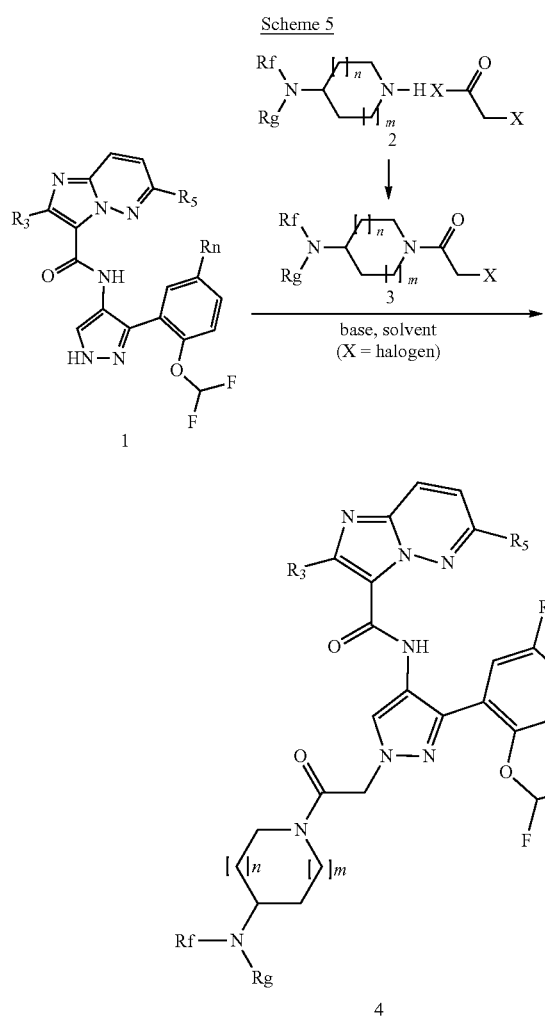

As shown in Scheme 5, compounds of type 3 may be accessed by reaction of haloacetayl halides with appropriate amines. Combination of 3 and 1 in the presence of base results in pyrazole alkylation to provide compounds of type 4.

Scheme 6

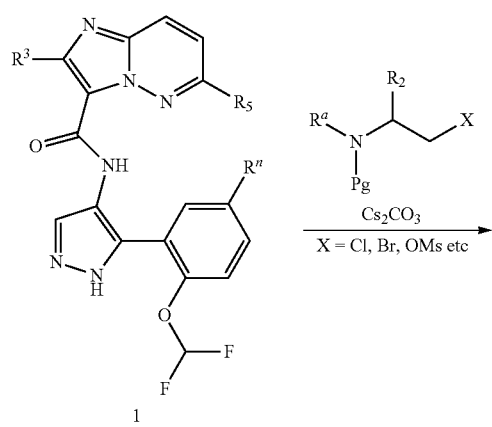

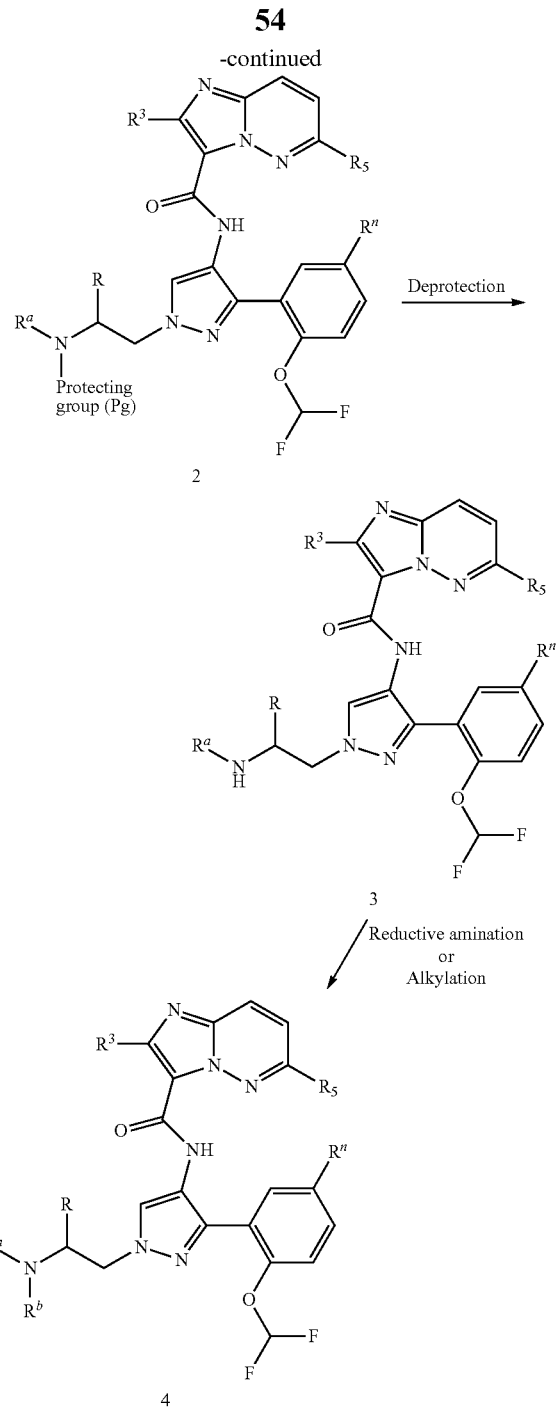

As shown in Scheme 6, compounds of type 2 may be accessed by alkylation of pyrazoles of type 1 with appropriate electrophiles in the presence of base. Amine deprotection, followed by alkylation or reductive amination provided compounds of type 4.

Procedures and LCMS Conditions

Method A

Experiments were performed on a SHIMADZU 20A HPLC with Shim-Pack XR-ODS column (50×3 mm, 2.2 μm particle size), elution with solvent A: water+0.05% trifluoroacetic acid; solvent B: acetonitrile+0.05% trifluoroacetic acid. Gradient:

| Gradient - Time | flow ml/min | % A | % B |
|---|---|---|---|
| 0.00 | 1.0 | 95 | 5 |
| 2.20 | 1.0 | 0 | 100 |
| 3.20 | 1.0 | 0 | 100 |
| 3.30 | 1.0 | 95 | 5 |

Detection—UV (220 and 254 nm) and ELSD
Method B

Experiments were performed on a SHIMADZU 20A HPLC with Shim-Pack XR-ODS column (50×3 mm, 2.2 μm particle size), elution with solvent A: water+0.05% trifluoroacetic acid; solvent B: acetonitrile+0.05% trifluoroacetic acid. Gradient:

| Gradient - Time | flow ml/min | % A | % B |
|---|---|---|---|
| 0.00 | 1.0 | 95 | 5 |
| 3.50 | 1.0 | 15 | 85 |
| 4.20 | 1.0 | 15 | 85 |
| 4.30 | 1.0 | 95 | 5 |

Detection—UV (220 and 254 nm) and ELSD
Method C

Experiments were performed on a SHIMADZU 20A HPLC with Ascentis Express C18 column (30×2.1 mm, 2.7 μm particle size), elution with solvent A: water+0.05% trifluoroacetic acid; solvent B: acetonitrile+0.05% trifluoroacetic acid. Gradient:

| Gradient - Time | flow ml/min | % A | % B |
|---|---|---|---|
| 0.00 | 1.0 | 95 | 5 |
| 2.00 | 1.0 | 5 | 95 |
| 2.70 | 1.0 | 5 | 95 |
| 2.80 | 1.0 | 95 | 5 |

Detection—UV (220 and 254 nm) and ELSD
Method D

Experiments were performed on a SHIMADZU 20A HPLC with Shim-Pack XR-ODS column (50×3 mm, 2.2 μm particle size), elution with solvent A: water+0.05% trifluoroacetic acid; solvent B: acetonitrile+0.05% trifluoroacetic acid. Gradient:

| Gradient - Time | flow ml/min | % A | % B |
|---|---|---|---|
| 0.00 | 1.0 | 70 | 30% |
| 2.50 | 1.0 | 20 | 80 |
| 3.20 | 1.0 | 20 | 80 |
| 3.30 | 1.0 | 95 | 5 |

Detection—UV (220 and 254 nm) and ELSD
Method E

Experiments were performed on a SHIMADZU 20A HPLC with Poroshell HPH-$C_{18}$, column (50×3 mm, 2.7 μm particle size), elution with solvent A: water/5 mM $NH_4HCO_3$; solvent B: acetonitrile. Gradient:

| Gradient - Time | flow ml/min | % A | % B |
|---|---|---|---|
| 0.00 | 1.5 | 90 | 10 |
| 2.00 | 1.5 | 5 | 95 |
| 2.70 | 1.5 | 5 | 95 |
| 2.80 | 1.5 | 90 | 10 |

Detection—UV (220 and 254 nm) and ELSD
Method F

Experiments were performed on a SHIMADZU 20A HPLC with Ascentis Express C18 column (30×2.1 mm, 2.7 μm particle size), elution with solvent A: water+0.05% trifluoroacetic acid; solvent B: acetonitrile+0.05% trifluoroacetic acid. Gradient:

| Gradient - Time | flow ml/min | % A | % B |
|---|---|---|---|
| 0.00 | 1.0 | 95 | 5 |
| 2.00 | 1.0 | 0 | 100 |
| 2.70 | 1.0 | 0 | 100 |
| 2.80 | 1.0 | 95 | 5 |

Detection—UV (220 and 254 nm) and ELSD
Method G

Experiments were performed on a SHIMADZU 20A HPLC with Ascentis Express C18 column (30×2.1 mm, 2.7 μm particle size), elution with solvent A: water+0.05% trifluoroacetic acid; solvent B: acetonitrile+0.05% trifluoroacetic acid. Gradient:

| Gradient - Time | flow ml/min | % A | % B |
|---|---|---|---|
| 0.00 | 1.0 | 95 | 5 |
| 3.50 | 1.0 | 20 | 80 |
| 4.30 | 1.0 | 20 | 80 |
| 4.40 | 1.0 | 95 | 5 |

Detection—UV (220 and 254 nm) and ELSD
Method H

Experiments were performed on a SHIMADZU 20A HPLC with Ascentis Express C18 column (30×2.1 mm, 2.7 μm particle size), elution with solvent A: water+0.05% trifluoroacetic acid; solvent B: acetonitrile+0.05% trifluoroacetic acid. Gradient:

| Gradient - Time | flow ml/min | % A | % B |
|---|---|---|---|
| 0.00 | 1.0 | 95 | 5 |
| 1.10 | 1.0 | 0 | 100 |
| 1.60 | 1.0 | 0 | 100 |
| 1.70 | 1.0 | 95 | 5 |

Detection—UV (220 and 254 nm) and ELSD
Method I

Experiments were performed on a SHIMADZU 20A HPLC with Shim-Pack XR-ODS column (50×3 mm, 2.2 μm particle size), elution with solvent A: water+0.05% trifluoroacetic acid; solvent B: acetonitrile+0.05% trifluoroacetic acid. Gradient:

| Gradient - Time | flow ml/min | % A | % B |
|---|---|---|---|
| 0.00 | 1.0 | 95 | 5 |
| 1.10 | 1.0 | 0 | 100 |
| 1.60 | 1.0 | 0 | 100 |
| 1.70 | 1.0 | 95 | 5 |

Detection—UV (220 and 254 nm) and ELSD

Method J

Experiments were performed on a SHIMADZU 20A HPLC with a C18-reverse-phase column (50×3 mm Xtimate TM-C18, 2.2 μm particle size), mobile phases: Solvent A: water+0.1% formic acid; Solvent B: acetonitrile+0.05% formic acid. Gradient:

| Gradient - Time | flow ml/min | % A | % B |
| --- | --- | --- | --- |
| 0.00 | 1.0 | 95 | 5 |
| 2.00 | 1.0 | 0 | 100 |
| 3.10 | 1.0 | 0 | 100 |
| 3.20 | 1.0 | 95 | 5 |

Detection—UV (220 and 254 nm) and ELSD

Method K

Experiments performed on an Agilent 1290 UHPLC coupled with an Agilent MSD (6140) mass spectrometer using ESI as the ionization source. The LC separation was performed using a Phenomenex XB-C18, 1.7 mm, 50×2.1 mm column with a 0.4 mL/minute flow rate. Solvent A is water with 0.1% formic acid and solvent B is acetonitrile with 0.1% formic acid. The gradient was 2-98% solvent B over 7 min and hold 98% B for 1.5 min following equilibration for 1.5 min. LC column temperature is 40° C. UV absorbance was collected at 220 nm and 254 nm and mass spec full scan was applied to all experiments.

Example 1

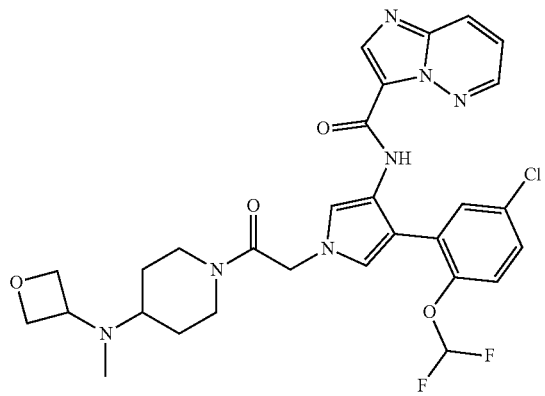 [SMILES: CN(C1CCN(C(=O)Cn2cc(NC(=O)c3cnc4cccnn34)c(-c3cc(Cl)ccc3OC(F)F)c2)CC1)C1COC1]

N-[3-[5-chloro-2-(difluoromethoxy)phenyl]-1-(2-[4-[methyl(oxetan-3-yl)amino]piperidin-1-yl]-2-oxo-ethyl)-1H-pyrazol-4-yl]imidazo[1,2-b]pyridazine-3-carboxamide

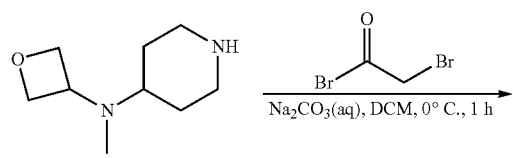

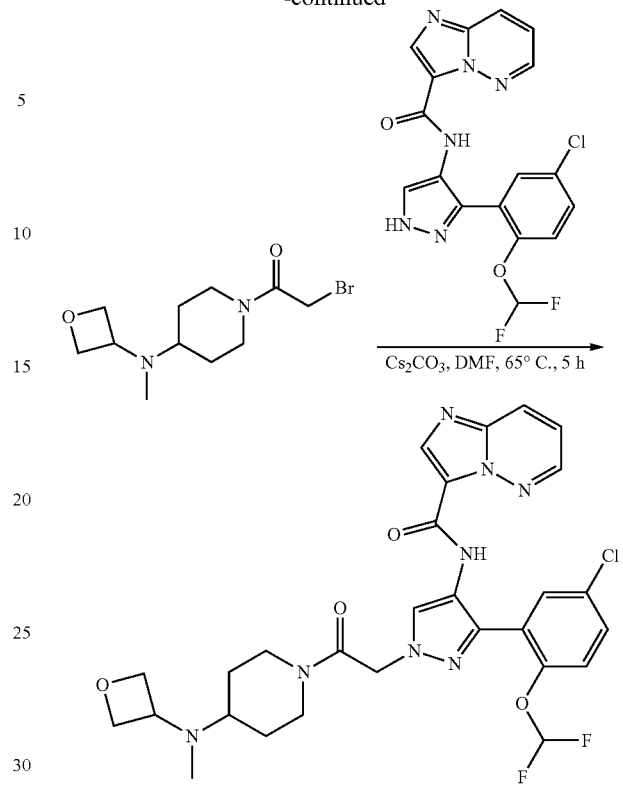

A solution of 2-bromoacetyl bromide (285 mg, 1.41 mmol) in dichloromethane (4.0 mL) was added dropwise to a mixture of N-methyl-N-(oxetan-3-yl)piperidin-4-amine (200 mg, 1.18 mmol) in dichloromethane (10 mL) and saturated sodium carbonate (10 mL) at 0° C. The reaction mixture was then stirred for 1 h at room temperature. Phases were separated. The aqueous phase was extracted with 3×30 mL of dichloromethane and the organic layers combined. The organic layers were washed with brine, dried over anhydrous sodium sulfate and concentrated under vacuum. This resulted in 200 mg of 2-bromo-1-[4-[methyl(oxetan-3-yl)amino]piperidin-1-yl]ethan-1-one as a light yellow solid, which was used without purification.

A solution of 2-bromo-1-4-[methyl(oxetan-3-yl)amino]piperidin-1-yl ethan-1-one (86.0 mg, 0.295 mmol) in DMF (2.0 mL) was added dropwise to a mixture of N-[3-[5-chloro-2-(difluoromethoxy)phenyl]-1H-pyrazol-4-yl]imidazo[1,2-b]pyridazine-3-carboxamide (100 mg, 0.247 mmol) and Cs$_2$CO$_3$ (160 mg, 0.491 mmol) in N,N-dimethylformamide (5.0 mL) at 65° C. The reaction mixture was stirred at 65° C. for 5 h. Water (20 mL) was added. The resulting mixture was extracted with 3×50 mL of ethyl acetate and the organic layers combined. The organic layers were washed with brine, dried over anhydrous sodium sulfate and concentrated under vacuum. The residue was purified by Prep-HPLC with the following conditions: Column: XBridge Prep C18 OBD Column, 5 um, 19*150 mm; Mobile Phase A: Water (0.1% NH$_4$HCO$_3$), Mobile Phase B: ACN; Flow rate: 30 mL/min; Gradient: 25% B to 45% B in 8 min; 254/220 nm Detector This resulted in 15.9 mg of N-[3-[5-chloro-2-(difluoromethoxy)phenyl]-1-(2-[4-[methyl(oxetan-3-yl)amino]piperidin-1-yl]-2-oxoethyl)-1H-pyrazol-4-yl]imidazo[1,2-b]pyridazine-3-carboxamide as a white solid. LC/MS (Method A, ESI): [M+H]$^+$=615.3, R$_T$=1.39 min; $^1$H NMR (400 MHz, CD$_3$OD-d$_4$): δ (ppm)

8.59 (dd, J=4.8, 1.6 Hz, 1H), 8.48 (s, 1H), 8.44 (s, 1H), 8.27 (dd, J=9.4, 1.4 Hz, 1H), 7.73 (d, J=2.8 Hz, 1H), 7.60 (dd, J=8.8, 2.4 Hz, 1H), 7.54-7.47 (m, 2H), 6.81 (t, J=73.4 Hz, 1H), 5.34 (d, J=16.4 Hz, 1H), 5.22 (d, J=16.4 Hz, 1H), 4.68-4.66 (m, 4H), 4.63-4.60 (m, 1H), 4.11-4.03 (m, 2H), 3.26-3.10 (m, 1H), 2.75-2.63 (m, 2H), 2.23 (s, 3H), 1.81-1.75 (m, 2H), 1.64-1.46 (m, 2H).

Example 3

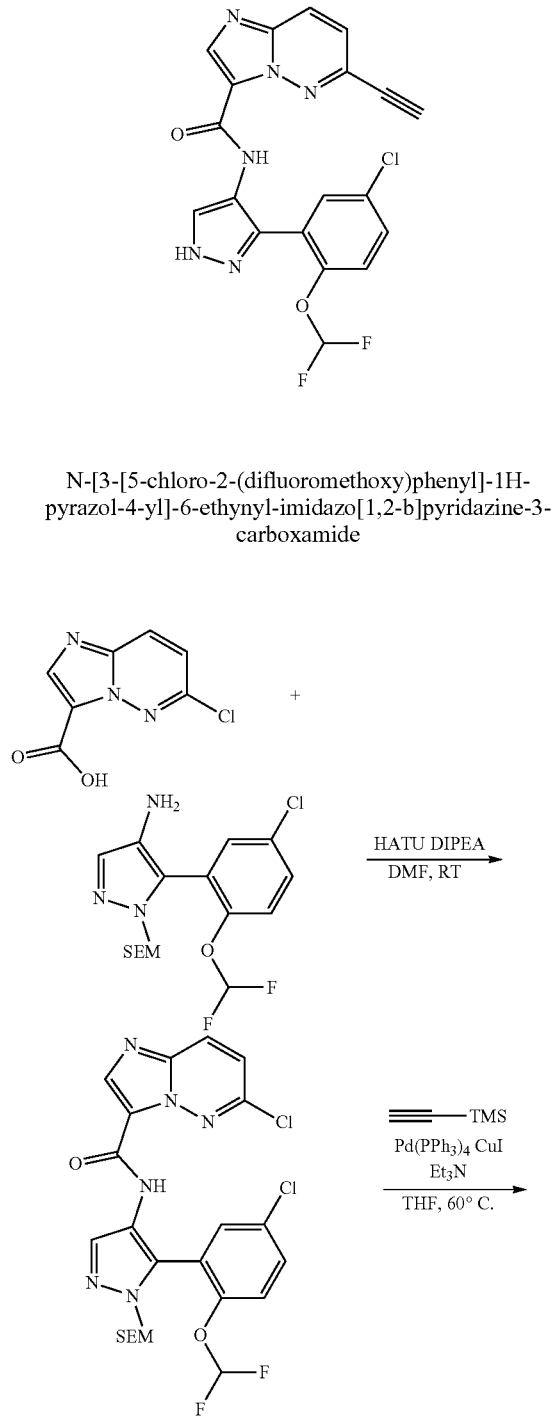

N-[3-[5-chloro-2-(difluoromethoxy)phenyl]-1H-pyrazol-4-yl]-6-ethynyl-imidazo[1,2-b]pyridazine-3-carboxamide

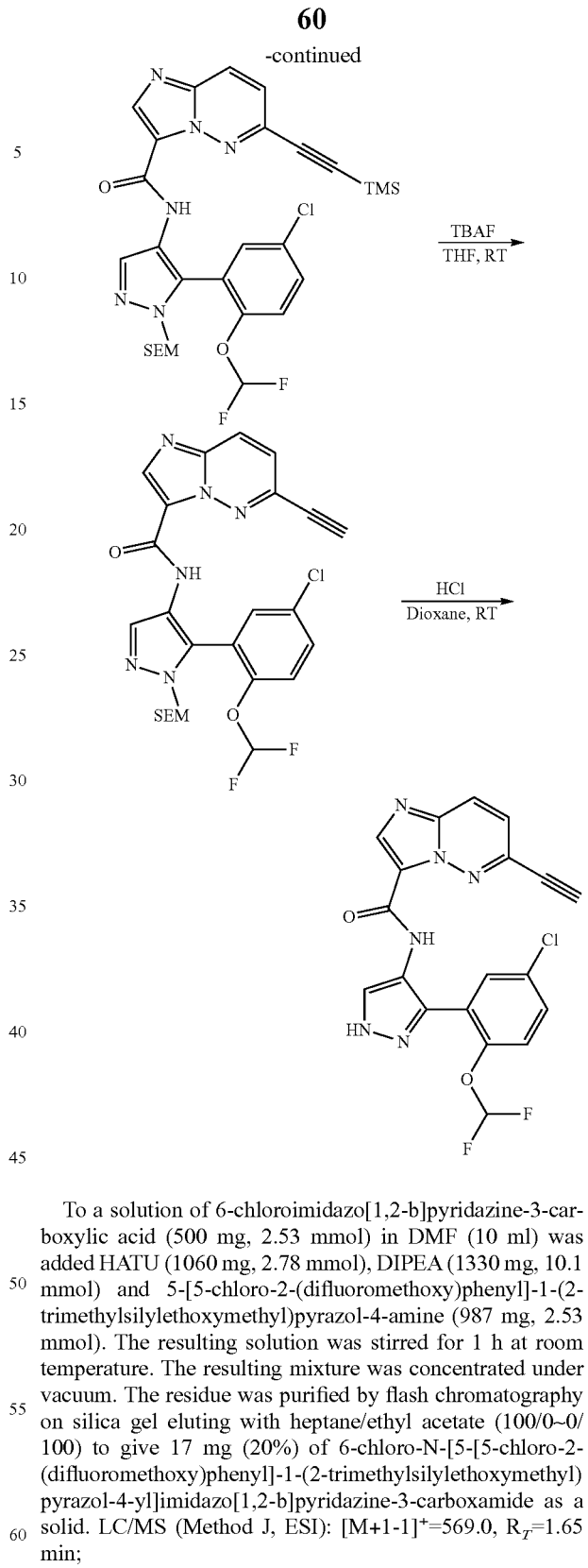

To a solution of 6-chloroimidazo[1,2-b]pyridazine-3-carboxylic acid (500 mg, 2.53 mmol) in DMF (10 ml) was added HATU (1060 mg, 2.78 mmol), DIPEA (1330 mg, 10.1 mmol) and 5-[5-chloro-2-(difluoromethoxy)phenyl]-1-(2-trimethylsilylethoxymethyl)pyrazol-4-amine (987 mg, 2.53 mmol). The resulting solution was stirred for 1 h at room temperature. The resulting mixture was concentrated under vacuum. The residue was purified by flash chromatography on silica gel eluting with heptane/ethyl acetate (100/0~0/100) to give 17 mg (20%) of 6-chloro-N-[5-[5-chloro-2-(difluoromethoxy)phenyl]-1-(2-trimethylsilylethoxymethyl)pyrazol-4-yl]imidazo[1,2-b]pyridazine-3-carboxamide as a solid. LC/MS (Method J, ESI): [M+1-1]$^+$=569.0, R$_T$=1.65 min;

To a solution of 6-chloro-N-[5-[5-chloro-2-(difluoromethoxy)phenyl]-1-(2-trimethylsilylethoxymethyl)pyrazol-4-yl]imidazo[1,2-b]pyridazine-3-carboxamide (600 mg, 1.05 mmol) in tetrahydrofuran (4.2 mL) was added successively cuprous iodide (40.1 mg, 0.00713 mL, 0.211 mmol), tetrakis(triphenylphosphine)palladium(0) (122 mg, 0.105 mmol), ethynyl(trimethyl)silane (124 mg, 0.179 mL, 1.26 mmol), and triethylamine (213 mg, 0.294 mL, 2.11 mmol) under nitrogen at room temperature. The resulting solution was stirred overnight at 60° C. under nitrogen and allowed to cool to room temperature. The resulting mixture was concentrated under vacuum. The residue was purified by flash chromatography on silica gel eluting with heptane/ethyl acetate (100/0~50/50) to afford 226 mg (34%) of N-[5-[5-chloro-2-(difluoromethoxy)phenyl]-1-(2-trimethylsilylethoxymethyl)pyrazol-4-yl]-6-(2-trimethylsilylethynyl)imidazo[1,2-b]pyridazine-3-carboxamide as an oil. LC/MS (Method J, ESI): [M+H]+=631.1, RT=2.12 min;

To a solution of N-[5-[5-chloro-2-(difluoromethoxy)phenyl]-1-(2-trimethylsilylethoxymethyl)pyrazol-4-yl]-6-(2-trimethylsilylethynyl)imidazo[1,2-b]pyridazine-3-carboxamide (220 mg, 0.349 mmol) in dichloromethane (1 mL) was added tetrabutylammonium fluoride in THF (1 M, 0.7 mL) at room temperature. The resulting solution was stirred for 1 h. The resulting mixture was concentrated under vacuum. The residue was purified by flash chromatography on silica gel eluting with heptane/ethyl acetate (100/0~0/100) to afford 112 mg (57%) of N-[5-[5-chloro-2-(difluoromethoxy)phenyl]-1-(2-trimethylsilylethoxymethyl)pyrazol-4-yl]-6-ethynyl-imidazo[1,2-b]pyridazine-3-carboxamide as an oil. LC/MS (Method J, ESI): [M+H]+=559.0, RT=1.59 min;

A solution of N-[5-[5-chloro-2-(difluoromethoxy)phenyl]-1-(2-trimethylsilylethoxymethyl)pyrazol-4-yl]-6-ethynyl-imidazo[1,2-b]pyridazine-3-carboxamide (110 mg, 0.197 mmol) in hydrochloric acid/1,4-dioxane (4 M, 0.5 mL) at room temperature. The resulting solution was stirred for 1 h. The resulting mixture was concentrated under vacuum. The residue was purified by flash chromatography on silica gel eluting with heptane/ethyl acetate (100/0~0/100) to afford 112 mg (57%) of N-[3-[5-chloro-2-(difluoromethoxy)phenyl]-1H-pyrazol-4-yl]-6-ethynyl-imidazo[1,2-b]pyridazine-3-carboxamide as an oil. LC/MS (Method K, ESI): [M+H]+=429.1, RT=4.01 min. 1H NMR (400 MHz, DMSO-d6) δ 13.18 (s, 1H), 10.05 (s, 1H), 8.47 (s, 1H), 8.44-8.35 (m, 2H), 7.71-7.53 (m, 3H), 7.44 (d, J=8.8 Hz, 1H), 7.10 (t, J=73.3 Hz, 1H), 3.57 (s, 1H).

Example 4

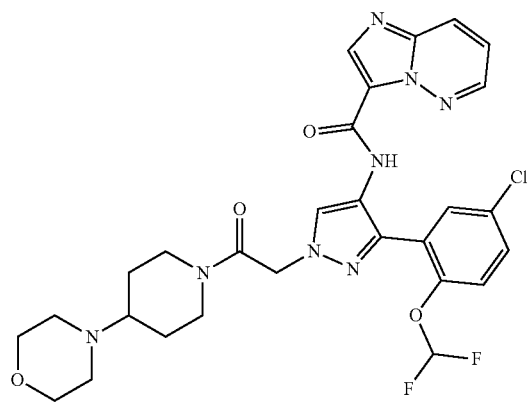 [SMILES: O=C(Nc1cn(CC(=O)N2CCC(N3CCOCC3)CC2)nc1-c1cc(Cl)ccc1OC(F)F)c1cnc2cccnn12]

N-[3-[5-chloro-2-(difluoromethoxy)phenyl]-1-[2-[4-(morpholin-4-yl)piperidin-1-yl]-2-oxoethyl]-1H-pyrazol-4-yl]imidazo[1,2-b]pyridazine-3-carboxamide

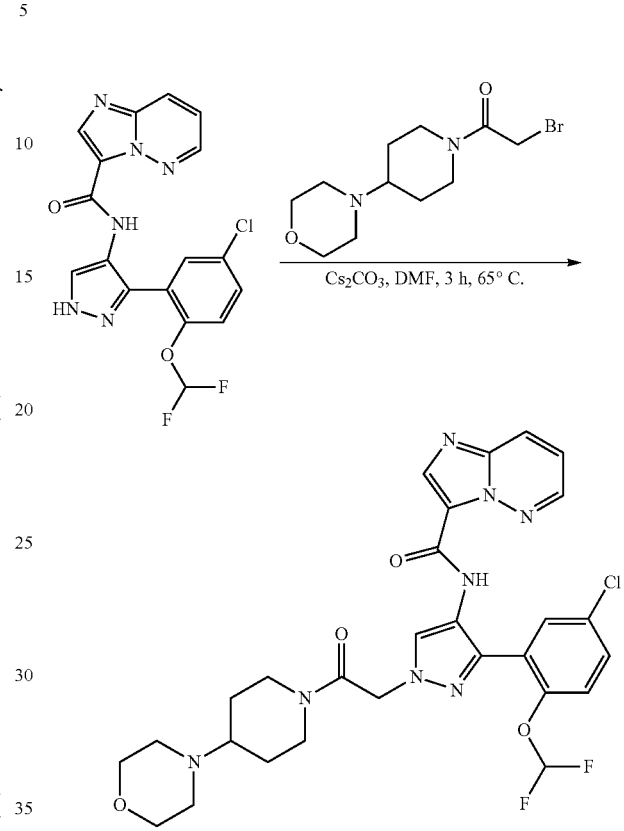

To a solution of N-[3-[5-chloro-2-(difluoromethoxy)phenyl]-1H-pyrazol-4-yl]imidazo[1,2-b]pyridazine-3-carboxamide (130 mg, 0.321 mmol) in N,N-dimethylformamide (18 mL) was added Cs$_2$CO$_3$ (300 mg, 0.921 mmol) and 2-bromo-1-[4-(morpholin-4-yl)piperidin-1-yl]ethan-1-one (130 mg, 0.446 mmol). The reaction mixture was stirred at 65° C. for 3 h and allowed to cool to room temperature. Water (30 mL) was added. The resulting solution was extracted with 3×50 mL of ethyl acetate and the organic layers combined. The organic extracts were washed with brine, dried over anhydrous sodium sulfate and concentrated under vacuum. The residue was purified by Prep-HPLC with the following conditions: Column: XBridge Prep C18 OBD Column, 5 um, 19*150 mm; Mobile Phase A: Water (0.1% NH$_4$HCO$_3$), Mobile Phase B: ACN; Flow rate: 30 mL/min; Gradient: 25% B to 45% B in 8 min; 254/220 nm; Detector to give 32.7 mg (17%) of N-[3-[5-chloro-2-(difluoromethoxy)phenyl]-1-[2-[4-(morpholin-4-yl)piperidin-1-yl]-2-oxoethyl]-1H-pyrazol-4-yl]imidazo[1,2-b]pyridazine-3-carboxamide as a white solid. LC/MS (Method A, ESI): [M+H]+=615.3, R$_T$=1.39 min; $^1$H NMR (400 MHz, CD$_3$OD-d$_4$): δ (ppm) 8.58 (dd, J=4.8, 1.6 Hz, 1H), 8.47 (s, 1H), 8.43 (s, 1H), 8.27 (dd, J=9.4, 1.6 Hz, 1H), 7.72 (d, J=2.8 Hz, 1H), 7.60 (dd, J=8.8, 2.8 Hz, 1H), 7.52-7.47 (m, 2H), 6.81 (t, J=73.6 Hz, 1H), 5.34 (d, J=16.0 Hz, 1H), 5.23 (d, J=16.4 Hz, 1H), 4.59-4.55 (m, 1H), 4.11-4.08 (m, 1H), 3.72 (t, J=4.4 Hz, 4H), 3.25-3.19 (m, 1H), 2.84-2.79 (m, 1H), 2.63 (t, J=4.4 Hz, 4H), 2.58-2.52 (m, 1H), 2.01-1.98 (m, 2H), 1.57-1.47 (m, 2H).

Example 5

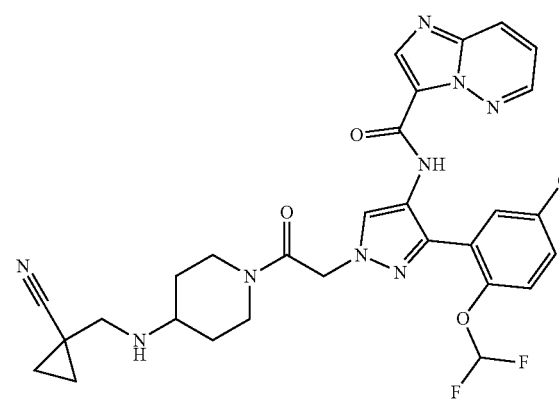

N-[3-[5-chloro-2-(difluoromethoxy)phenyl]-1-[2-(4-[[(1-cyanocyclopropyl)-methyl]amino]piperidin-1-yl)-2-oxoethyl]-1H-pyrazol-4-yl]imidazo[1,2-b]pyridazine-3-carboxamide

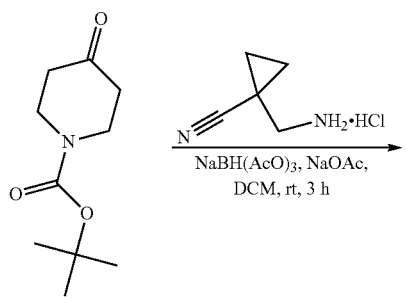

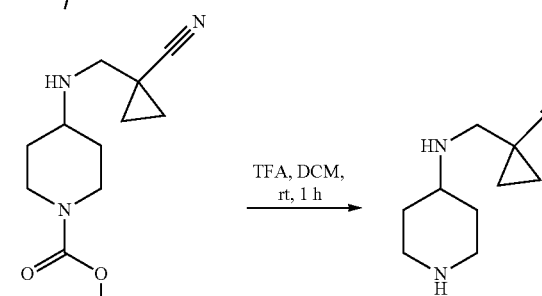

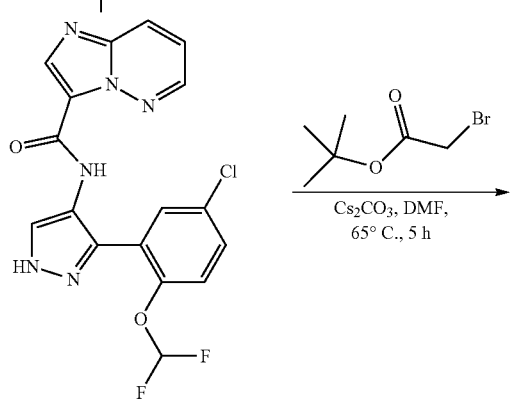

To a solution of tert-butyl 4-oxopiperidine-1-carboxylate (300 mg, 1.51 mmol) in dichloromethane (30 mL) was added 1-(aminomethyl)cyclopropane-1-carbonitrile hydrochloride (216 mg, 1.63 mmol) and NaOAc (120 mg, 1.46 mmol). The resulting solution was stirred for 2 h at room temperature. NaBH(OAc)$_3$ (636 mg, 3.00 mmol) was then added. The reaction mixture was stirred at room temperature for 3 h, and then saturated sodium carbonate (50 mL) was added. Phases were separated, and the aqueous phase was extracted with 3×50 mL of dichloromethane and the organic layers combined. The organic phases were dried over anhydrous sodium sulfate and concentrated under vacuum to give 300 mg of tert-butyl 4-[[(1-cyanocyclopropyl)methyl]amino]piperidine-1-carboxylate as colorless oil. LC/MS (Method H, ESI): [M+H]$^+$=280.1, R$_T$=0.55 min.

To a solution of tert-butyl 4-[[(1-cyanocyclopropyl)methyl]amino]piperidine-1-carboxylate (200 mg, 0.716 mmol) in dichloromethane (10 mL) was added trifluoroacetic acid (3.0 mL) dropwise with stirring at 0-5° C. The resulting solution was stirred for 1 h at room temperature.

The resulting mixture was concentrated under vacuum to obtain 200 mg (crude) of 1-[[(piperidin-4-yl)amino]methyl]cyclopropane-1-carbonitrile trifluoroacetic acid salt as yellow oil. LC/MS (Method I, ESI): [M+H]⁺=180.1 RT=0.16 min.

To a solution of N-[3-[5-chloro-2-(difluoromethoxy)phenyl]-1H-pyrazol-4-yl]imidazo[1,2-b]pyridazine-3-carboxamide (200 mg, 0.494 mmol) in N,N-dimethylformamide (5.0 mL) was added tert-butyl 2-bromoacetate (105 mg, 0.538 mmol) and Cs₂CO₃ (321 mg, 0.985 mmol). The resulting mixture was stirred at 65° C. for 2 h and allowed to cool to room temperature. Water (30 mL) was added. The resulting mixture was extracted with 3×50 mL of ethyl acetate and the organic layers combined. The organic layers were dried over anhydrous sodium sulfate and concentrated under vacuum. The residue was purified by flash chromatography on silica gel eluting with ethyl acetate and petroleum ether gradient (0-60% ethyl acetate). The appropriate fractions were combined and concentrated under vacuum to give 200 mg (78%) of tert-butyl 2-[3-[5-chloro-2-(difluoromethoxy)phenyl]-4-[imidazo[1,2-b]pyridazine-3-amido]-1H-pyrazol-1-yl]acetate as a yellow solid. LC/MS (Method H, ESI): [M+H]⁺=519.0, R$_T$=0.97 min.

To a solution of 4N HCl in dioxane (10 mL) was added tert-butyl 2-[3-[5-chloro-2-(difluoromethoxy)phenyl]-4-[imidazo[1,2-b]pyridazine-3-amido]-1H-pyrazol-1-yl]acetate (200 mg, 0.385 mmol) at room temperature. The resulting solution was stirred at room temperature for 2 h. The resulting mixture was concentrated under vacuum to afford 2-[3-[5-chloro-2-(difluoromethoxy)phenyl]-4-[imidazo[1,2-b]pyridazine-3-amido]-1H-pyrazol-1-yl]acetic acid (150 mg), which was used for next step without further purification. LC/MS (Method I, ESI): [M+H]⁺=463.2 R$_T$=0.76 min.

To a solution of 2-[3-[5-chloro-2-(difluoromethoxy)phenyl]-4-[imidazo[1,2-b]pyridazine-3-amido]-1H-pyrazol-1-yl]acetic acid (80.00 mg, 0.173 mmol) in DMA (10 mL) was added 1-{[(piperidin-4-yl)amino]methyl}cyclopropane-1-carbonitrile trifluoroacetic acid salt (44.8 mg, 0.207 mmol) from step 2 in this example, (7-Azabenzotriazol-1-yloxy)tripyrrolidinophosphonium hexafluorophosphate (PyAOP) (135 mg, 0.259 mmol), 4-dimethylaminopyridine (2.11 mg, 0.0173 mmol) and DIPEA (67 mg, 0.52 mmol). The resulting solution was stirred at 65° C. for 5 h and allowed to cool to room temperature. Water (30 mL) was added. The resulting mixture was extracted with 3×30 mL of ethyl acetate and the organic layers combined. The organic layers were washed with brine, dried over anhydrous sodium sulfate and concentrated in vacuum. The residue was purified by flash chromatography on silica gel eluting with ethyl acetate and petroleum ether gradient (0-80% ethyl acetate). The appropriate fractions were combined and concentrated under vacuum. The residue was further purified by Prep-HPLC with the following conditions: Column: XBridge Prep C18 OBD Column, 5 um, 19*150 mm; Mobile Phase A: Water (0.1% NH₄HCO₃), Mobile Phase B: ACN; Flow rate: 30 mL/min; Gradient: 25% B to 45% B in 8 min; 254/220 nm; Detector to give 4.10 mg of N-[3-[5-chloro-2-(difluoromethoxy)phenyl]-1-[2-(4-[[(1-cyanocyclopropyl)methyl]amino]piperidin-1-yl)-2-oxoethyl]-1H-pyrazol-4-yl]imidazo[1,2-b]pyridazine-3-carboxamide as a white solid. LC/MS (Method E, ESI): [M+H]⁺=624.2, R$_T$=1.24 min; ¹H NMR (400 MHz, CD₃OD-d₄): δ (ppm) 8.58 (d, J=4.4 Hz, 1H), 8.47 (s, 1H), 8.43 (s, 1H), 8.27 (d, J=8.8 Hz, 1H), 7.73 (d, J=2.4 Hz, 1H), 7.60 (dd, J=8.8, 2.8 Hz, 1H), 7.52-7.47 (m, 2H), 6.80 (t, J=73.6 Hz, 1H), 5.32 (d, J=16.8 Hz, 1H), 5.26 (d, J=16.8 Hz, 1H), 4.45-4.41 (m, 1H), 4.05-3.98 (m, 1H), 3.07-2.81 (m, 2H), 2.77 (s, 2H), 2.09-1.96 (m, 2H), 1.55-1.29 (m, 3H), 1.27-1.22 (m, 2H), 1.05-0.97 (m, 2H).

Example 7

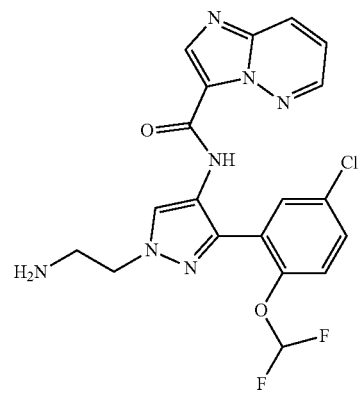 [SMILES: NCCn1cc(NC(=O)c2cnc3cccnn23)c(-c2cc(Cl)ccc2OC(F)F)n1]

N-[1-(2-aminoethyl)-3-[5-chloro-2-(difluoromethoxy)phenyl]-1H-pyrazol-4-yl]imidazo[1,2-b]pyridazine-3-carboxamide

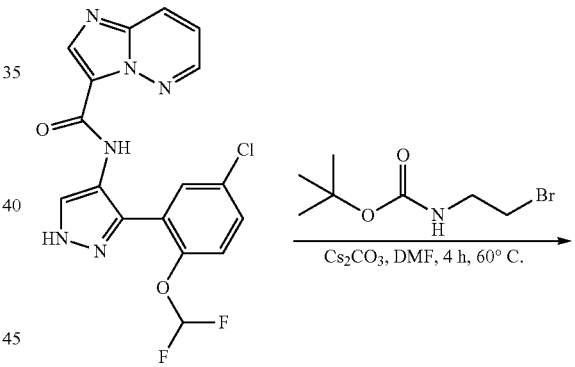

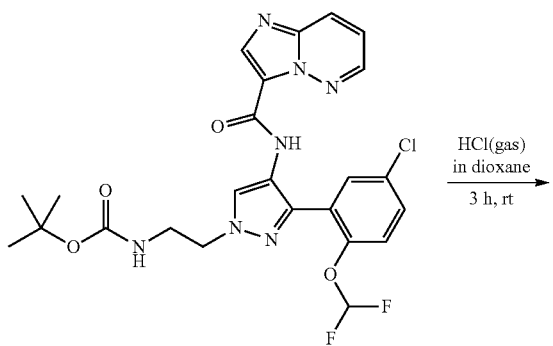

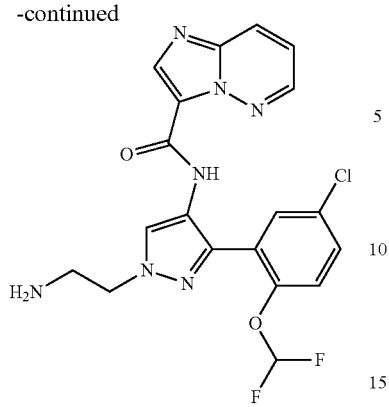

To a solution of N-[3-[5-chloro-2-(difluoromethoxy)phenyl]-1H-pyrazol-4-yl]imidazo[1,2-b]pyridazine-3-carboxamide (200 mg, 0.494 mmol) in N,N-dimethylformamide (10 mL) was added tert-butyl N-(2-bromoethyl)carbamate (120 mg, 0.535 mmol) and $Cs_2CO_3$ (320 mg, 0.982 mmol). The reaction mixture was stirred at 60° C. for 4 h and allowed to cool to room temperature. Water (100 mL) was added. The resulting mixture was extracted with 3×100 mL of ethyl acetate and the organic layers combined. The organic layers were washed with brine, dried over anhydrous sodium sulfate and concentrated under vacuum. The residue was purified by flash chromatography on silica gel eluting with ethyl acetate and petroleum ether gradient (0-40% ethyl acetate). The appropriate fractions were combined and concentrated under vacuum to give 200 mg (74%) of tert-butyl N-(2-[3-[5-chloro-2-(difluoromethoxy)phenyl]-4-[imidazo[1,2-b]pyridazine-3-amido]-1H-pyrazol-1-yl]ethyl)carbamate as a yellow solid. LC/MS (Method H, ESI): $[M+H]^+$= 548.1, $R_T$=0.91 min.

To a solution of 4 N HCl in dioxane (10 mL) was added tert-butyl N-(2-[3-[5-chloro-2-(difluoromethoxy)phenyl]-4-[imidazo[1,2-b]pyridazine-3-amido]-1H-pyrazol-1-yl]ethyl)carbamate (150 mg, 0.274 mmol) in several portions. The reaction mixture was stirred at room temperature for 3 h and concentrated under vacuum. The residue was purified by Prep-HPLC with the following conditions: Column: XBridge Prep C18 OBD Column, 5 um, 19*150 mm; Mobile Phase A: Water (0.1% $NH_4HCO_3$), Mobile Phase B: ACN; Flow rate: 30 mL/min; Gradient: 25% B to 45% B in 8 min; 254/220 nm Detector to obtain 49.1 mg (40%) of N-[1-(2-aminoethyl)-3-[5-chloro-2-(difluoromethoxy)phenyl]-1H-pyrazol-4-yl]imidazo[1,2-b]pyridazine-3-carboxamide as a white solid. LC/MS (Method G, ESI): $[M+H]^+$= 448.1, $R_T$=1.28 min; $^1$H NMR (400 MHz, $CD_3OD$-$d_4$): δ (ppm) 8.59 (dd, J=4.4, 1.6 Hz, 1H), 8.47 (s, 1H), 8.41 (s, 1H), 8.27 (dd, J=9.2, 1.6 Hz, 1H), 7.71 (d, J=2.4 Hz, 1H), 7.59 (dd, J=8.4, 2.4 Hz, 1H), 7.52-7.45 (m, 2H), 6.82 (t, J=73.6 Hz, 1H), 4.32 (t, J=6.0 Hz, 2H), 3.18 (t, J=6.0 Hz, 2H).

Example 8

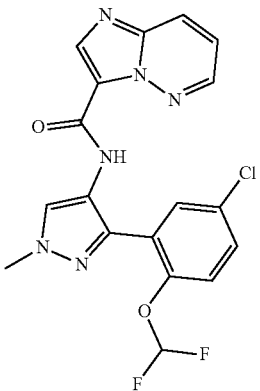 [SMILES: Cn1cc(NC(=O)c2cnc3cccnn23)c(-c2cc(Cl)ccc2OC(F)F)n1]

N-[3-[5-chloro-2-(difluoromethoxy)phenyl]-1-methyl-1H-pyrazol-4-yl]imidazo[1,2-b]pyridazine-3-carboxamide

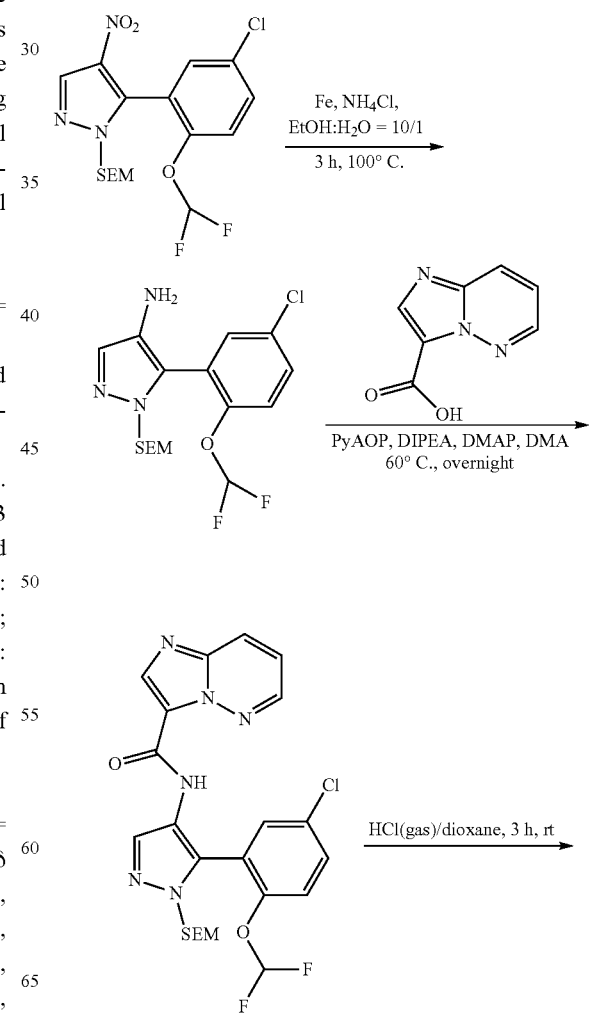

-continued

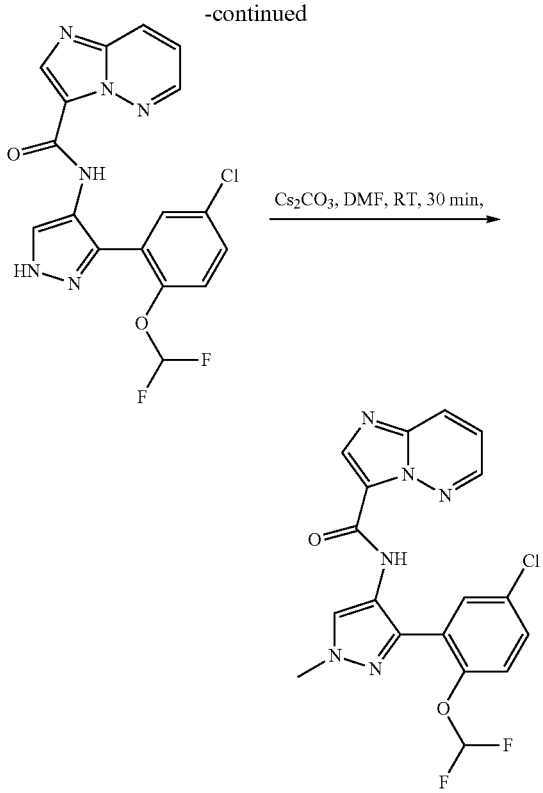

Cs₂CO₃, DMF, RT, 30 min,

To a solution of 5-[5-chloro-2-(difluoromethoxy)phenyl]-4-nitro-1-[[2-(trimethylsilyl)ethoxy]methyl]-1H-pyrazole (4.60 g, 11.0 mmol) in ethanol (50 mL) and water (5 mL) was added iron powder (6.12 g, 110 mmol) and NH₄Cl (2.93 g, 54.78 mmol). The resulting mixture was stirred at reflux for 3 h under nitrogen and allowed to cool to room temperature. The solids were filtered off and washed with EtOH. The filtrate was concentrated under vacuum. The residue was partitioned between EtOAc and brine. The organic phase was dried over anhydrous sodium sulfate and concentrated under vacuum to give 4.01 g (94%) of 5-[5-chloro-2-(difluoromethoxy)phenyl]-1-[[2-(trimethylsilyl)ethoxy]methyl]-1H-pyrazol-4-amine as yellow oil. LC/MS (Method H, ESI): [M+H]⁺=390.1, RT=0.89 min.

To a solution of 5-[5-chloro-2-(difluoromethoxy)phenyl]-[[2-(trimethylsilyl)ethoxy]methyl]-1H-pyrazol-4-amine (4.01 g, 10.3 mmol) in DMA (40 mL) was added successively imidazo[1,2-b]pyridazine-3-carboxylic acid (1.80 g, 11.03 mmol), (7-Azabenzotriazol-1-yloxy)tripyrrolidinophosphonium hexafluorophosphate (PyAOP) (6.30 g, 12.1 mmol), DIPEA (4.00 g, 30.9 mmol) and 4-dimethylaminopyridine (120 mg, 0.982 mmol). The reaction mixture was stirred at 60° C. overnight and allowed to cool to room temperature. Water (100 mL) was added. The resulting mixture was extracted with ethyl acetate (3×200 mL) and the organic layers combined. The organic extracts were washed with 1×100 mL of brine, dried over anhydrous sodium sulfate and concentrated under vacuum. The residue was purified by flash chromatography on silica gel eluting with ethyl acetate and petroleum ether gradient (0-60% ethyl acetate). The appropriate fractions were combined and concentrated under vacuum to give 5.02 g (91%) of N-[5-[5-chloro-2-(difluoromethoxy)phenyl]-1-[[2-(trimethylsilyl)ethoxy]methyl]-1H-pyrazol-4-yl]imidazo[1,2-b]pyridazine-3-carboxamide as a yellow solid. LC/MS (Method H, ESI, m/z): [M+H]⁺=535.2, R_T=1.07 min.

To a solution of 4 N HCl in dioxane (40 mL) was added N-[5-[5-chloro-2-(difluoromethoxy)phenyl]-1-[[2-(trimethylsilyl)ethoxy]methyl]-1H-pyrazol-4-yl]imidazo[1,2-b]pyridazine-3-carboxamide (4.00 g, 7.48 mmol) in portions. The resulting mixture was stirred at room temperature for 2 h and then concentrated under vacuum. 10% sodium bicarbonate aqueous solution was added until pH reached ~9. The solids were collected by filtration, washed by water and dried under vacuum to obtain 3.01 g (99%) of N-[3-[5-chloro-2-(difluoromethoxy)phenyl]-1H-pyrazol-4-yl]imidazo[1,2-b]pyridazine-3-carboxamide as an off-white solid. LC/MS (Method H, ESI): [M+H]⁺=405.0, R_T=0.77 min.

Iodomethane (28 mg, 0.197 mmol) was added to a mixture of N-[3-[5-chloro-2-(difluoromethoxy)phenyl]-1H-pyrazol-4-yl]imidazo[1,2-b]pyridazine-3-carboxamide (100 mg, 0.247 mmol) and Cs₂CO₃ (80.0 mg, 0.246 mmol) in N,N-dimethylformamide (5.0 mL). The reaction mixture was stirred for 30 min at room temperature. Water (20 mL) was added. The resulting solution was extracted with 3×50 mL of ethyl acetate and the organic layers combined. The organic layers were washed with brine, dried over anhydrous sodium sulfate and concentrated under vacuum. The residue was purified by Prep-HPLC with the following conditions: Column: XBridge Prep C18 OBD Column, 5 um, 19*150 mm; Mobile Phase A: Water (0.1% NH₄HCO₃), Mobile Phase B: ACN; Flow rate: 30 mL/min; Gradient: 25% B to 45% B in 8 min; 254/220 nm; Detector to obtain 16.0 mg (15%) of N-[3-[5-chloro-2-(difluoromethoxy)phenyl]-1-methyl-1H-pyrazol-4-yl]imidazo[1,2-b]pyridazine-3-carboxamide as a white solid. LC/MS (Method D, ESI): [M+H]⁺=419.1, RT=1.47 min; ¹H NMR (400 MHz, CD₃OD-d₄): δ (ppm) 8.59 (dd, J=4.4, 1.6 Hz, 1H), 8.47 (s, 1H), 8.35 (s, 1H), 8.27 (dd, J=9.2, 1.6 Hz, 1H), 7.67 (d, J=2.8 Hz, 1H), 7.58 (dd, J=8.8, 2.8 Hz, 1H), 7.50 (dd, J=9.2, 4.8 Hz, 1H), 7.47 (d, J=9.2 Hz, 1H), 6.81 (t, J=73.6 Hz, 1H), 4.02 (s, 3H).

Example 9

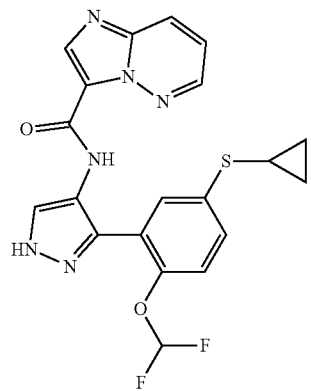 [SMILES: O=C(Nc1c[nH]nc1-c1cc(SC2CC2)ccc1OC(F)F)c1cnc2cccnn12]

N-[3-[5-(cyclopropylsulfanyl)-2-(difluoromethoxy)phenyl]-1H-pyrazol-4-yl]imidazo[1,2-b]pyridazine-3-carboxamide

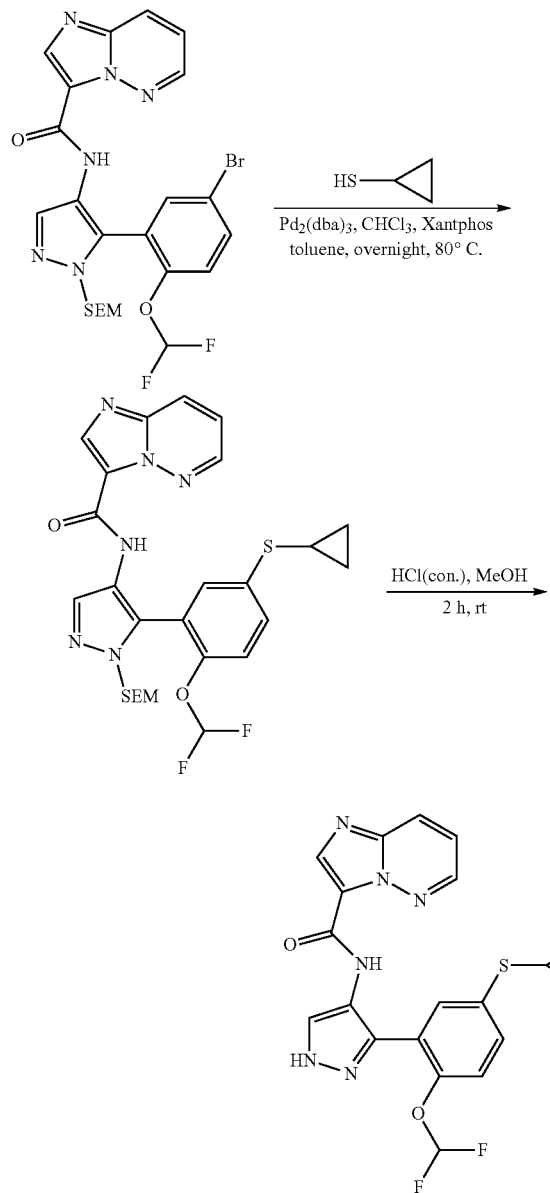

To a solution of cyclopropanethiol (46.0 mg, 0.620 mmol) in toluene (15 mL) was added sodium hydride (24.0 mg, 1.00 mmol) under nitrogen. The resulting solution was stirred at room temperature for 1 h under nitrogen.

To the above solution under nitrogen was added N-[5-[5-bromo-2-(difluoromethoxy)phenyl]-1-[[2-(trimethylsilyl)ethoxy]methyl]-1H-pyrazol-4-yl]imidazo[1,2-b]pyridazine-3-carboxamide (100 mg, 0.173 mmol), Pd$_2$(dba)$_3$·CHCl$_3$ (10 mg, 0.0966 mmol) and XantPhos (10 mg, 0.0173 mmol). The reaction mixture was stirred at 85° C. overnight and allowed to cool to room temperature. The resulting mixture was concentrated under vacuum. The residue was purified by flash chromatography on silica gel eluting with ethyl acetate and petroleum ether gradient (0-90% EtOAc). The appropriate fractions were combined and concentrated under vacuum. This resulted in 90.1 mg (91%) of N-[5-[5-(cyclopropylsulfanyl)-2-(difluoromethoxy)phenyl]-1-[[2-(trimethylsilyl)ethoxy]methyl]-1H-pyrazol-4-yl]imidazo[1,2-b]pyridazine-3-carboxamide as a yellow solid. LC/MS (Method H, ESI): [M+H]$^+$=573.3, R$_T$=1.13 min.

To a mixture of methanol (2.0 mL) and concentrated HCl (2.0 mL, 12 N) was added N-[5-[5-(cyclopropylsulfanyl)-2-(difluoromethoxy)phenyl]-[[2-(trimethylsilyl)ethoxy]methyl]-1H-pyrazol-4-yl]imidazo[1,2-b]pyridazine-3-carboxamide (90.0 mg, 0.157 mmol) in several portions. The reaction mixture was stirred at room temperature for 3 h and concentrated under vacuum. The residue was purified by Prep-HPLC with the following conditions: Column:)(Bridge Prep C18 OBD Column, 5 um, 19*150 mm; Mobile Phase A: Water (0.1% NH$_4$HCO$_3$), Mobile Phase B: ACN; Flow rate: 30 mL/min; Gradient: 25% B to 45% B in 8 min; 254/220 nm; Detector to give 18.1 mg (26%) of N-[3-[5-(cyclopropylsulfanyl)-2-(difluoromethoxy)phenyl]-1H-pyrazol-4-yl]imidazo[1,2-b]pyridazine-3-carboxamide as a white solid. LC/MS (Method C, ESI): [M+H]$^+$=443.1, R$_T$=1.15 min; $^1$H NMR (400 MHz, CD$_3$OD-d$_4$): δ (ppm) 8.59 (d, J=4.4 Hz, 1H), 8.46 (s, 1H), 8.36 (s, 1H), 8.25 (d, J=8.4 Hz, 1H), 7.63 (s, 1H), 7.56 (d, J=8.8 Hz, 1H), 7.49 (dd, J=8.8, 4.4 Hz, 1H), 7.41 (d, J=8.4 Hz, 1H), 6.73 (t, J=73.7 Hz, 1H), 2.33-2.22 (m, 1H), 1.18-1.06 (m, 2H), 0.69-0.57 (m, 2H).

Example 10

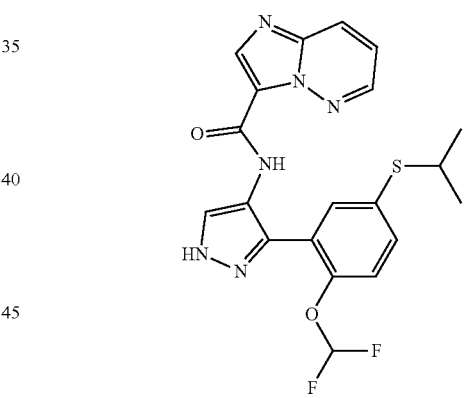

N-[3-[2-(difluoromethoxy)-5-(propan-2-ylsulfanyl)phenyl]-1H-pyrazol-4-yl]imidazo[1,2-b]pyridazine-3-carboxamide

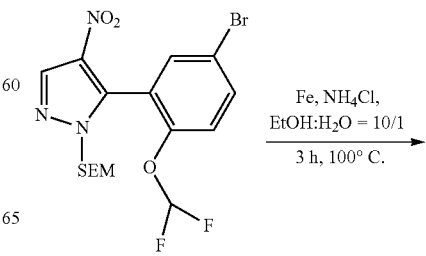

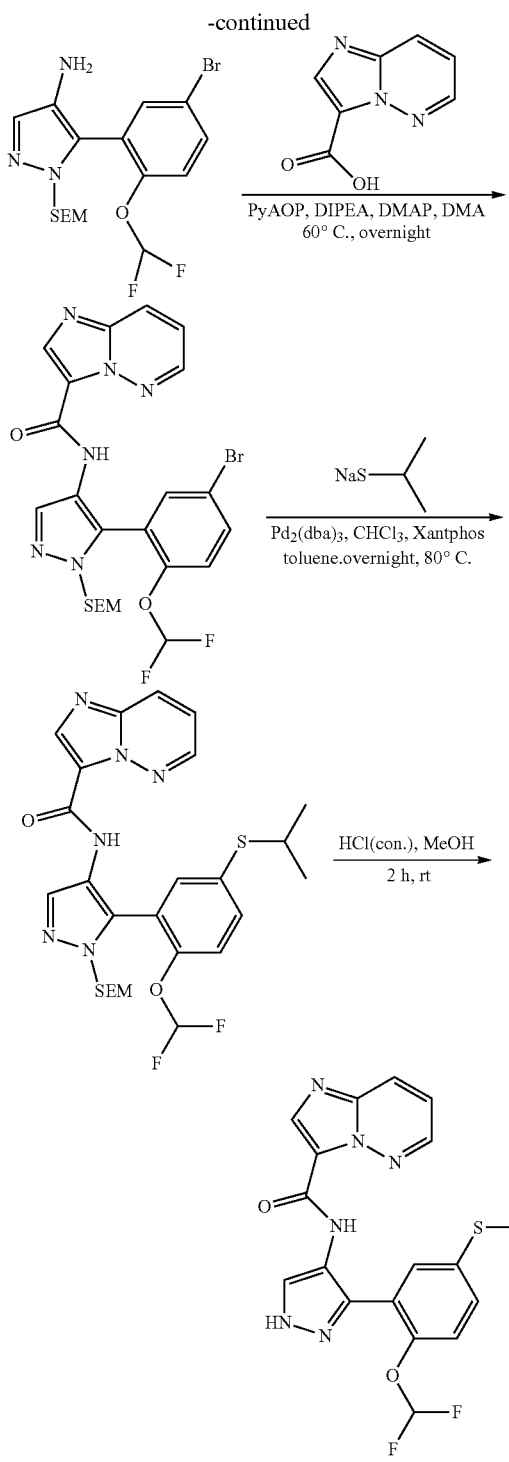

Iron powder (480 mg, 8.60 mmol) and NH₄Cl (250 mg) was added to a solution of 5-[5-bromo-2-(difluoromethoxy) phenyl]-4-nitro-1-[[2-(trimethylsilyl)ethoxy]methyl]-1H-pyrazole (400 mg, 0.861 mmol) in ethanol (20 mL) and water (2 mL). The reaction mixture was stirred at reflux for 3 h under nitrogen. The solids were filtered off and washed with ethanol. The filtrate was concentrated under vacuum. The residue partitioned between EtOAc and brine. The organic phase was dried over anhydrous sodium sulfate and concentrated under vacuum. This resulted in 400 mg (crude) of 5-[5-bromo-2-(difluoromethoxy)phenyl]-[[2-(trimethyl-silyl)ethoxy]methyl]-1H-pyrazol-4-amine as light yellow oil. LC/MS (Method H, ESI): [M+H]⁺=434.0, R$_T$=0.90 min.

To a solution of 5-[5-bromo-2-(difluoromethoxy)phenyl]-1-[[2-(trimethylsilyl)ethoxy]methyl]-1H-pyrazol-4-amine (400 mg, 0.921 mmol) in DMA (30 mL) was added imidazo[1,2-b]pyridazine-3-carboxylic acid (160 mg, 0.981 mmol), (7-Azabenzotriazol-1-yloxy)tripyrrolidinophosphonium hexafluorophosphate (PyAOP) (572 mg, 1.10 mmol), 4-dimethylaminopyridine (11.0 mg, 0.0901 mmol) and DIPEA (355 mg, 2.75 mmol). The resulting solution was stirred at 60° C. overnight and allowed to cool to room temperature. Water (100 ml) was added. The resulting mixture was extracted with 3×300 mL of ethyl acetate and the organic layers combined. The organic phase was washed with 1×100 mL of brine, dried over anhydrous sodium sulfate and concentrated under vacuum. The residue was purified by flash chromatography on silica gel eluting with ethyl acetate and petroleum ether gradient (0-70% EtOAc). The appropriate fractions were combined and concentrated under vacuum to give 300 mg (56%) of N-[5-[5-bromo-2-(difluoromethoxy)phenyl]-1-[[2-(trimethylsilyl)ethoxy]methyl]-1H-pyrazol-4-yl]imidazo[1,2-b]pyridazine-3-carboxamide as a yellow solid. LC/MS (Method H, ESI): [M+4]⁺=581.1, R$_T$=1.08 min.

To a solution of N-[5-[5-bromo-2-(difluoromethoxy)phenyl]-1-[[2-(trimethylsilyl)ethoxy]methyl]-1H-pyrazol-4-yl]imidazo[1,2-b]pyridazine-3-carboxamide (120 mg, 0.207 mmol) in toluene (10 mL) was added (propan-2-ylsulfanyl)sodium (60.0 mg, 0.611 mmol), Pd₂(dba)₃·CHCl₃ (11.0 mg, 0.0106 mmol) and XantPhos (11.0 mg, 0.0190 mmol) under nitrogen. The resulting mixture was stirred at 80° C. overnight under nitrogen and allowed to cool to room temperature. The resulting mixture was concentrated under vacuum. The residue was purified by flash chromatography on silica gel eluting with ethyl acetate and petroleum ether gradient (0-70% EtOAc) to give 100 mg (84%) of N-[5-[2-(difluoromethoxy)-5-(propan-2-ylsulfanyl)phenyl]-[[2-(trimethylsilyl)ethoxy]methyl]-1H-pyrazol-4-yl]imidazo[1,2-b]pyridazine-3-carboxamide as a white solid. LC/MS (Method H, ESI): [M+H]⁺=575.2, R$_T$=1.15 min.

To a mixture of methanol (5.0 mL) and concentrated HCl (5.0 mL, 12 N) was added N-[5-[2-(difluoromethoxy)-5-(propan-2-ylsulfanyl)phenyl]-[[2-(trimethylsilyl)ethoxy]methyl]-1H-pyrazol-4-yl]imidazo[1,2-b]pyridazine-3-carboxamide (120 mg, 0.209 mmol). The resulting solution was stirred at room temperature for 2 h and concentrated under vacuum. The residue was purified by Prep-HPLC with the following conditions: Column: XBridge Prep C18 OBD Column, 5 um, 19*150 mm; Mobile Phase A: Waters (0.1% NH₄HCO₃), Mobile Phase B: ACN; Flow rate: 30 mL/min; Gradient: 25% B to 45% B in 8 min; 254/220 nm Detector to obtain 7.70 mg of N-[3-[2-(difluoromethoxy)-5-(propan-2-ylsulfanyl)phenyl]-1H-pyrazol-4-yl]imidazo[1,2-b]pyridazine-3-carboxamide as a white solid. LC/MS (Method B, ESI): [M+H]⁺=445.2, R$_T$=2.56 min; ¹H NMR (300 MHz, CD₃OD-d₄): δ (ppm) 8.56 (d, J=4.5 Hz, 1H), 8.45 (s, 1H), 8.36 (s, 1H), 8.24 (dd, J=9.2, 1.4 Hz, 1H), 7.64 (d, J=2.1 Hz, 1H), 7.58 (dd, J=8.7, 2.4 Hz, 1H), 7.48 (dd, J=9.3, 4.5 Hz, 1H), 7.41 (d, J=8.4 Hz, 1H), 6.76 (t, J=73.5 Hz, 1H), 3.49-3.43 (m, 1H), 1.28 (d, J=6.3 Hz, 6H).

Example 11

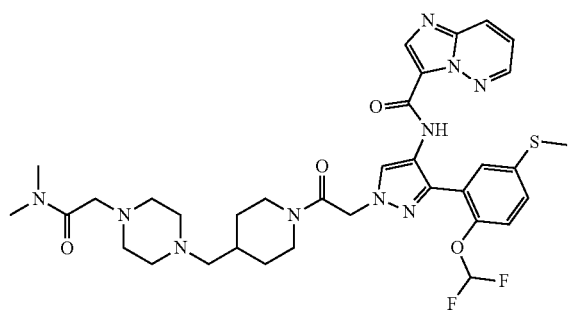

N-[3-[2-(difluoromethoxy)-5-(methylsulfanyl)phenyl]-1-[2-[4-([4-[(dimethylcarbamoyl)methyl]piperazin-1-yl]methyl)piperidin-1-yl]-2-oxoethyl]-1H-pyrazol-4-yl]pyrazolo[1,5-a]pyrimidine-3-carboxamide To a solution of N,N-dimethyl-2-[4-(piperidin-4-ylmethyl)piperazin-1-yl]acetamide (300 mg, 1.12 mmol) in dichloromethane (10 mL) and saturated sodium carbonate (3.8 mL) was added 2-bromoacetyl bromide (335 mg, 1.66 mmol) dropwise under ice bath cooling at the rate maintaining internal temperature below 5° C. The resulting solution was stirred for 1 h under ice water bath cooling. The resulting solution was extracted with 3×50 mL of dichloromethane and the organic layers combined. The organic layers were washed with brine and dried over anhydrous sodium sulfate and concentrated without heating under vacuum. This resulted in 300 mg of 2-(4-[[1-(2-bromoacetyl)piperidin-4-yl]methyl]piperazin-1-yl)-N,N-dimethylacetamide as yellow oil, which was used without further purification. LC/MS (Method H, ESI): $[M+H]^+$=389.2, $R_T$=0.17 min.

A solution of crude 2-(4-[1-(2-bromoacetyl)piperidin-4-yl]methylpiperazin-1-yl)-N,N-dimethylacetamide (120 mg) in DMF (2.0 mL) was added dropwise to a mixture of N-[3-[2-(difluoromethoxy)-5-(methylsulfanyl)phenyl]-1H-pyrazol-4-yl]pyrazolo[1,5-a]pyrimidine-3-carboxamide (120 mg, 0.288 mmol) and $Cs_2CO_3$ (400 mg, 1.23 mmol) in N,N-dimethylformamide (8.0 mL) at 65° C. The reaction mixture was stirred at 65° C. for 2 h and allowed to cool to

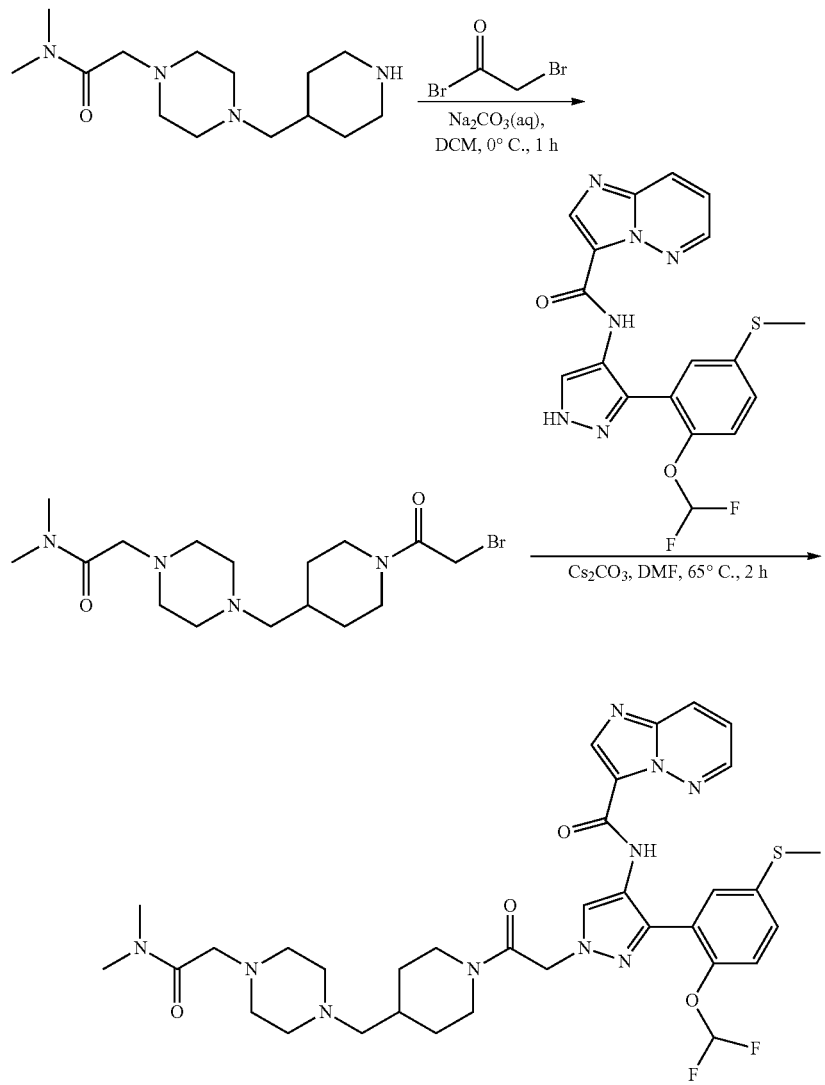

room temperature. Water (20 mL) was added. The resulting mixture was extracted with 3×50 mL of ethyl acetate and the organic layers combined. The organic extracts were washed with brine, dried over anhydrous sodium sulfate and concentrated under vacuum. The residue was purified by Prep-HPLC with the following conditions: Column: XBridge Prep C18 OBD Column, 5 um, 19*150 mm; Mobile Phase A: Water (0.1% NH$_4$HCO$_3$), Mobile Phase B: ACN; Flow rate: 30 mL/min; Gradient: 25% B to 45% B in 8 min; 254/220 nm Detector to give 6.20 mg of N-[3-[2-(difluoromethoxy)-5-(methylsulfanyl)phenyl]-1-[2-[4-([4-[(dimethylcarbamoyl)methyl]piperazin-1-yl]methyl)piperidin-1-yl]-2-oxoethyl]-1H-pyrazol-4-yl]pyrazolo[1,5-a]pyrimidine-3-carboxamide as a white solid. LC/MS (Method A, ESI): [M+H]$^+$=725.4, R$_T$=1.38 min; 1H NMR (400 MHz, CD$_3$OD-d$_4$): δ (ppm) 8.58 (dd, J=4.8, 1.6 Hz, 1H), 8.47 (s, 1H), 8.43 (s, 1H), 8.26 (dd, J=9.4, 1.4 Hz, 1H), 7.57 (d, J=2.4 Hz, 1H), 7.52-7.49 (m, 2H), 7.42 (d, J=8.4 Hz, 1H), 6.74 (t, J=73.8 Hz, 1H), 5.31 (d, J=16.4 Hz, 1H), 5.22 (d, J=16.4 Hz, 1H), 4.54-4.51 (m, 1H), 4.05-4.01 (m, 1H), 3.24 (s, 2H), 3.22-3.14 (m, 1H), 3.11 (s, 3H), 2.95 (s, 3H), 2.87-2.70 (m, 1H), 2.68-2.45 (m, 11H), 2.27-2.25 (m, 2H), 1.93-1.84 (m, 3H), 1.38-1.14 (m, 2H).

Example 12

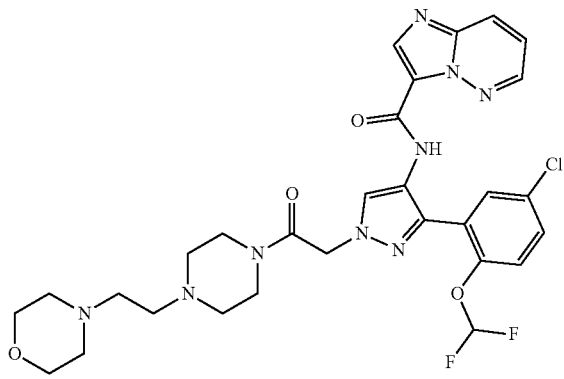 [SMILES: O=C(Nc1cn(CC(=O)N2CCN(CCN3CCOCC3)CC2)nc1-c1cc(Cl)ccc1OC(F)F)c1cnc2cccnn12]

N-[3-[5-chloro-2-(difluoromethoxy)phenyl]-1-(2-[4-[2-(morpholin-4-yl)ethyl]piperazin-1-yl]-2-oxoethyl)-1H-pyrazol-4-yl]imidazo[1,2-b]pyridazine-3-carboxamide

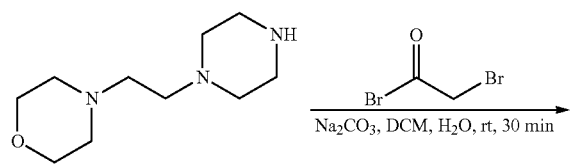

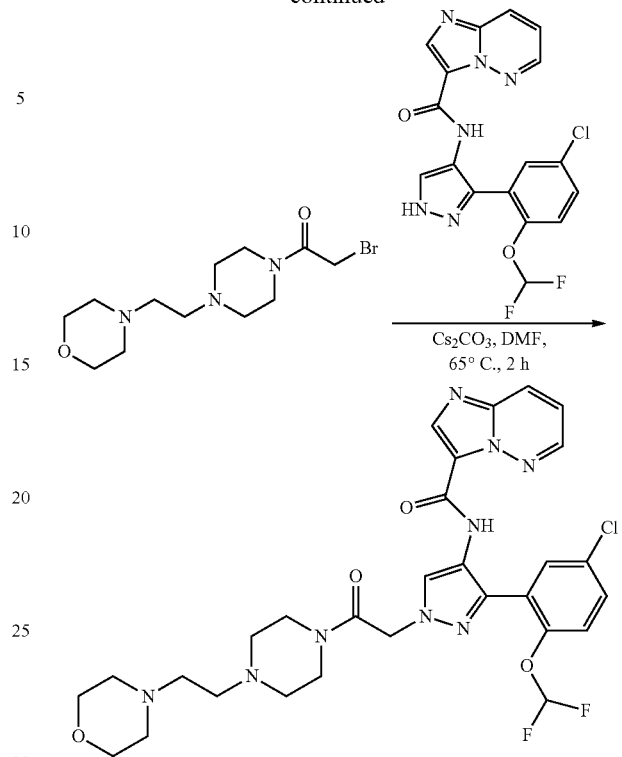

To a stirring mixture of 4-[2-(piperazin-1-yl)ethyl]morpholine (200 mg, 1.00 mmol), dichloromethane (10 mL), saturated sodium carbonate (4.2 mL) under ice bath cooling was added dropwise 2-bromoacetyl bromide (243 mg, 1.20 mmol) at the rate maintaining internal temperature below 5° C. The reaction mixture was then stirred for another 30 min at room temperature. Phases were separated and the aqueous phase was extracted with 3×20 mL of dichloromethane and the organic layers combined. The organic layers were washed with brine, dried over anhydrous sodium sulfate and concentrated under vacuum to give 200 mg of crude 2-bromo-1-[4-[2-(morpholin-4-yl)ethyl]piperazin-1-yl]ethan-1-one, which was used right away for next step without further purification. LC/MS (Method H, ESI): [M+H]$^+$=320.1, R$_T$=0.28 min.

A solution of Crude 2-bromo-1-4-[2-(morpholin-4-yl)ethyl]piperazin-1-ylethan-1-one (94.9 mg) in DMF (2 mL) from previous step was added to a mixture of N-[3-[5-chloro-2-(difluoromethoxy)phenyl]-1H-pyrazol-4-yl]imidazo[1,2-b]pyridazine-3-carboxamide (100 mg, 0.247 mmol) and Cs$_2$CO$_3$ (161 mg, 0.494 mmol) in DMF (10 mL). The reaction mixture was stirred at 65° C. for 2 h and allowed to cool to room temperature. Water (20 mL) was added. The resulting mixture was extracted with 3×50 mL of ethyl acetate and the organic layers combined. The organic extracts were washed with brine, dried over anhydrous sodium sulfate and concentrated under vacuum. The residue was purified by flash chromatography on silica gel eluting with ethyl acetate and petroleum ether gradient (0-90% ethyl acetate). The appropriate fractions were combined and concentrated under vacuum. The residue was further purified by Prep-HPLC with the following conditions: Column: XBridge Prep C$_{18}$ OBD Column, 5 um, 19*150 mm; Mobile Phase A: Water (0.1% NH$_4$HCO$_3$), Mobile Phase B: ACN; Flow rate: 30 mL/min; Gradient: 25% B to 45% B in 8 min; 254/220 nm Detector to afford 3.40 mg of N-[3-[5-chloro- 2-(difluoromethoxy)phenyl]-1-(2-[4-[2-(morpholin-4-yl)ethyl]piperazin-1-yl]-2-oxoethyl)-1H-pyrazol-4-yl]imidazo[1,2-b]pyridazine-3-carboxamide as an off-white solid. LC/MS (Method F, ESI): [M+H]$^+$=644.3, R$_T$=0.95 min; $^1$H NMR (400 MHz, CD$_3$OD-d$_4$): δ (ppm) 8.59 (dd, J=4.4, 1.6 Hz, 1H), 8.48 (s, 1H), 8.43 (s, 1H), 8.27 (dd, J=9.4, 1.4 Hz, 1H), 7.72 (d, J=2.4 Hz, 1H), 7.60 (dd, J=8.8, 2.4 Hz, 1H), 7.52-7.47 (m, 2H), 6.80 (t, J=73.6 Hz, 1H), 5.28 (s, 2H), 3.79-3.61 (m, 8H), 2.66-2.45 (m, 12H).

Example 13

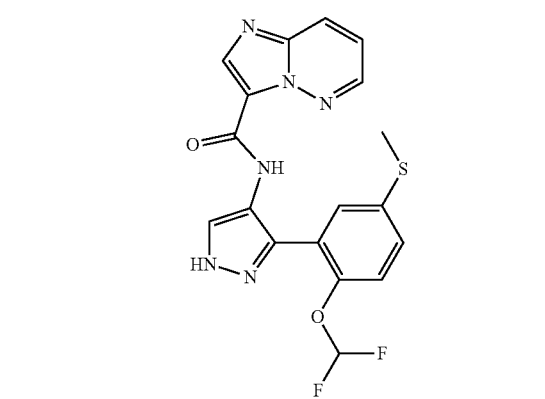 [SMILES: CSc1ccc(OC(F)F)c(-c2n[nH]cc2NC(=O)c2cnc3cccnn23)c1]

N-[3-[2-(difluoromethoxy)-5-(methylsulfanyl)phenyl]-1H-pyrazol-4-yl]imidazo[1,2-b]pyridazine-3-carboxamide

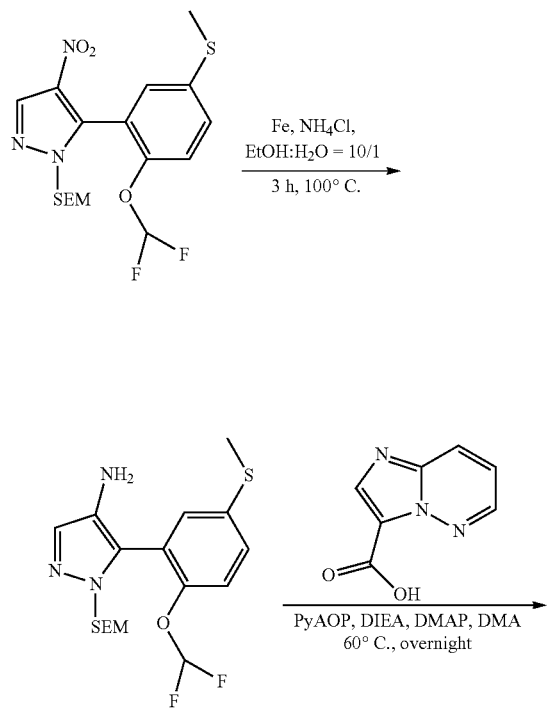

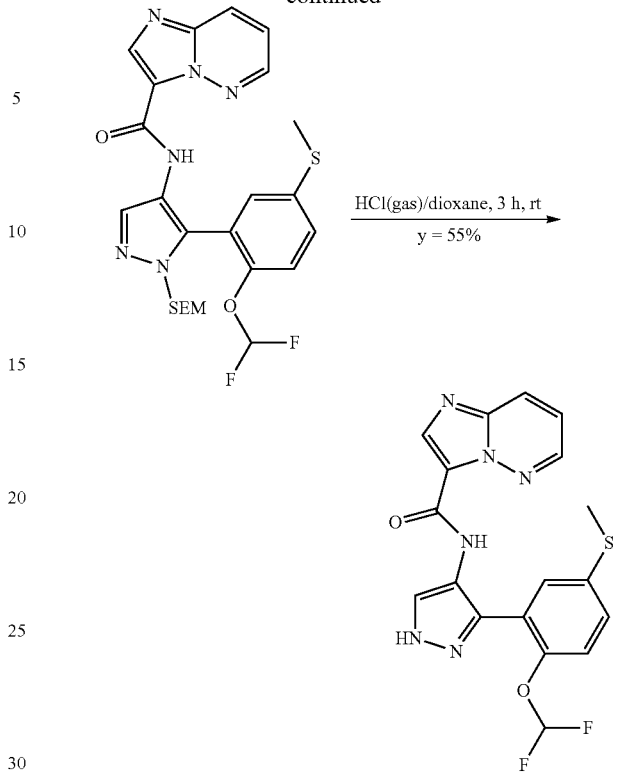

Iron powder (647 mg) and NH$_4$Cl (310 mg, 5.79 mmol) was added to a solution of 5-[2-(difluoromethoxy)-5-(methylsulfanyl)phenyl]-4-nitro-1-[[2-(trimethylsilyl)ethoxy]methyl]-1H-pyrazole (500 mg, 1.16 mmol) in ethanol (10 mL) and water (1.0 mL). The reaction mixture was stirred at reflux for 4 h under nitrogen and allowed to cool to room temperature. The solids were filtered off and washed with ethanol. The filtrate was concentrated under vacuum. The residue was partitioned between EtOAc and brine. The organic phase was dried over anhydrous sodium sulfate and concentrated under vacuum to give 400 mg of 5-[2-(difluoromethoxy)-5-(methylsulfanyl)phenyl]-1-[[2-(trimethylsilyl)ethoxy]methyl]-1H-pyrazol-4-amine as light yellow oil. LC/MS (Method H, ESI): [M+H]$^+$=402.0, R$_T$=0.80 min.

To a solution of 5-[2-(difluoromethoxy)-5-(methylsulfanyl)phenyl]-1-[[2-(trimethylsilyl)ethoxy]methyl]-1H-pyrazol-4-amine (150 mg, 0.374 mmol,) in DMA (5.0 mL) was added imidazo[1,2-b]pyridazine-3-carboxylic acid (73.1 mg, 0.448 mmol), (7-Azabenzotriazol-1-yloxy)tripyrrolidinophosphonium hexafluorophosphate (PyAOP) (234 mg, 0.448 mmol), DIPEA (145 mg, 1.12 mmol) and 4-dimethylaminopyridine (4.56 mg, 0.0373 mmol). The reaction mixture was stirred at 60° C. overnight and allowed to cool to room temperature. Water (50 mL) was added. The resulting solution was extracted with 3×50 mL of ethyl acetate and the organic layers combined. The organic extracts were washed with 1×50 mL of brine, dried over anhydrous sodium sulfate and concentrated under vacuum. The residue was purified by flash chromatography on silica gel eluting with ethyl acetate and petroleum ether gradient (0-50% EtOAc). The appropriate fractions were combined and concentrated under vacuum to obtain 150 mg (73%) of N-[5-[2-(difluoromethoxy)-5-(methylsulfanyl)phenyl]-1-[[2-(trimethylsilyl)ethoxy]methyl]-1H-pyrazol-4-yl]imidazo[1, 2-b]pyridazine-3-carboxamide as a yellow solid. LC/MS (Method H, ESI): [M+H]$^+$=547.2, R$_T$=1.07 min.

To a mixture of methanol (5.0 mL) and concentrated HCl aqueous solution (5.0 mL, 12 N) was added N-[5-[2-(difluoromethoxy)-5-(methylsulfanyl)phenyl]-1-[[2-(trimethylsilyl)ethoxy]methyl]-1H-pyrazol-4-yl]imidazo[1,2-b]pyridazine-3-carboxamide (120 mg, 0.220 mmol) in several portions. The resulting solution was stirred at room temperature for 3 h and concentrated under vacuum (to remove excess HCl and MeOH). 20% aqueous sodium carbonate solution was added to the mixture until pH reached 9. The solids were collected by filtration, washed with water and dried to give 50.1 mg (55%) of N-[3-[2-(difluoromethoxy)-5-(methylsulfanyl)phenyl]-1H-pyrazol-4-yl]imidazo[1,2-b]pyridazine-3-carboxamide as a brown solid. LC/MS (Method A, ESI): [M+H]$^+$=417.1, R$_T$=1.61 min; $^1$H NMR (400 MHz, CDCl$_3$): δ (ppm) 10.58 (s, 1H), 8.61 (s, 1H), 8.53 (s, 1H), 8.48 (dd, J=4.4, 1.2 Hz, 1H), 8.17 (dd, J=9.4, 1.4 Hz, 1H), 7.56 (d, J=2.0 Hz, 1H), 7.39 (dd, J=8.4, 2.4 Hz, 1H), 7.33 (d, J=8.4 Hz, 1H), 7.27 (dd, J=9.2, 4.4 Hz, 1H), 6.44 (t, J=73.6 Hz, 1H), 2.53 (s, 3H).

Table 1 provides a listing of the compounds above along with other representative compounds of the present invention that were prepared using similar procedures.

TABLE 1

| Ex. | Structure | Name |
|---|---|---|
| 1 | 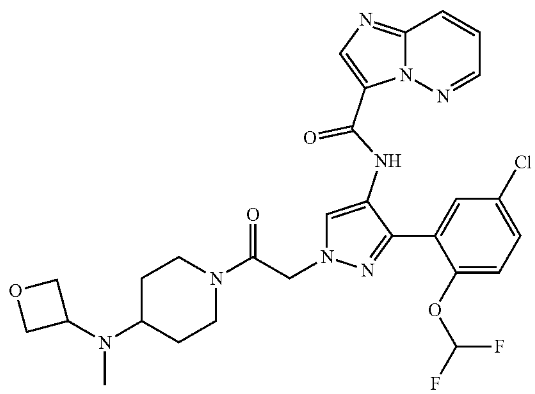 [SMILES: CN(C1CCN(C(=O)Cn2cc(NC(=O)c3cnc4cccnn34)c(-c3cc(Cl)ccc3OC(F)F)n2)CC1)C1COC1] | N-[3-[5-chloro-2-(difluoromethoxy)phenyl]-1-[2-[4-[methyl(oxetan-3-yl)amino]-1-piperidyl]-2-oxo-ethyl]pyrazol-4-yl]imidazo[1,2-b]pyridazine-3-carboxamide or N-[3-[5-chloro-2-(difluoromethoxy)phenyl]-1-(2-[4-[methyl(oxetan-3-yl)amino]piperidin-1-yl]-2-oxoethyl)-1H-pyrazol-4-yl]imidazo[1,2-b]pyridazine-3-carboxaniide |
| 2 | 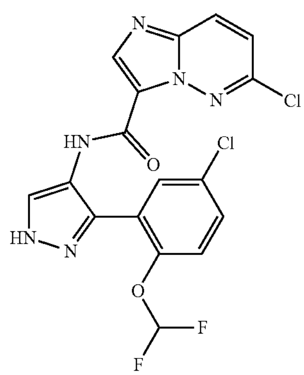 [SMILES: O=C(Nc1c[nH]nc1-c1cc(Cl)ccc1OC(F)F)c1cnc2ccc(Cl)nn12] | 6-chloro-N-[3-[5-chloro-2-(difluoromethoxy)phenyl]-1H-pyrazol-4-yl]imidazo[1,2-b] pyridazine-3-carboxamide |
| 3 | 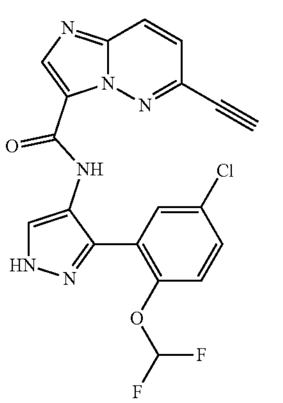 [SMILES: C#Cc1ccc2ncc(C(=O)Nc3c[nH]nc3-c3cc(Cl)ccc3OC(F)F)n2n1] | N-[3-[5-chloro-2-(difluoromethoxy)phenyl]-1H-pyrazol-4-yl]-6-ethynyl-imidazo[1,2-b]pyridazine-3-carboxamide |

TABLE 1-continued

| Ex. | Structure | Name |
|---|---|---|
| 4 | 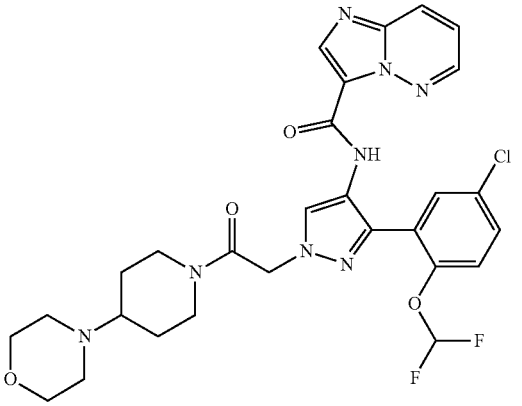 [SMILES: O=C(Nc1cn(CC(=O)N2CCC(N3CCOCC3)CC2)nc1-c1cc(Cl)ccc1OC(F)F)c1cnc2cccnn12] | N-[3-[5-chloro-2-(difluoromethoxy)phenyl]-1-[2-(4-morpholino-1-piperidyl)-2-oxo-ethyl]pyrazol-4-yl]imidazo[1,2-b]pyridazine-3-carboxamide<br>or<br>N-[3-[5-chloro-2-(difluoromethoxy)phenyl]-1-[2-[4(morpholin-4-yl)piperidin-1-yl]-2-oxoethyl]-1H-pyrazol-4-yl]imidazo[1,2-b]pyridazine-3-carboxamide |
| 5 | 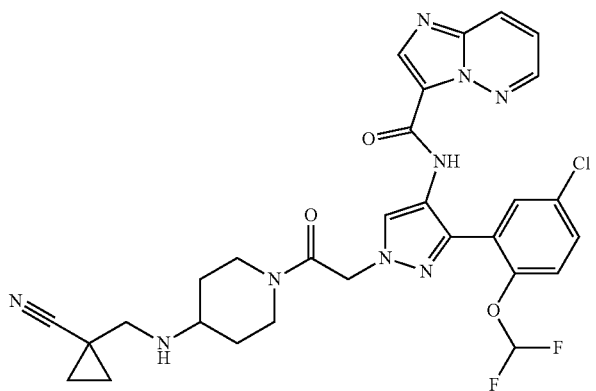 [SMILES: N#CC1(CNC2CCN(C(=O)Cn3cc(NC(=O)c4cnc5cccnn45)c(-c4cc(Cl)ccc4OC(F)F)n3)CC2)CC1] | N-[3-[5-chloro-2-(difluoromethoxy)phenyl]-1-[2-[4-[(l-cyanocyclopropyl)methylamino]-1-piperidyl]-2-oxo-ethyl]pyrazol-4-yl]imidazo[1,2-b]pyridazine-3-carboxamide<br>or<br>N-[3-[5-chloro-2-(difluoromethoxy)phenyl]-1-[2-(4-[[(l-cyanocyclopropyl)methyl]amino]piperidin-1-yl)-2-oxoethyl]-1H-pyrazol-4-yl]imidazo[1,2-b]pyridazine-3-carboxamide |
| 6 | 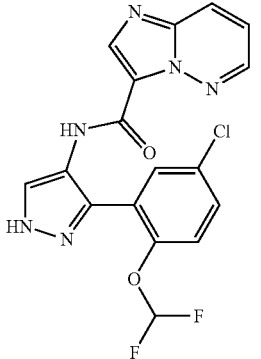 [SMILES: O=C(Nc1c[nH]nc1-c1cc(Cl)ccc1OC(F)F)c1cnc2cccnn12] | N-[3-[5-chloro-2-(difluoromelhoxy)phenyl]-1H-pyrazol-4-yl]imidazo[1,2-b]pyridazine-3-carboxamide |
| 7 | 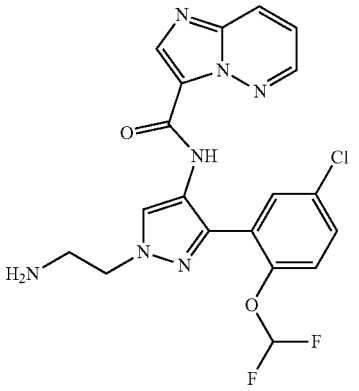 [SMILES: NCCn1cc(NC(=O)c2cnc3cccnn23)c(-c2cc(Cl)ccc2OC(F)F)n1] | N-[1-(2-aminoethyl)-3-[5-chloro-2-(difluoromethoxy)phenyl]pyrazol-4-yl]imidazo[1,2-b]pyridazine-3-carboxamide<br>or<br>N-[1-(2-aminoethyl)-3-[5-chloro-2-(difluoromethoxy)phenyl]-1H-pyrazol-4-yl]imidazo[1,2-b]pyridazine-3-carboxamide |

TABLE 1-continued

| Ex. | Structure | Name |
|---|---|---|
| 8 | 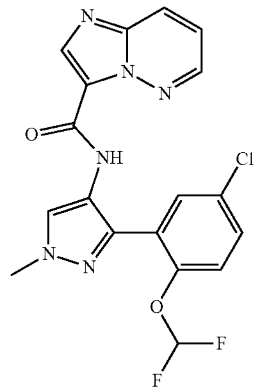 [SMILES: Cn1cc(NC(=O)c2cnc3cccnn23)c(-c2cc(Cl)ccc2OC(F)F)n1] | N-[3-[5-chloro-2-(difluoromethoxy)phenyl]-1-methyl-pyrazol-4-yl]imidazo[1,2-b]pyridazine-3-carboxamide or N-[3-[5-chloro-2-(difluoromelhoxy)phenyl]-1-methyl-1H-pyrazol-4-yl]imidazo[1,2-b]pyndazine-3-carboxamide |
| 9 | 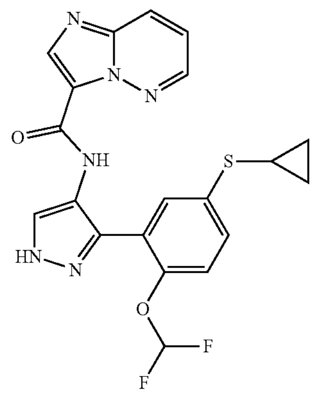 [SMILES: O=C(Nc1c[nH]nc1-c1cc(SC2CC2)ccc1OC(F)F)c1cnc2cccnn12] | N-[3-[5-cyclopropylsulfanyl-2-(difluoromethoxy)phenyl]-1H-pyrazol-4-yl]imidazo[1,2-b]pyridazine-3-carboxamide or N-[3-[5-(cyclopropylsulfanyl)-2-(difluoromethoxy)phenyl]-1H-pyrazol-4-yl]imidazo[1,2-b]pyridazine-3-carboxamide |
| 10 | 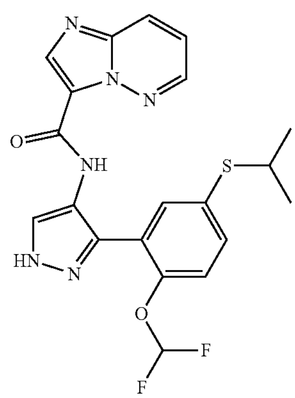 [SMILES: CC(C)Sc1ccc(OC(F)F)c(-c2n[nH]cc2NC(=O)c2cnc3cccnn23)c1] | N-[3-[2-(difluoromethoxy)-5-isopropylsulfanyl-phenyl]-1H-pyrazol-4-yl]imidazo[1,2-b]pyridazine-3-carboxamide or N-[3-[2-(difluoromethoxy)-5-(propan-2-ylsulfanyl)phenyl]-1H-pyrazol-4-yl]imidazo[1,2-b]pyridazine-3-carboxamide |
| 11 | 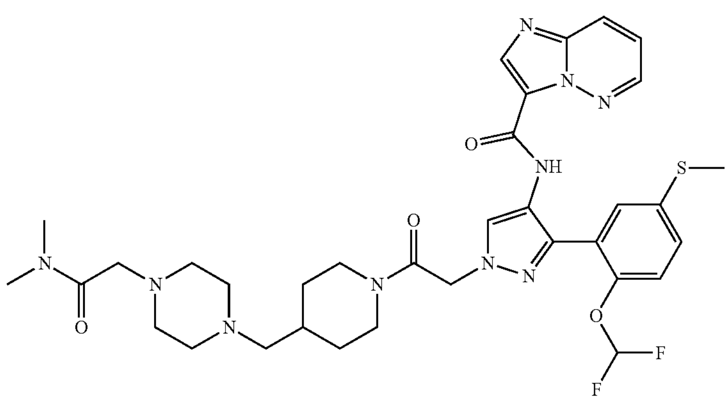 | N-[3-[2-(difluoromethoxy)-5-methylsulfanyl-phenyl]-1-[2-[4-[[4-[2-(dimethylamino)-2-oxo-ethyl]piperazin-1-yl]methyl]-1-piperidyl]-2-oxo-ethyl]pyrazol-4-yl]imidazo[1,2-b]pyridazine-3-carboxamide or N-[3-[2-(difluoromethoxy)-5-(methylsulfanyl)phenyl]-1-[2-[4-([4-[(dimethylcarbamoyl)methyl]piperazin-1-yl]methyl)piperidin-1-yl]-2-oxoethyl]-1H-pyrazol-4-yl]pyrazolo[1,5-a]pyrimidine-3-carboxamide |

TABLE 1-continued

| Ex. | Structure | Name |
|---|---|---|
| 12 | 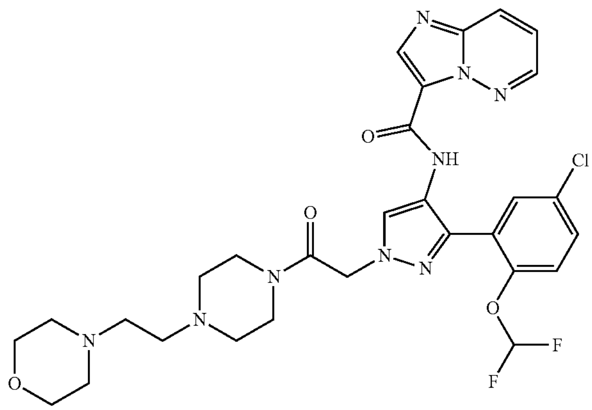 [SMILES: O=C(Nc1cn(CC(=O)N2CCN(CCN3CCOCC3)CC2)nc1-c1cc(Cl)ccc1OC(F)F)c1cnc2cccnn12] | N-[3-[5-chloro-2-(difluoromethoxy)phenyl]-1-[2-[4-(2-morpholinoethyl)piperazin-1-yl]-2-oxo-ethyl]pyrazol-4-yl]imidazo[1,2-b]pyridazine-3-carboxamide<br>or<br>N-[3-[5-chloro-2-(difluoromethoxy)phenyl]-1-(2-[4-[2-(morpholin-4-yl)ethyl]piperazin-1-yl]-2-oxoethyl)-1H-pyrazol-4-yl]imidazo[1,2-b]pyridazine-3-carboxamide |
| 13 | 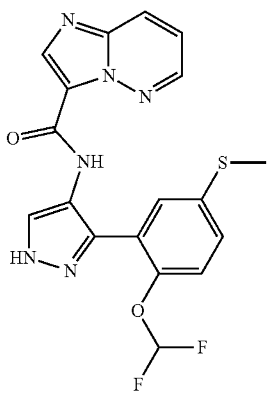 [SMILES: CSc1ccc(OC(F)F)c(-c2n[nH]cc2NC(=O)c2cnc3cccnn23)c1] | N-[3-[2-(difluoromethoxy)-5-methylsulfanyl-phenyl]-1H-pyrazol-4-yl]imidazo[1,2-b]pyridazine-3-carboxamide<br>or<br>N-[3-[2-(difluoromethoxy)-5-(methylsulfanyl)phenyl]-1H-pyrazol-4-yl]imidazo[1,2-b]pyridazine-3-carboxamide |

Enzymatic Assays

JAK Enzyme Assays were Carried Out as Follows:

The activity of the isolated recombinant JAK1 and JAK2 kinase domain was measured by monitoring phosphorylation of a peptide derived from JAK3 (Val-Ala-Leu-Val-Asp-Gly-Tyr-Phe-Arg-Leu-Thr-Thr, fluorescently labeled on the N-terminus with 5-carboxyfluorescein) using the Caliper LabChip® technology (Caliper Life Sciences, Hopkinton, Mass.). To determine inhibition constants (K), compounds were diluted serially in DMSO and added to 50 μL kinase reactions containing purified enzyme (1.5 nM JAK1, or 0.2 nM JAK2), 100 mM HEPES buffer (pH 7.2), 0.015% Brij-35, 1.5 μM peptide substrate, ATP (25 μM), 10 mM $MgCl_2$, 4 mM DTT at a final DMSO concentration of 2%. Reactions were incubated at 22° C. in 384-well polypropylene microtiter plates for 30 minutes and then stopped by addition of 25 μL of an EDTA containing solution (100 mM HEPES buffer (pH 7.2), 0.015% Brij-35, 150 mM EDTA), resulting in a final EDTA concentration of 50 mM. After termination of the kinase reaction, the proportion of phosphorylated product was determined as a fraction of total peptide substrate using the Caliper LabChip® 3000 according to the manufacturer's specifications. $K_i$ values were then determined using the Morrison tight binding model (Morrison, J. F., Biochim. Biophys. Acta. 185:269-296 (1969); William, J. W. and Morrison, J. F., Meth. Enzymol., 63:437-467 (1979)) modified for ATP-competitive inhibition [$K_i = K_{i,app}/(1+[ATP]/K_{m,app})$].

JAK1 Pathway Assay in Cell Lines was Carried Out as Follows:

Inhibitor potency ($EC_{50}$) was determined in cell-based assays designed to measure JAK1 dependent STAT phosphorylation. As noted above, inhibition of IL-4, IL-13, and IL-9 signalling by blocking the Jak/Stat signaling pathway can alleviate asthmatic symptoms in pre-clinical lung inflammation models (Mathew et al., 2001, J Exp Med 193(9): 1087-1096; Kudlacz et. al., 2008, Eur J. Pharmacol 582(1-3): 154-161).

In one assay approach, TF-1 human erythroleukemia cells obtained from the American Type Culture Collection (ATCC; Manassas, Va.) were used to measure JAK1-dependent STAT6 phosphorylation downstream of IL-13 stimulation. Prior to use in the assays, TF-1 cells were starved of GM-CSF overnight in OptiMEM medium (Life Technologies, Grand Island, N.Y.) supplemented with 0.5% charcoal/dextran stripped fetal bovine serum (FBS), 0.1 mM non-essential amino acids (NEAA), and 1 mM sodium pyruvate. The assays were run in 384-well plates in serum-free OptiMEM medium using 300,000 cells per well. In a second assay approach, BEAS-2B human bronchial epithelial cells obtained from ATCC were plated at 100,000 cells per well of a 96-well plate one day prior to the experiment. The BEAS-2B assay was run in complete growth medium (bronchial epithelial basal medium plus bulletkit; Lonza; Basel, Switzerland).

Test compounds were serially diluted 1:2 in DMSO and then diluted 1:50 in medium just before use. Diluted compounds were added to the cells, for a final DMSO concentration of 0.2%, and incubated for 30 min (for the TF-1 assay) or 1 hr (for the BEAS-2B assay) at 37° C. Then, cells were stimulated with human recombinant cytokine at their respective $EC_{90}$ concentrations, as previously determined for each individual lot. Cells were stimulated with IL-13 (R&D Systems, Minneapolis, Minn.) for 15 min at 37° C. The TF-1 cell reactions were stopped by the direct addition of 10× lysis buffer (Cell Signaling Technologies, Danvers, Mass.), whereas the BEAS-2B cell incubations were halted by the removal of medium and addition of 1× lysis buffer. The resultant samples were frozen in the plates at −80° C. Compound mediated inhibition of STAT6 phosphorylation was measured in the cell lysates using MesoScale Discovery (MSD) technology (Gaithersburg, Md.). $EC_{50}$ values were determined as the concentration of compound required for 50% inhibition of STAT phosphorylation relative to that measured for the DMSO control.

Table 2 provides JAK1 $K_i$, JAK2 $K_i$ and IL-13-pSTAT6 $IC_{50}$ information for the noted Examples.

TABLE 2

LCMS and Potency Data

| Example | LCMS (ESI) m/z [M + H]+ | LCMS RT (Min) | LCMS Method | JAK1 Ki (μM) | JAK2 Ki (μM) | IL13-pSTAT6 BEAS2B IC50 (μM) |
|---|---|---|---|---|---|---|
| 1 | 615.3 | 1.39 | A | 0.00033 | 0.00096 | 0.074 |
| 2 | 439.0 | 3.65 | K | 0.0015 | 0.0002 | 0.016 |
| 3 | 429.1 | 4.01 | K | 0.00029 | 0.000076 | 0.021 |
| 4 | 615.3 | 1.39 | A | 0.00036 | 0.0012 | 0.02 |
| 5 | 624.2 | 1.24 | E | 0.00056 | 0.0024 | 0.11 |
| 6 | 405.2 | 3.31 | K | 0.00018 | 0.000063 | 0.0045 |
| 7 | 448.1 | 1.28 | G | 0.00072 | 0.00053 | 0.034 |
| 8 | 419.1 | 1.47 | D | 0.00028 | 0.00014 | 0.006 |
| 9 | 443.1 | 1.15 | C | 0.00029 | 0.00012 | 0.011 |
| 10 | 445.2 | 2.56 | B | 0.00041 | 0.00026 | 0.0075 |
| 11 | 725.4 | 1.38 | A | 0.00051 | 0.00069 | 0.2 |
| 12 | 644.3 | 0.95 | F | 0.00065 | 0.002 | 0.15 |
| 13 | 417.1 | 1.61 | A | 0.00011 | 0.00005 | 0.0029 |

What is claimed is:

1. A compound selected from the group consisting of:

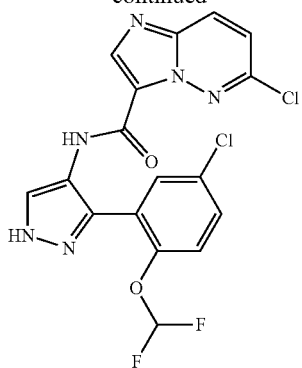

-continued

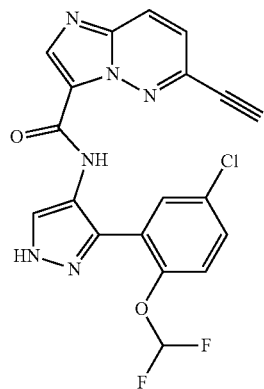

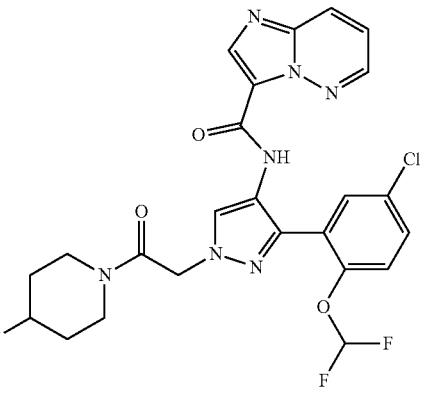

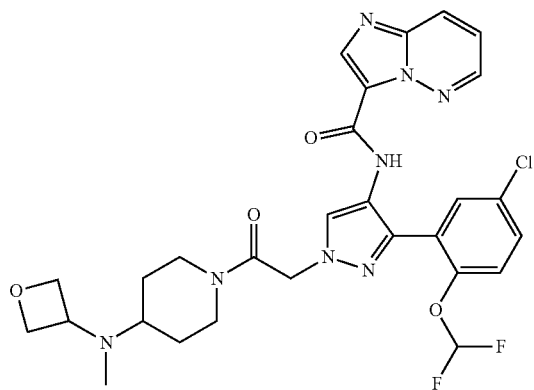

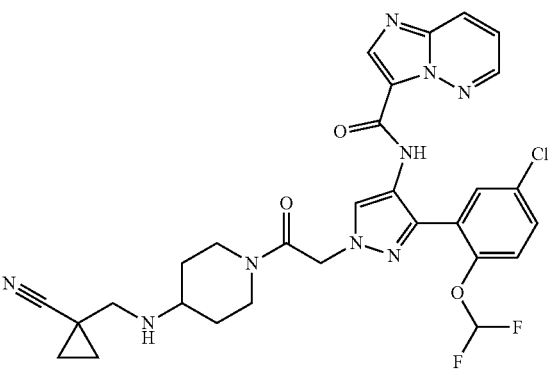

91
-continued
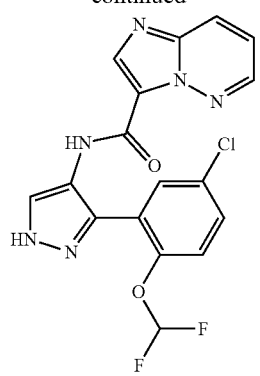
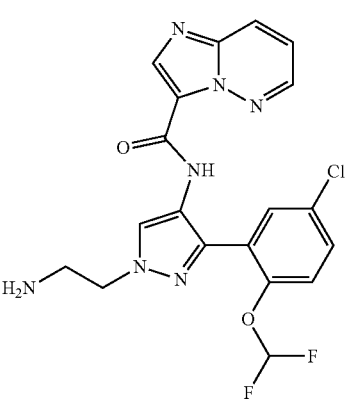
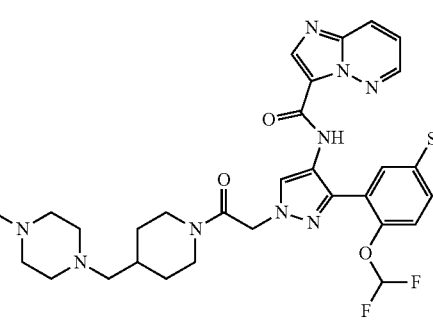
92
-continued
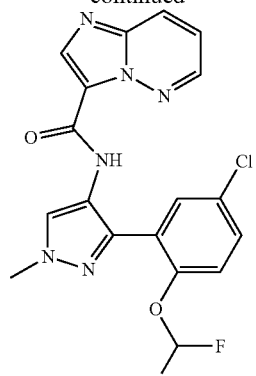
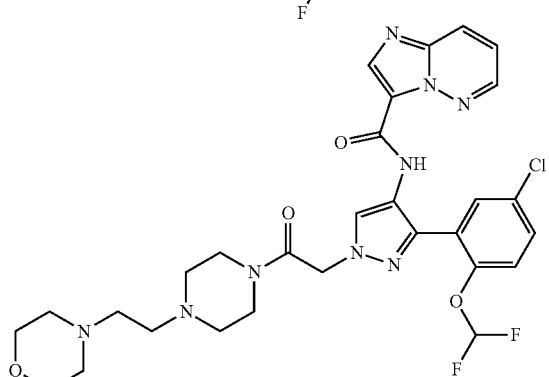
and
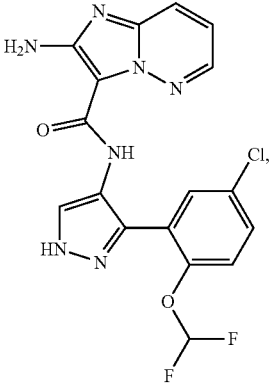
or a pharmaceutically acceptable salt thereof.
2. A pharmaceutical composition comprising a compound of claim 1 or a pharmaceutically acceptable salt thereof, and a pharmaceutically acceptable carrier, diluent or excipient.
* * * * *